United States Patent
Cool et al.

(10) Patent No.: US 9,044,496 B2
(45) Date of Patent: Jun. 2, 2015

(54) HEPARAN SULPHATE

(75) Inventors: Simon Cool, Singapore (SG); Victor Nurcombe, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 13/267,216

(22) Filed: Oct. 6, 2011

(65) Prior Publication Data

US 2012/0087899 A1  Apr. 12, 2012

Related U.S. Application Data

(60) Provisional application No. 61/391,116, filed on Oct. 8, 2010.

(51) Int. Cl.
| | |
|---|---|
| *C08B 37/10* | (2006.01) |
| *A61K 31/727* | (2006.01) |
| *C08B 37/00* | (2006.01) |
| *C12N 5/0789* | (2010.01) |

(52) U.S. Cl.
CPC ............ *A61K 31/727* (2013.01); *C08B 37/0075* (2013.01); *C12N 5/0647* (2013.01); *C12N 2500/34* (2013.01)

(58) Field of Classification Search
None
See application file for complete search history.

(56) References Cited

PUBLICATIONS

Metz et al., "Release of GPI-anchored membrane proteins by a cellassociated GPI-specific phospholipase D" The EMBO Journal (1994) vol. 13 No. 7 pp. 1741-1751.*
Arcanjo et al., Biochemical Characterization of Heparan Sulfate Derived From Murine Hemopoietic Stromal Cell Lines: A Bone Marrow-Derived Cell Line S17 and a Fetal Liver-Derived Cell Line AFT024 Journal of Cellular Biochemistry (2002) vol. 87 pp. 160-172.*
Netelenbos et al., "Differences in sulfation patterns of heparan sulfate derived from human bone marrow and umbilical vein endothelial cells" Experimental Hematology (2001) vol. 29 pp. 884-893.*
Bramono, et al., "Bone Marrow-Derived Sulfate Potentiates the Osteogenic Activity of Bone Morphogenetic Protein-2 (BMP-2)," Manuscript Draft submitted to *Bone* on Aug. 31, 2011.
Murali, et al., "Purification and Characterization of Heparan Sulfate From Human Primary Osteoblasts," *Journal of Cellular Biochemistry*,108:1132-1142 (2009).
Bramono, et al., "The Effect of Human Bone Marrow Stroma-Derived Heparan Sulfate on the Ex Vivo Expansion of Human Cord Blood Hematopoietic Stem Cells," *Pharmaceutical Research*, 28:1385-1394 (2011).

* cited by examiner

*Primary Examiner* — Eric Olson
(74) *Attorney, Agent, or Firm* — Choate, Hall & Stewart LLP; Charles E. Lyon; Kristen C. Buteau

(57) ABSTRACT

Heparan sulphate from bone marrow stroma is disclosed together with the use of heparan sulphate from bone marrow stroma in the differentiation and/or lineage commitment of stem cells.

20 Claims, 28 Drawing Sheets

Table 1. List of primers used in PCR

| Cytokines | Accession ID | F Primer | |
|---|---|---|---|
| Kit-L | NM_000899.3 | CGGAGCCTCCAGTCTGTCATTA | (SEQ ID NO.: 1) |
| IL-8 | NM_000584.2 | TCCTTGTTCCACTGTGCCTTG | (SEQ ID NO.: 4) |
| IL-6 | NM_000600.1 | AATTCGGTACATCCTCGACGG | (SEQ ID NO.: 7) |
| IL-3 | NM_000588.3 | CCAATCCATATCAAGGACGGTG | (SEQ ID NO.: 9) |
| LIF | NM_002309.2 | TCCCAACAGCAAGACGAGGAT | (SEQ ID NO.: 11) |
| TPO | NM_000460.2 | CTTCGTGACTCCCATGTCCTTC | (SEQ ID NO.: 13) |
| M-CSF | NM_000757.3 | GCAGCTGCAGGAACTCTCTTTG | (SEQ ID NO.: 15) |
| MIP1a | M24110.1 | CTCTGCAAAACCCCCCAAAT | (SEQ ID NO.: 17) |
| Fl3-L | NM_001459.2 | AAGATGCAAGGCTTGCTGGA | (SEQ ID NO.: 19) |
| G-CSF | X03438.1 | GCTTCCTGCTCAAGTGCTTAGA | (SEQ ID NO.: 21) |
| GM-CSF | NM_000758.2 | AAGTTCTCTGGAGGATGTGGCT | (SEQ ID NO.: 23) |
| IL-1a | NM_000575.3 | AAGGCTGCATGGATCAATCTGT | (SEQ ID NO.: 25) |
| IL-1b | NM_000576.2 | AGGCGGCCAGGATATAACTGA | (SEQ ID NO.: 27) |
| IL-11 | NM_000641.2 | GAAGTCCAAGAGTTCGAGACCG | (SEQ ID NO.: 29) |
| IL-1RA | NM_000877.2 | ACAAAATTGGCCAGAGAGTGG | (SEQ ID NO.: 31) |
| SDF-1 | NM_199168.2 | GCCAACGTCAAGCATCTCAAA | (SEQ ID NO.: 33) |
| Perlecan | NM_005529 | TGGACACATTCGTACCTTTCTGA | (SEQ ID NO.: 35) |
| 18sRNA | AY248756.1 | TTCGAGGCCCTGTAATTGGA | (SEQ ID NO.: 37) |

*Fig. 7*

Table 1. List of primers used in PCR

| Cytokines | Accession ID | R Primer | |
|---|---|---|---|
| Kit-L | NM_000899.3 | AGGACTCACCCCTAAGGAGTGA | (SEQ ID NO.: 3) |
| IL-8 | NM_000584.2 | TGCTTCCACATGTCCTCACAAC | (SEQ ID NO.: 6) |
| IL-6 | NM_000600.1 | GGTTGTTTTCTGCCAGTGCCT | (SEQ ID NO.: 8) |
| IL-3 | NM_000588.3 | GCTCAAAGTCGTCTGTTGAGCC | (SEQ ID NO.: 10) |
| LIF | NM_002309.2 | CAAGCTAAGCCGGATGAAGCAG | (SEQ ID NO.: 12) |
| TPO | NM_000460.2 | CCCAAGCTAAAGTCCACAGCAG | (SEQ ID NO.: 14) |
| M-CSF | NM_000757.3 | TGACCTTCTCCAGCAACTGGAG | (SEQ ID NO.: 16) |
| MIP1a | M24110.1 | CAACTGCGGAGAAAGGAGAGAA | (SEQ ID NO.: 18) |
| Flt3-L | NM_001459.2 | AGATGTTGGTCTGGACGAAGCG | (SEQ ID NO.: 20) |
| G-CSF | X03438.1 | GCACACTCACTCACCAGCTTCT | (SEQ ID NO.: 22) |
| GM-CSF | NM_000758.2 | TCATTCATCTCAGCAGCAGTGT | (SEQ ID NO.: 24) |
| IL-1a | NM_000575.3 | TCCCGTTGGTTGCTACTACCAC | (SEQ ID NO.: 26) |
| IL-1b | NM_000576.2 | TTCTGTTCCCTTTCTGCCAGC | (SEQ ID NO.: 28) |
| IL-11 | NM_000641.2 | CAGCATGCAGTGGTTTTGTAGC | (SEQ ID NO.: 30) |
| IL-1RA | NM_000877.2 | CCATTGATTCTTGTCCCTCCTT | (SEQ ID NO.: 32) |
| SDF-1 | NM_199168.2 | CCTGAATCCACTTTAGCTTCGG | (SEQ ID NO.: 34) |
| Perlecan | NM_005529 | CCTCGGACACCTCTCGAAACT | (SEQ ID NO.: 36) |
| 18sRNA | AY248756.1 | GCAGCAACTTTAATATACGCTATTGG | (SEQ ID NO.: 38) |

*Fig. 7*
(Continued)

Table 2. Total GAGs and HS did not have any effect toward phenotypic markers of hematopoietic stem cell

| Treatment Group | CD44 | CD90 | CD184 |
|---|---|---|---|
| Control | 99.97% | 3.42% | 9.77% |
| 1ng/mL GAG | 99.92% | 4.37% | 10.62% |
| 10 ng/mL GAG | 100.00% | 3.98% | 10.48% |
| 100 ng/mL GAG | 99.94% | 3.65% | 8.25% |
| 1000 ng/mL GAG | 99.94% | 2.27% | 8.04% |
| 1 ng/mL HS5 | 100.00% | 5.36% | 16.86% |
| 10 ng/mL HS5 | 99.97% | 5.57% | 12.81% |
| 100 ng/mL HS5 | 99.94% | 4.03% | 11.84% |
| 1000 ng/mL HS5 | 99.94% | 2.50% | 8.95% |
| 1000 ng/mL Heparin | 99.94% | 4.16% | 13.23% |

Fig. 8

Table 3. Disaccharide percentage composition of HS5*.

| No. | Disaccharide Standards | % Composition |
|---|---|---|
| 1 | ΔHexUA – GlcN | 22.11 |
| 2 | ΔHexUA-GlcNAc | n.d. |
| 3 | ΔHexUA – GlcN,6S | 38.79 |
| 4 | ΔHexUA,2S – GlcN | n.d. |
| 5 | ΔHexUA – GlcNS | 4.20 |
| 6 | ΔHexUA – GlcNAc,6S | 4.53 |
| 7 | ΔHexUA,2S – GlcNAc | n.d. |
| 8 | ΔHexUA,2S – GlcN,6S | n.d. |
| 9 | ΔHexUA – GlcNS,6S | n.d. |
| 10 | ΔHexUA,2S – GlcNS | n.d. |
| 11 | ΔHexUA,2S – GlcNAc,6S | n.d. |
| 12 | ΔHexUA,2S – GlcNS,6S | n.d. |
| 13 | Unknown | 30.37 | n.d., not detected

*The area under each peak identified in the HPLC analysis was compared with the disaccharide standards to calculate the percentage composition of each disaccharides.

ΔHexUA: uronic acid; GlcN: glucosamine; GlcNAc: N-acetyl-glucosamine; GlcNS: N-sulfated-glucosamine; 6S: 6O-sulfation; 2S: 2O-sulfation.

*Fig. 16*

| | |
|---|---|
| 1 | MVAGTRCLLA LLLPQVLLGG AAGLVPELGR RKFAAASSGR PSSQPSDEVL SEFELRLLSM |
| 61 | FGLKQRPTPS RDAVVPPYML DLYRRHSGQP GSPAPDHRLE RAASRANTVR SFHHEESLEE |
| 121 | LPETSGKTTR RFFFNLSSIP TEEFITSAEL QVFREQMQDA LGNNSSFHHR INIYEIIKPA |
| 181 | TANSKFPVTR LLDTRLVNQN ASRWESFDVT PAVMRWTAQG HANHGFVVEV AHLEEKQGVS |
| 241 | KRHVRISRSL HQDEHSWSQI RPLLVTFGHD GKGHPLHKRE KRQAKHKQRK RLKSSCKRHP |
| 411 | LYVDFSDVGW NDWIVAPPGY HAFYCHGECP FPLADHLNST NHAIVQTLVN SVNSKIPKAC |
| 361 | CVPTELSAIS MLYLDENEKV VLKNYQDMVV EGCGCR (SEQ ID NO.: 2) |

*Fig. 17*

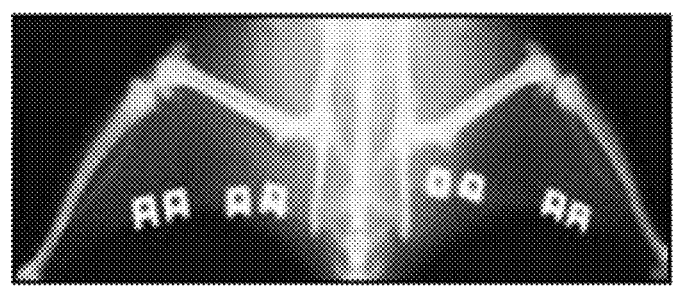
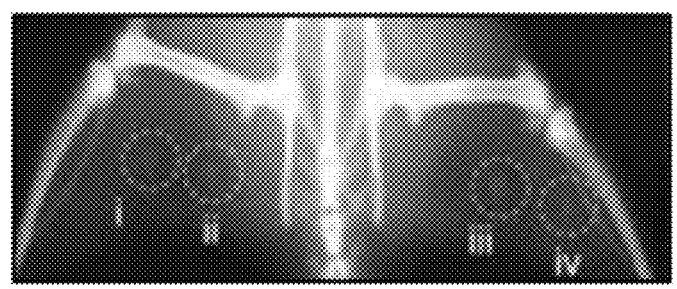
*Fig. 18A*

SEQUENCE LISTING

```
<160> NUMBER OF SEQ ID NOS: 38

<210> SEQ ID NO 1
<211> LENGTH: 22
<212> TYPE: DNA
<213> ORGANISM: Artificial sequence
<220> FEATURE:
<223> OTHER INFORMATION: Synthetic sequence: Forward primer used in PCR

<400> SEQUENCE: 1
cggagcctcc agtctgtcat ta                                            22

<210> SEQ ID NO 2
<211> LENGTH: 396
<212> TYPE: PRT
<213> ORGANISM: Homo sapiens

<400> SEQUENCE: 2
```

```
Met Val Ala Gly Thr Arg Cys Leu Leu Ala Leu Leu Leu Pro Gln Val
 1               5                  10                  15

Leu Leu Gly Gly Ala Ala Gly Leu Val Pro Glu Leu Gly Arg Arg Lys
             20                  25                  30

Phe Ala Ala Ala Ser Ser Gly Arg Pro Ser Ser Gln Pro Ser Asp Glu
             35                  40                  45

Val Leu Ser Glu Phe Glu Leu Arg Leu Leu Ser Met Phe Gly Leu Lys
 50                  55                  60

Gln Arg Pro Thr Pro Ser Arg Asp Ala Val Val Pro Pro Tyr Met Leu
 65                  70                  75                  80

Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
                100                 105                 110

His His Glu Glu Ser Leu Glu Glu Leu Pro Glu Thr Ser Gly Lys Thr
             115                 120                 125

Thr Arg Arg Phe Phe Phe Asn Leu Ser Ser Ile Pro Thr Glu Glu Phe
             130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
                180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
                260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
            290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395
```

<210> SEQ ID NO 3
<211> LENGTH: 22
<212> TYPE: DNA

```
<213> ORGANISM: Artificial sequence
<220> FEATURE:
<223> OTHER INFORMATION: Synthetic sequence: Reverse primer used in PCR

<400> SEQUENCE: 3
aggactcacc cctaaggagt ga                                          22

<210> SEQ ID NO 4
<211> LENGTH: 21
<212> TYPE: DNA
<213> ORGANISM: Artificial sequence
<220> FEATURE:
<223> OTHER INFORMATION: Synthetic sequence: Forward primer used in PCR

<400> SEQUENCE: 4
tccttgttcc actgtgcctt g                                           21

<210> SEQ ID NO 5
<211> LENGTH: 114
<212> TYPE: PRT
<213> ORGANISM: Homo sapiens

<400> SEQUENCE: 5
```

Gln Ala Lys His Lys Gln Arg Lys Arg Leu Lys Ser Ser Cys Lys Arg
 1               5                  10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

```
<210> SEQ ID NO 6
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 6
tgcttccaca tgtcctcaca ac                                          22

<210> SEQ ID NO 7
<211> LENGTH: 21
<212> TYPE: DNA
<213> ORGANISM: Artificial sequence
<220> FEATURE:
<223> OTHER INFORMATION: Synthetic sequence: Forward primer used in PCR

<400> SEQUENCE: 7
aattcggtac atcctcgacg g                                           21

<210> SEQ ID NO 8
<211> LENGTH: 21
<212> TYPE: DNA
```

```
<213> ORGANISM: Artificial sequence
<220> FEATURE:
<223> OTHER INFORMATION: Synthetic sequence: Reverse primer used in PCR

<400> SEQUENCE: 8
ggttgttttc tgccagtgcc t                                                    21

<210> SEQ ID NO 9
<211> LENGTH: 22
<212> TYPE: DNA
<213> ORGANISM: Artificial sequence
<220> FEATURE:
<223> OTHER INFORMATION: Synthetic sequence: Forward primer used in PCR

<400> SEQUENCE: 9
ccaatccata tcaaggacgg tg                                                   22

<210> SEQ ID NO 10
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 10
gctcaaagtc gtctgttgag cc                                                   22

<210> SEQ ID NO 11
<211> LENGTH: 21
<212> TYPE: DNA
<213> ORGANISM: Artificial sequence
<220> FEATURE:
<223> OTHER INFORMATION: Synthetic sequence: Forward primer used in PCR

<400> SEQUENCE: 11
tcccaacagc aagacgagga t                                                    21

<210> SEQ ID NO 12
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 12
caagctaagc cggatgaagc ag                                                   22

<210> SEQ ID NO 13
<211> LENGTH: 22
<212> TYPE: DNA
<213> ORGANISM: Artificial sequence
<220> FEATURE:
<223> OTHER INFORMATION: Synthetic sequence: Forward primer used in PCR

<400> SEQUENCE: 13
cttcgtgact cccatgtcct tc                                                   22

<210> SEQ ID NO 14
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 14
cccaagctaa agtccacagc ag                                                   22
```

<210> SEQ ID NO 15
<211> LENGTH: 22
<212> TYPE: DNA
<213> ORGANISM: Artificial sequence
<220> FEATURE:
<223> OTHER INFORMATION: Synthetic sequence: Forward primer used in PCR

<400> SEQUENCE: 15
gcagctgcag gaactctctt tg                                              22

<210> SEQ ID NO 16
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 16
tgaccttctc cagcaactgg ag                                              22

<210> SEQ ID NO 17
<211> LENGTH: 20
<212> TYPE: DNA
<213> ORGANISM: Artificial sequence
<220> FEATURE:
<223> OTHER INFORMATION: Synthetic sequence: Forward primer used in PCR

<400> SEQUENCE: 17
ctctgcaaaa cccccccaaat                                                20

<210> SEQ ID NO 18
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 18
caactgcgga gaaaggagag aa                                              22

<210> SEQ ID NO 19
<211> LENGTH: 20
<212> TYPE: DNA
<213> ORGANISM: Artificial sequence
<220> FEATURE:
<223> OTHER INFORMATION: Synthetic sequence: Forward primer used in PCR

<400> SEQUENCE: 19
aagatgcaag gcttgctgga                                                 20

<210> SEQ ID NO 20
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 20
agatgttggt ctggacgaag cg                                              22

<210> SEQ ID NO 21
<211> LENGTH: 22
<212> TYPE: DNA
<213> ORGANISM: Artificial sequence
<220> FEATURE:

<223> OTHER INFORMATION: Synthetic sequence: Forward primer used in PCR

<400> SEQUENCE: 21
gcttcctgct caagtgctta ga                                               22

<210> SEQ ID NO 22
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 22
gcacactcac tcaccagctt ct                                               22

<210> SEQ ID NO 23
<211> LENGTH: 22
<212> TYPE: DNA
<213> ORGANISM: Artificial sequence
<220> FEATURE:
<223> OTHER INFORMATION: Synthetic sequence: Forward primer used in PCR

<400> SEQUENCE: 23
aagttctctg gaggatgtgg ct                                               22

<210> SEQ ID NO 24
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 24
tcattcatct cagcagcagt gt                                               22

<210> SEQ ID NO 25
<211> LENGTH: 22
<212> TYPE: DNA
<213> ORGANISM: Artificial sequence
<220> FEATURE:
<223> OTHER INFORMATION: Synthetic sequence: Forward primer used in PCR

<400> SEQUENCE: 25
aaggctgcat ggatcaatct gt                                               22

<210> SEQ ID NO 26
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 26
tcccgttggt tgctactacc ac                                               22

<210> SEQ ID NO 27
<211> LENGTH: 21
<212> TYPE: DNA
<213> ORGANISM: Artificial sequence
<220> FEATURE:
<223> OTHER INFORMATION: Synthetic sequence: Forward primer used in PCR

<400> SEQUENCE: 27
aggcggccag gatataactg a                                                21

-continued

```
<210> SEQ ID NO 28
<211> LENGTH: 21
<212> TYPE: DNA
<213> ORGANISM: Artificial sequence
<220> FEATURE:
<223> OTHER INFORMATION: Synthetic sequence: Reverse primer used in PCR

<400> SEQUENCE: 28
ttctgttccc tttctgccag c                                              21

<210> SEQ ID NO 29
<211> LENGTH: 22
<212> TYPE: DNA
<213> ORGANISM: Artificial sequence
<220> FEATURE:
<223> OTHER INFORMATION: Synthetic sequence: Forward primer used in PCR

<400> SEQUENCE: 29
gaagtccaag agttcgagac cg                                             22

<210> SEQ ID NO 30
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 30
cagcatgcag tggttttgta gc                                             22

<210> SEQ ID NO 31
<211> LENGTH: 21
<212> TYPE: DNA
<213> ORGANISM: Artificial sequence
<220> FEATURE:
<223> OTHER INFORMATION: Synthetic sequence: Forward primer used in PCR

<400> SEQUENCE: 31
acaaaattgg ccagagagtg g                                              21

<210> SEQ ID NO 32
<211> LENGTH: 22
<212> TYPE: DNA
<213> ORGANISM: Artificial sequence
<220> FEATURE:
<223> OTHER INFORMATION: Synthetic sequence: Reverse primer used in PCR

<400> SEQUENCE: 32
ccattgattc ttgtccctcc tt                                             22

<210> SEQ ID NO 33
<211> LENGTH: 21
<212> TYPE: DNA
<213> ORGANISM: Artificial sequence
<220> FEATURE:
<223> OTHER INFORMATION: Synthetic sequence: Forward primer used in PCR

<400> SEQUENCE: 33
gccaacgtca agcatctcaa a                                              21

<210> SEQ ID NO 34
<211> LENGTH: 22
<212> TYPE: DNA
<213> ORGANISM: Artificial sequence
<220> FEATURE:
<223> OTHER INFORMATION: Synthetic sequence: Reverse primer used in PCR
```

```
<400> SEQUENCE: 34
cctgaatcca ctttagcttc gg                                           22

<210> SEQ ID NO 35
<211> LENGTH: 23
<212> TYPE: DNA
<213> ORGANISM: Artificial sequence
<220> FEATURE:
<223> OTHER INFORMATION: Synthetic sequence: Forward primer used in PCR

<400> SEQUENCE: 35
tggacacatt cgtacctttc tga                                          23

<210> SEQ ID NO 36
<211> LENGTH: 21
<212> TYPE: DNA
<213> ORGANISM: Artificial sequence
<220> FEATURE:
<223> OTHER INFORMATION: Synthetic sequence: Reverse primer used in PCR

<400> SEQUENCE: 36
cctcggacac ctctcgaaac t                                            21

<210> SEQ ID NO 37
<211> LENGTH: 20
<212> TYPE: DNA
<213> ORGANISM: Artificial sequence
<220> FEATURE:
<223> OTHER INFORMATION: Synthetic sequence: Forward primer used in PCR

<400> SEQUENCE: 37
ttcgaggccc tgtaattgga                                              20

<210> SEQ ID NO 38
<211> LENGTH: 26
<212> TYPE: DNA
<213> ORGANISM: Artificial sequence
<220> FEATURE:
<223> OTHER INFORMATION: Synthetic sequence: Reverse primer used in PCR

<400> SEQUENCE: 38
gcagcaactt taatatacgc tattgg                                       26
```

HEPARAN SULPHATE

CROSS-REFERENCE TO RELATED APPLICATIONS

The present application claims priority to U.S. Provisional Patent Application No. 61/391,116, filed on Oct. 8, 2010, the entire contents of which are herein incorporated by reference.

FIELD OF THE INVENTION

The present invention relates to heparan sulphate from bone marrow stroma and the use of heparan sulphate from bone marrow stroma in the differentiation and/or lineage commitment of stem cells.

In accordance with 37 CFR 1.52(e)(5), a Sequence Listing in the form of a text file (entitled "Sequence_Listing_ST25.txt," created on Dec. 13, 2011, and 13 kilobytes in size) is incorporated herein by reference in its entirety.

BACKGROUND TO THE INVENTION

Cord blood (CB) hematopoietic stem cell (HSC) transplantation plays a growing role in the treatment of a wide variety of malignant and non-malignant disorders such as leukemia, lymphoma, lymphoproliferative disorders and bone marrow failures (1, 2). Cord blood, as a source of HSCs, widens the pool of potential donors compared to bone marrow and peripheral blood stem cells due to its ease of harvest, availability, less stringent HLA matching criteria and lower graft-versus-host disease. However, despite the advantages, the number of CB HSC transplantations recorded in a 2008 survey in Europe is only 7% of the total allogeneic HSC transplantations (3). This is due to the low number of cells collected per unit of CB that restricts its use to children and lightweight recipients. This cell dose limitation leads to a lower success rate in adult recipients, marked by a delay in engraftment and vulnerability to infectious morbidity (2). In order to address cell dose limitations, differing strategies to expand CB HSCs ex vivo have been proposed. Importantly, ex vivo expansion is geared not only to increase the number of transplanted cells, but the number of lineage committed progenitor cells that can accelerate the engraftment process and reduce the risk of infection. Thus far, only one research group shows a marked improvement in the engraftment rate of ex vivo expanded CB HSC in a phase 1 clinical trial (4).

One of the attempts to improve HSC expansion ex vivo includes the incorporation of stromal components in culture to recreate the hematopoietic microenvironment in which stroma derived extracellular matrix (ECM) and stem cells provide complex molecular cues to support hematopoiesis (5-9). Up to 2 decades ago, it was believed that direct physical contact between HSC and stromal components was required for HSC maintenance (10, 11). However, more recent studies show that stromal cell-derived conditioned media, in which various cytokines and proteoglycans are found, is sufficient to maintain HSCs (7, 12).

Bone morphogenetic protein-2 (BMP-2) has been shown to be efficacious for the treatment of critical-sized bone defects with results comparable to autologous bone graft (35-37). As BMP-2 treatment replaces the need for autologous bone graft, its use is associated with shortened hospital stays for patients (38). However, the high dose of BMP-2 required for a successful therapy carries with it an increased risk of side effects and a greater economic burden for the healthcare system (38). To reduce the efficacious dosage, efforts have focused on improving BMP-2 half-life and/or sustaining and localizing its release (39-43). Heparin has been investigated extensively and shown great promise in this regard. Heparin, a hyper-sulfated glycosaminoglycan (GAG) sugar harvested from mast cell-rich tissues, can bind to and modulate various extracellular molecules including growth factors, adhesion molecules, and receptors (44). Heparin is known to bind to BMP-2 and slow its degradation (44, 45) and inhibition by noggin (45, 46), thereby enhancing its osteoblastic activity. It has also been suggested that heparin prevents BMP-2 from binding to endogenous cell-surface HSPGs, thus enhancing its bioavailability (43). The use of heparin in bone repair has been extended to various types of scaffolds as a means to increase the incorporation of BMP-2 and sustain its delivery in vivo, thereby improving BMP-2 efficacy (39, 41, 47-49).

Despite promising results, the use of heparin to augment BMP-2 therapy may pose unwanted effects due to heparin's affinity for a wide range of proteins. For instance, heparin's binding to antithrombin III is widely used for anticoagulant therapy (50). As the fracture hematoma acts as a reservoir for cytokines and growth factors important for bone repair (51), anticoagulant compounds like heparin may be considered counter-productive. Furthermore, heparin treatment is known to reduce bone density and has been linked to the development of osteoporosis (52, 53) through its pro-osteoclastic actions in vitro (54, 55) and in vivo (53). Indeed, heparin is known to inhibit the interaction between RANKL, a cytokine responsible for the formation and activation of osteoclasts, and its decoy receptor osteoprotegerin (56).

Bone morphogenetic protein 2 (also called bone morphogenic protein 2, BMP2 or BMP-2) is a member of the TGF-β superfamily strongly implicated in the development of bone and cartilage. It is an osteogenic protein, i.e. is a potent inducer of osteoblast differentiation (Marie et al. (2002) Regulation of human cranial osteoblast phenotype by FGF-2, FGFR-2 and BMP-2 signaling". Histol. Histopathol. 17 (3): 877-85). Implantation of collagen sponges impregnated with BMP2 has been shown to induce new bone formation (Geiger M, Li R H, Friess W (November 2003). Collagen sponges for bone regeneration with rhBMP-2. *Adv. Drug Deliv. Rev.* 55 (12): 1613-29.). Recombinant human BMP2 is available for orthopaedic use in USA (e.g. INFUSE® Bone Graft, Medtronic Inc, USA).

SUMMARY OF THE INVENTION

The present invention concerns a heparan sulphate preparation, heparan sulphate isolated or obtained from bone marrow stroma. In one embodiment the heparan sulphate is HS5.

Heparan sulphate from bone marrow stroma has been found to enhance the lineage-commitment of hematopoietic stem cells and enhance BMP-2 induced osteogenesis.

In one aspect of the present invention heparan sulphate from bone marrow stroma is provided. Heparan sulphate from bone marrow stroma may be provided in isolated form or in substantially purified form. This may comprise providing a composition in which the heparan sulphate component is at least 80% heparan sulphate from bone marrow stroma, more preferably one of at least 85%, 90%, 95%, 96%, 97%, 98%, 99% or 100%.

Accordingly, isolated heparan sulphate HS5 is provided, and heparan sulphate isolated from bone marrow stroma is provided.

Heparan sulphates according to the present invention may be isolated or obtained from human or mammalian bone marrow stroma.

Heparan sulphates according to the present invention may have the following heparan lyase disaccharide digestion profile:

| Disaccharide | % Composition |
| --- | --- |
| ΔHexUA - GlcN | 22.11 ± 10% |
| ΔHexUA - GlcN,6S | 38.79 ± 10% |
| ΔHexUA - GlcNS | 4.20 ± 10% |
| ΔHexUA - GlcNAc,6s | 4.53 ± 10% |
| Other | 30.37 ± 10% 10% |

In some preferred embodiments the percentage composition of these disaccharides may be within one of ±one of 9%, 8%, 7%, 6%, 5%, 4%, 3%, 2%, or 1% of the values shown for each disaccharide. The digestion profile is preferably obtained by complete digestion of the heparan sulphate with heparan lyases, more preferably with heparitinases I, and/or II and/or III, and most preferably with heparitinases I, and II or heparitinases I, II and III.

In one aspect of the present invention a method of increasing the number of committed clonogenic cells in a population of hematopoietic stem cells (HSCs) is provided, the method comprising culturing HSCs in vitro in the presence of isolated heparan sulphate HS5 or heparan sulphate isolated from bone marrow stroma.

The method may comprise increasing the number of myeloid lineage-committed progenitor cells. The method may comprise increasing the number of colony forming cells (CFC). The method may comprise increasing the number of burst forming unit-erythroid (BFU-E). The method may comprise increasing the number of colony forming unit-granulocyte macrophage (CFU-GM). The initial HSC population in the culture may comprise at least 50% CD34+ cells, more preferably one of 60%, 70%, 75%, 80%, 85%, 90% or 95% CD34+ cells. The HSC population may be obtained from cord blood. The concentration of heparan sulphate in or added to the culture media may be 500 ng/ml or less, or one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, or 5 ng/ml or less.

In one aspect of the present invention myeloid lineage-committed progenitor cells obtained by in vitro culture of hematopoietic stem cells (HSCs) in the presence of heparan sulphate from bone marrow strome are provided.

In another aspect of the present invention a method of promoting or enhancing osteogenesis is provided, the method comprising administering heparan sulphate from bone marrow stroma to osteoprogenitor cells. The method may be a method of promoting or enhancing BMP-2 induced osteogenesis. The method may comprise contacting the osteoprogenitor cells with heparan sulphate from bone marrow stroma in vitro or in vivo. The osteoprogenitor cells may also be contacted with BMP2 protein, e.g. simultaneously with said heparan sulphate. The osteoprogenitor cells may be mesenchymal stem cells, osteoblast cells, myoblast cells or other bone stem cells or bone precursor cells.

In another aspect of the present invention bone tissue obtained by in vitro culture of osteoprogenitor cells in the presence of heparan sulphate from bone marrow stroma is provided. The bone tissue may be obtained through culture of the osteoprogenitor cells in the presence of BMP2 protein.

In another aspect of the present invention a method of culturing osteoprogenitor cells is provided, the method comprising culturing osteoprogenitor cells in contact with heparan sulphate from bone marrow stroma.

In another aspect of the present invention culture media comprising heparan sulphate from bone marrow stroma is provided.

In another aspect of the present invention the use of heparan sulphate from bone marrow stroma in cell culture in vitro is provided.

In another aspect of the present invention a kit is provided comprising a predetermined amount of heparan sulphate from bone marrow stroma and a predetermined amount of BMP2 protein.

In another aspect of the present invention a pharmaceutical composition or medicament is provided comprising heparan sulphate from bone marrow stroma.

In another aspect of the present invention a composition or pharmaceutical composition is provided comprising heparan sulphate from bone marrow stroma and BMP2 protein.

In another aspect of the present invention heparan sulphate from bone marrow stroma or a composition or pharmaceutical composition comprising said heparan sulphate is provided for use in a method of medical treatment. The use of heparan sulphate from bone marrow stroma for the manufacture of a pharmaceutical composition or medicament for the treatment of disease or repair/replacement/regeneration of cells or tissue in a patient is also provided.

In one embodiment the method of medical treatment may comprise administration of the heparan sulphate or composition or pharmaceutical composition to a patient receiving HSC transplantation. The heparan sulphate or composition or pharmaceutical composition may be administered to the patient in combination with transplanted HSCs.

In another embodiment the method of medical treatment comprises a method of wound healing in vivo. The method of medical treatment may comprise repair and/or regeneration of bone and/or treatment of bone fracture.

A method of transplanting hematopoietic stem cells (HSCs) to a patient in need thereof is provided, the method comprising transplanting a therapeutically effective amount of HSCs to the patient and administering a therapeutically effective amount of heparan sulphate from bone marrow stroma to the site of transplantation of the HSCs in the patient or to tissue that surrounds, is near to, or adjacent to the site of transplantation. The site of transplantation may be bone marrow. The HSCs and heparan sulphate may be administered in combination with the HSCs, or separately.

In another aspect of the present invention products containing therapeutically effective amounts of:
(i) heparan sulphate from bone marrow stroma; and
(ii) hematopoietic stem cells (HSCs),
for simultaneous, separate or sequential use in a method of medical treatment are provided.

In another aspect of the present invention a biocompatible implant or prosthesis comprising a biomaterial and heparan sulphate from bone marrow stroma is provided. The implant or prosthesis may be coated or impregnated with said heparan sulphate. The implant or prosthesis may be further coated or impregnated with BMP2 protein and/or with osteoprogenitor cells.

In another aspect of the present invention a method of forming a biocompatible implant or prosthesis is provided, the method comprising the step of coating or impregnating a biomaterial with heparan sulphate from bone marrow stroma. The method may comprise coating or impregnating the biomaterial with one or both of BMP2 protein and osteoprogenitor cells.

In another aspect of the present invention a method of treating a bone fracture in a patient is provided, the method comprising administration of a therapeutically effective amount of heparan sulphate from bone marrow stroma to the patient. The method may comprise administering said heparan sulphate to tissue surrounding the fracture. Administration of said heparan sulphate may comprise injection of the heparan sulphate to the tissue surrounding the fracture. The heparan sulphate may be formulated as a pharmaceutical composition or medicament comprising the heparan sulphate and a pharmaceutically acceptable carrier, adjuvant or diluent. The method may further comprise administering BMP2 protein to the patient. Said heparan sulphate and BMP2 protein may be formulated as a pharmaceutical composition comprising the heparan sulphate and BMP2 protein and a pharmaceutically acceptable carrier, adjuvant or diluent.

In another aspect of the present invention a method of treating a bone fracture in a patient is provided, the method comprising surgically implanting a biocompatible implant or prosthesis, which implant or prosthesis comprises a biomaterial and a therapeutically effective amount of heparan sulphate from bone marrow stroma into tissue of the patient at or surrounding the site of fracture. The implant or prosthesis may be coated or impregnated with said heparan sulphate. The implant or prosthesis may be further coated or impregnated with one or both of BMP2 protein and osteoprogenitor cells.

In another aspect of the present invention products containing therapeutically effective amounts of:
(i) heparan sulphate from bone marrow stroma; and one or both of
(ii) BMP2 protein;
(iii) osteoprogenitor cells,
for simultaneous, separate or sequential use in a method of medical treatment are provided.

In another aspect of the present invention a method for the repair, replacement or regeneration of cells or tissue in a human or animal patient in need of such treatment is provided, the method comprising:
(i) culturing stem cells in vitro in contact with heparan sulphate from bone marrow stroma for a period of time sufficient for some or all of said cells to differentiate or become lineage-committed;
(ii) collecting said differentiated or lineage-committed cells;
(iii) implanting said differentiated or lineage-committed cells into the body of the patient at a site of injury or disease to repair, replace or regenerate cells or tissue in the patient.

The stem cells may be osteoprogenitor cells, e.g. mesenchymal stem cells, osteoblast cells, myoblast cells or other bone stem cells or bone precursor cells, or hematopoietic stem cells. The method may further comprise contacting the stem cells in culture with exogenous BMP2 protein.

DESCRIPTION OF PREFERRED EMBODIMENTS

Heparan Sulphate from Bone Marrow Stroma

The present invention relates to heparan sulphate obtained and/or isolated from bone marrow stroma. A heparan sulphate has been isolated by the inventors from human bone marrow stroma and is herein referred to as HS5.

Heparan sulphates of the present invention are obtainable by methods of isolating heparan sulphate from bone marrow stroma.

The present invention also relates to mixtures of compounds enriched with HS5, and methods of using such mixtures.

Heparan sulphate from bone marrow stroma may be used in the differentiation of stem cells, which may involve the commitment of stem cells to a certain lineage.

Heparan sulphate from bone marrow stroma has been characterized based on: 1) disaccharide composition and BMP-2 interactions, 2) BMP-2 potentiating effects compared to commercially available heparin and HSs and 3) the mechanisms responsible for enhancing BMP-2 activity. The inventors have shown that like heparin, this HS variant has the ability to bind and stabilize BMP-2 and prevent BMP-2-noggin interactions, yet had little effect on blood coagulation.

Heparan sulphate from bone marrow stroma; particularly HS5, has been shown to have the potential to substitute heparin's function as a vehicle that introduces BMP-2 at a more physiological concentration and in a sustained manner.

We demonstrate that HS originating from a bone marrow stromal cell line better augments BMP-2-induced osteogenesis compared to heparin and HS originating from porcine intestinal mucosa and bovine kidney. The addition of heparin or HS5 enhanced BMP-2 activity mainly by increasing its bioavailability.

In comparison to HS5, heparin was found to generate a negative effect toward terminal osteogenic differentiation and possesses strong anticoagulant activity, while HS5 does not. Thus, heparin may not only prevent bone mineralization but also prevent the coagulation process that is an important initial step in wound repair.

In addition to being obtainable by the methodology described here, HS/BMP2 can also be defined functionally and structurally.

Functionally, HS5 is capable of:
binding BMP-2 protein,
dose-dependently enhancing BMP-2-induced ALP activity in C2C12 cells,
enhancing BMP-2-induced osteocalcin mRNA expression in C2C12 cells,
enhancing BMP-2 induced mineralization in C2C12 cells,
prolonging BMP-2 stability, e.g. in vitro,
prolonging BMP-2 biological activity as indicated by its ability to induce Smad 1/5/8 phosphorylation (p-Smad 1/5/8) in C2C12 cells,
reducing the inhibitory effect of noggin toward BMP-2 activity through disrupting their interaction in C2C12 cells,
producing minimal anticoagulant activity compared with heparin.

Preferably, HS5 binds BMP2 protein with a $K_D$ of less than 500 µM, more preferably less than one of 100 µM, 50 µM, 40 µM, 30 µM, 20 µM, or 10 µM. Binding between HS5 and BMP2 protein may be determined by the following assay method.

BMP2 is dissolved in Blocking Solution (0.2% gelatin in SAB) at a concentration of 3 µg/ml and a dilution series from 0-3 µg/ml in Blocking Solution is established. Dispensing of 200 µl of each dilution of BMP2 into triplicate wells of Heparin/GAG Binding Plates pre-coated with heparin; incubated for 2 hrs at 37° C., washed carefully three times with SAB and 200 µl of 250 ng/ml biotinylated anti-BMP2 added in Blocking Solution. Incubation for one hour at 37° C., wash carefully three times with SAB, 200 µl of 220 ng/ml ExtrAvidin-AP added in Blocking Solution, Incubation for 30 mins at 37° C., careful washing three times with SAB and tap to remove residual liquid, 200 µl of Development Reagent (SigmaFAST p-Nitrophenyl phosphate) added. Incubate at room temperature for 40 minutes with absorbance reading at 405 nm within one hour.

In this assay, binding may be determined by measuring absorbance and may be determined relative to controls such as BMP2 protein in the absence of added heparan sulphate, or BMP2 protein to which an heparan sulphate is added that does not bind BMP2 protein.

Heparan sulphates according to the present invention preferably enhance BMP2 induced Alkaline Phoshatase (ALP) activity in cells of the mouse myoblast cell line C2C12 to a greater extent than the enhancement obtained by addition of corresponding amounts of BMP2 protein, or Heparin alone, or porcine kidney heparan sulphate alone or bovine lung heparan sulphate alone.

Enhancement of ALP activity can be measured by performing the following ALP Assay. C2C12 cells are plated at 20,000 cells/cm$^2$ in a 24-well plate in DMEM (e.g. Sigma-Aldrich Inc., St. Louis, Mo.) containing 10% FCS (e.g. Lonza Group Ltd., Switzerland) and antibiotics (1% Penicillin and 1% Streptomycin) (e.g. Sigma-Aldrich Inc., St. Louis, Mo.) at 37° C./5% $CO_2$. After 24 hours, the culture media is switched to 5% FCS low serum media containing different combinations of 100 ng/mL BMP2 (e.g. R&D Systems, Minneapolis, Minn.), 3 mg/mL control HS or heparin and varying concentrations of heparan sulphate isolated from bone marrow stroma. Cell lysis is carried out after 3 days using RIPA buffer containing 1% Triton X-100, 150 mM NaCl, 10 mM Tris pH 7.4, 2 mM EDTA, 0.5% Igepal (NP40), 0.1% Sodium dodecyl sulphate (SDS) and 1% Protease Inhibitor Cocktail Set III (Calbiochem, Germany). The protein content of the cell lysate is determined by using BCA protein assay kit (Pierce Chemical Co., Rockford, Ill.). ALP activity in the cell lysates is then determined by incubating the cell lysates with p-nitrophenylphosphate substrate (Invitrogen, Carlsbad, Calif.). The reading is normalized to total protein amount and presented as relative amount to the group containing BMP2 treatment alone.

Enhancement of ALP activity in C2C12 cells can also be followed by immunohistochemical techniques, such as the following ALP staining protocol. ALP Staining: C2C12 cells are cultured as described in the assay methodology immediately above. After 3 days of treatment, the cell layer is washed in PBS and stained using Leukocyte Alkaline Phosphatase Kit (e.g. Sigma-Aldrich Inc., St. Louis, Mo.) according to manufacturer's specification. The cell layer is fixed in citrate buffered 60% acetone and stained in alkaline-dye mixture containing Naphthol AS-MX Phosphatase Alkaline and diazonium salt. Nuclear staining is performed using Mayer's Hematoxylin solution.

These techniques can be used to identify heparan sulphate from bone marrow stroma as a heparan sulphate that enhances a greater degree of BMP2 protein induced ALP activity in C2C12 cells compared with non-specific heparan sulphates, e.g. porcine kidney heparan sulphate or bovine lung heparan sulphate.

Heparan sulphate from bone marrow stroma according to the present invention may also prolong the effects of BMP2 signalling to levels that equal or exceed those of heparin. This can be assessed by the following assay. C2C12 cells are exposed to (i) nothing, (ii) BMP2 alone, (iii) BMP2+ Heparin or (iv) BMP2+ heparan sulphate from bone marrow stroma for 72 hours and the phosphorylation levels of the BMP2-specific intracellular signaling molecule Smad1/5/8 are monitored by immunoblotting (e.g. see FIG. 11B).

A functional property of heparan sulphate from bone marrow stroma is its ability to enhance the process of bone repair, particularly in mammalian subjects. This may be tested in a bone repair model in which the speed and quality of bone repair in control animals (e.g. animals not given HS or animals given a control HS such as porcine kidney heparan sulphate or bovine lung heparan sulphate) and animals treated with heparan sulphate from bone marrow stroma is compared. Speed and quality of bone repair may be assessed by analysing generation of bone volume at the wound site over time, e.g. by X-ray and microCT imaging analysis of the wound.

Structurally, the isolated HS5 was found to be heterogeneous in molecular weight with three predominant molecular weight components of approximately 7.5, 29 and 75 kDa (FIG. 3). As such, the heparan sulphate may be a mixture of the three molecular weight components. The molecular weight of HS5 was distributed at 7.5, 29 and 75 kDa and the major disaccharide units were uronic acids linked to non-sulfated glucosamines or 6-O sulfated glucosamines (Table. 1). The identity of a large portion of the disaccharide units could not be determined due to the current lack of standards for all possible combinations of variably sulfated disaccharide units. Heparan sulphate according to the present invention may comprise one, two or three components, which may have an approximate molecular weight of ±10% (more preferably ±one of 9%, 8%, 7%, 6%, 5%, 4%, 3%, 2%, or 1%) of the respective molecular weights indicated above.

The disaccharide composition of isolated HS5 following complete digestion with heparitinases I, II and III is shown in FIG. 16. Isolated HS5 was found to be composed of 22.11% of non-sulfated, 38.79% of 6-O-sulfated, 4.20% of N-sulfated and 4.53% of 6-O-sulfated/N-deacetylated disaccharide units, while the remaining disaccharide composition is at present unknown. Heparan sulphates according to the present invention include heparan sulphates that have a disaccharide composition within ±10% (more preferably ±one of 9%, 8%, 7%, 6%, 5%, 4%, 3%, 2%, or 1%) of the values shown for each disaccharide in FIG. 16 in the column titled "% Composition" (optionally excluding those indicated as n.d.—not detected, and/or optionally excluding those indicated as Unknown).

Heparan sulphates are glycosaminoglycans (GAGs). GAGs may be extracted from a tissue or cell sample or extract by a series of routine separation steps (e.g. anion exchange chromatography), well known to those of skill in the art.

GAG mixtures may contain a mixture of different types of glycosaminoglycan, which may include dextran sulphates, chondroitin sulphates and heparan sulphates. A heparan sulphate-enriched GAG fraction may be obtained by performing column chromatography on the GAG mixture, e.g. weak, medium or strong anion exchange chromatography, as well as strong high pressure liquid chromatography (SAX-HPLC), with selection of the appropriate fraction.

The collected GAGs may be subjected to further analysis in order to identify the GAG, e.g. determine GAG composition or sequence, or determine structural characteristics of the GAG. GAG structure is typically highly complex, and, taking account of currently available analytical techniques, exact determinations of GAG sequence structure are not possible in most cases.

However, the collected GAG molecules may be subjected to partial or complete saccharide digestion (e.g. chemically by nitrous acid or enzymatically with lyases such as heparinase I, and/or heparinase II and optionally heparinase III) to yield saccharide fragments that are both characteristic and diagnostic of the heparan sulphate. In particular, digestion to yield disaccharides (or tetrasaccharides) may be used to measure the percentage of each disaccharide obtained which will provide a characteristic disaccharide "fingerprint" of the heparan sulphate.

The pattern of sulphation of the heparan sulphate can also be determined and used to determine structure. For example, the pattern of sulphation at amino sugars and at the C2, C3 and C6 positions may be used to characterise a heparan sulphate.

Disaccharide analysis, tetrasaccharide analysis and analysis of sulphation can be used in conjunction with other analytical techniques such as HPLC, mass spectrometry, NMR and surface plasmon resonance which can each provide unique spectra for the GAG. In combination, these techniques may provide a definitive structural characterisation of the GAG.

Heparan sulphates isolated by enrichment may be pure, i.e. contain substantially only one type of Heparan sulphate, or may continue to be a mixture of different types of GAG(s) and/or Heparan sulphate(s), the mixture having a higher proportion of particular GAGs (preferably heparan sulphates).

The functional effect may be to promote (stimulate) or inhibit the proliferation of the cells of a certain type or the differentiation of one cell type into another, or the expression of one or more protein markers. For example, the heparan sulphate may promote cell proliferation, i.e. an increase in cell number, or promote differentiation of cells (e.g. stem cells) into specialised cell types (e.g. mesenchymal stem cells into connective tissue, bone precursor or bone stem cells towards bone), promote or inhibit the expression of protein markers indicative of the multipotency or differentiation state of the cells (e.g. markers such as alkaline phosphatase activity, detection of RUNX2, osterix, collagen I, II, IV, VII, X, osteopontin, Osteocalcin, BSPII, SOX9, Aggrecan, ALBP, CCAAT/enhancer binding protein-α (C/EBPα), adipocyte lipid binding protein (ALBP), alkaline phosphatase (ALP), bone sialoprotein 2, (BSPII), Collagen2a1 (Coll2a) and SOX9). In another example the functional effect may be to promote or enhance differentiation of cells towards a particular lineage. In some embodiments the functional effect is to increase the number of clonogenic cells in a population of hematopoietic stem cells (HSCs). In some embodiments the functional effect is to promote differentiation towards myeloid lineage-committed progenitor cells, e.g. towards burst forming unit-erythroid (BFU-E) or colony forming unit-granulocyte macrophage (CFU-GM) colonies.

As used herein, the term 'modulating effect' is understood to mean the effect that a first entity has on a second entity wherein the second entity's normal function in another process or processes is modified by the presence of the first entity. The modulating effect may be either agonistic or antagonistic.

The modulating effect may be a potentiating effect. The term 'potentiating effect' is understood to mean the effect of increasing potency. In a preferred embodiment of the present invention, the term 'potentiating effect' refers to the effect that a first entity has on a second entity, which effect increases the potency of that second entity in another process or processes. In a further preferred embodiment of the present invention, the potentiating effect is understood to mean the effect of isolated GAGs on a heparin-binding factor, wherein the said effect increases the potency of said heparin-binding factor.

The potentiating effect may be an increase in bioavailability of a heparin-binding factor. In a preferred embodiment of the present invention, the potentiating effect is an increase in bioavailability of BMP2. One method of measuring an increase in bioavailability of the heparin-binding factor is through determining an increase in local concentration of the heparin-binding factor.

The potentiating effect may be to protect the heparin-binding factor from degradation. In an especially preferred embodiment of the present invention, the potentiating effect is to protect BMP-2 from degradation. One method of determining a decrease in the degradation of the heparin-binding factor is through measuring an increase in the half-life of the heparin-binding factor.

The potentiating effect may be to sequester heparin-binding factors away from cellular receptors or may be to stabilise the ligand-receptor interaction.

The potentiating effect (e.g. modulation of growth or differentiation) may be determined by use of appropriate assays. For example, the effect that a heparan sulphate has on the stability of BMP-2 may be determined by ELISA. The effect that a heparan sulphate has on the activity of BMP-2 may be determined by measuring the activation/expression of one or more of SMAD 1, 5 or 8, or measuring the expression of one or more osteogenic marker genes such as Runx2, alkaline phosphatase, Osterix, Osteocalcin and BSP1, or measuring the levels of mineralization using staining such as Alizarin Red and von Kossa.

The promotion or enhancement of differentiation of cells towards a particular lineage may also be determined by use of appropriate assays. For example, the effect that a heparan sulphate has on the number of clonogenic cells in a population of hematopoietic stem cells (HSCs) may be determined by measuring the number of colony forming cells in the population following culture in the contact with the heparan sulphate. In some embodiments the number of myeloid lineage-committed progenitor cells, e.g. burst forming unit-erythroid (BFU-E) or colony forming unit-granulocyte macrophage (CFU-GM), may be measured.

As used herein, the process of 'contacting' involves the bringing into close physical proximity of two or more discrete entities. The process of 'contacting' involves the bringing into close proximity of two or more discrete entities for a time, and under conditions, sufficient to allow a portion of those two or more discrete entities to interact on a molecular level. Preferably, as used herein, the process of 'contacting' involves the bringing into close proximity of the mixture of compounds possessing one or more GAGs and the polypeptide corresponding to the heparin-binding domain of a heparin-binding factor. Examples of 'contacting' processes include mixing, dissolving, swelling, washing.

Heparan sulphates according to the present invention may be useful in a range of applications, in vitro and/or in vivo. The heparan sulphates may be provided for use in stimulation or inhibition of cell or tissue growth and/or proliferation and/or differentiation and/or lineage commitment of cells or tissue in either cell or tissue culture in vitro, or in cells or tissue in vivo.

The heparan sulphates may be provided as a formulation for such purposes. For example, culture media may be provided comprising a heparan sulphate from bone marrow stroma.

Cells or tissues obtained from in vitro cell or tissue culture in the presence of heparan sulphate from bone marrow stroma may be collected and implanted into a human or animal patient in need of treatment. A method of implantation of cells and/or tissues may therefore be provided, the method comprising the steps of:
   (a) culturing cells and/or tissues in vitro in contact with heparan sulphate from bone marrow stroma;
   (b) collecting the cells and/or tissues;
   (c) implanting the cells and/or tissues into a human or animal subject in need of treatment.

The cells may be cultured in part (a) in contact with heparan sulphate from bone marrow stroma for a period of time sufficient to allow growth, proliferation, differentiation or lineage commitment of the cells or tissues. For example, the period of time may be chosen from: at least 5 days, at least 10 days, at least 20 days, at least 30 days or at least 40 days.

In another embodiment the heparan sulphate from bone marrow stroma may be formulated for use in a method of medical treatment, including the prevention or treatment of injury or disease. A pharmaceutical composition or medicament may be provided comprising heparan sulphate from bone marrow stroma and a pharmaceutically acceptable diluent, carrier or adjuvant. Such pharmaceutical compositions or medicaments may be provided for the prevention or treatment of injury or disease. The use of heparan sulphate from bone marrow stroma in the manufacture of a medicament for the prevention or treatment of injury or disease is also provided. Optionally, pharmaceutical compositions and medicaments according to the present invention may also contain BMP-2 protein. In further embodiments the pharmaceutical compositions and medicaments may further comprise cells, e.g. stem cells, mesenchymal stem cells, bone precursor cells or bone stem cells.

In some embodiments treatment of injury or disease may involve transplantation of hematopoietic stem cells (HSCs) into a patient. Such transplantation may be useful as part of a treatment of a disease of the blood, bone marrow or lymphatic system. Heparan sulphate from bone marrow stroma may be used to expand the number of committed clonogenic cells in a population of HSCs, and the HSC population so obtained may then be transplanted into the patient. The transplanted cells may be optionally combined with heparan sulphate from bone marrow stroma.

In some embodiments, HSCs that have not been pre-treated with heparan sulphate from bone marrow stroma so as to expand the number of committed clonogenic cells in the HSC population may be transplanted to the patient together with heparan sulphate from bone marrow stroma so that expansion of the number of committed clonogenic cells takes place in situ in the patient.

Treatment of injury or disease may comprise the repair, regeneration or replacement of cells or tissue, such as connective tissue (e.g. bone, cartilage, muscle, fat, tendon or ligament). For the repair of tissue, the pharmaceutical composition or medicament comprising heparan sulphate from bone marrow stroma may be administered directly to the site of injury or disease in order to stimulate the growth, proliferation and/or differentiation of new tissue to effect a repair of the injury or to cure or alleviate (e.g. provide relief to the symptoms of) the disease condition. The repair or regeneration of the tissue may be improved by combining cells (e.g. stem cells, mesenchymal stem cells, bone precursor cells or bone stem cells) in the pharmaceutical composition or medicament.

For the replacement of tissue, heparan sulphate from bone marrow stroma may be contacted with cells and/or tissue during in vitro culture of the cells and/or tissue in order to generate cells and/or tissue for implantation at the site of injury or disease in the patient. Implantation of cells or tissue can be used to effect a repair of the injured or diseased tissue in the patient by replacement of the injured or diseased tissue. This may involve excision of injured/diseased tissue and implantation of new tissue prepared by culture of cells and/or tissue in contact with heparan sulphate from bone marrow stroma.

Pharmaceutical compositions and medicaments according to the present invention may therefore comprise one of:
(a) heparan sulphate from bone marrow stroma;
(b) heparan sulphate from bone marrow stroma in combination with cells (e.g. stem cells, hematopoietic stem cells, mesenchymal stem cells, osteoprogenitor cells);
(c) heparan sulphate from bone marrow stroma in combination with BMP-2 protein;
(d) HS/BMP2 in combination with cells (e.g. stem cells, hematopoietic stem cells, mesenchymal stem cells, osteoprogenitor cells) and BMP-2 protein;
(e) Tissues or cells obtained from culture of cells or tissues in contact with heparan sulphate from bone marrow stroma.

The use of heparan sulphate from bone marrow stroma in the repair, regeneration or replacement of tissue may involve use in wound healing, e.g. acceleration of wound healing, healing of scar or bone tissue and tissue grafting.

In another aspect, the present invention provides a biological scaffold comprising heparan sulphate from bone marrow stroma. In some embodiments, the biological scaffolds of the present invention may be used in orthopaedic, vascular, prosthetic, skin and corneal applications. The biological scaffolds provided by the present invention include extended-release drug delivery devices, tissue valves, tissue valve leaflets, drug-eluting stents, vascular grafts, wound healing or skin grafts and orthopaedic prostheses such as bone, ligament, tendon, cartilage and muscle.

In another aspect, the present invention provides pharmaceutically acceptable formulations comprising a mixture of compounds comprising one or more GAGs, said mixture being enriched with respect to heparan sulphate from bone marrow stroma.

In another aspect of the present invention a kit is provided for use in the repair, or regeneration of tissue, said kit comprising (i) a predetermined amount of heparan sulphate from bone marrow stroma, and (ii) a predetermined amount of BMP-2 protein.

The heparan sulphates of the present invention can be administered to a subject as a pharmaceutically acceptable salt thereof. For example, base salts of the heparan sulphates of the present invention include, but are not limited to, those formed with pharmaceutically acceptable cations, such as sodium, potassium, lithium, calcium, magnesium, ammonium and alkylammonium. The present invention includes within its scope cationic salts, for example the sodium or potassium salts.

It will be appreciated that heparan sulphates of the present invention which bear a carboxylic acid group may be delivered in the form of an administrable prodrug, wherein the acid moiety is esterified (to have the form —$CO_2R'$). The term "pro-drug" specifically relates to the conversion of the —OR' group to a —OH group, or carboxylate anion therefrom, in vivo. Accordingly, the prodrugs of the present invention may act to enhance drug adsorption and/or drug delivery into cells. The in vivo conversion of the prodrug may be facilitated either by cellular enzymes such as lipases and esterases or by chemical cleavage such as in vivo ester hydrolysis.

Medicaments and pharmaceutical compositions according to aspects of the present invention may be formulated for administration by a number of routes, including but not limited to, injection at the site of disease or injury. The medicaments and compositions may be formulated in fluid or solid form. Fluid formulations may be formulated for administration by injection to a selected region of the human or animal body.

Administration is preferably in a "therapeutically effective amount", this being sufficient to show benefit to the individual. The actual amount administered, and rate and time-course of administration, will depend on the nature and severity of the injury or disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

In this specification a patient to be treated may be any animal or human. The patient may be a non-human mammal, but is more preferably a human patient. The patient may be male or female.

Methods according to the present invention may be performed in vitro or in vivo, as indicated. The term "in vitro" is intended to encompass procedures with cells in culture whereas the term "in vivo" is intended to encompass procedures with intact multi-cellular organisms.

Stem Cells

Heparan sulphate from bone marrow stroma may be used in the differentiation of stem cells, and/or the lineage-commitment of stem cells.

The stem cells cultured and described herein may be stem cells of any kind. They may be totipotent or multipotent (pluripotent). They may be embryonic or adult stem cells from any tissue and may be hematopoietic stem cells, neural stem cells or mesenchymal stem cells. Preferably they are adult stem cells.

In this specification, by stem cell is meant any cell type that has the ability to divide (i.e. self-renew) and remain totipotent or multipotent (pluripotent) and give rise to specialized cells.

Stem cells cultured in the present invention may be obtained or derived from existing cultures or directly from any adult, embryonic or fetal tissue, including blood, bone marrow, skin, epithelia or umbilical cord (a tissue that is normally discarded).

The multipotency of stem cells may be determined by use of suitable assays. Such assays may comprise detecting one or more markers of pluripotency, e.g. alkaline phosphatase activity, detection of RUNX2, osterix, collagen I, II, IV, VII, X, osteopontin, Osteocalcin, BSPII, SOX9, Aggrecan, ALBP, CCAAT/enhancer binding protein-α (C/EBPα), adipocyte lipid binding protein (ALBP), alkaline phosphatase (ALP), bone sialoprotein 2, (BSPII), Collagen2a1 (Col2a) and SOX9.

In some preferred embodiments the stem cells are hematopoietic stem cells (HSCs), e.g. capable of differentiation to cells of the blood, including cells of the myeloid lineage (e.g. monocytes and macrophages, neutrophils, basophils, eosinophils, erythrocytes, megakaryocytes/platelets, dendritic cells) and cells of the lymphoid lineage (e.g. T-cells, B-cells, NK-cells).

HSCs are easily obtainable from bone marrow of adult mammals by minimally invasive techniques and can be expanded in culture and permitted to differentiate into the desired lineage. HSCs may also be obtained from umbilical cord blood and placenta (being tissues that are normally discarded). Preferred HSC populations may be human and may contain at least 50% CD34+ cells, optionally following purification or enrichment for such cells. In more preferred embodiments HSC populations have at least one of 60%, 70%, 75%, 80%, 85%, 90% or 95% CD34+ cells.

In accordance with the present invention, lineage commitment of HSCs may be promoted or enhanced by contact with heparan sulphate from bone marrow stroma. Commitment may involve formation of colony forming units, which, for example, may comprise formation of one or more of: Colony-forming unit erythrocyte (CFU-E), Colony-forming unit granulo-monocyte (CFU-GM), Colony-forming unit megakaryocyte (CFU-Me), Colony-forming unit Basophil (CFU-B), Colony-forming unit Eosinophil (CFU-Eo). Commitment may be to the myeloid-lineage.

In some preferred embodiments the stem cells are mesenchymal stem cells (MSCs), e.g. capable of differentiation into connective tissue and/or bone cells such as chondrocytes, osteoblasts, myocytes and adipocytes.

Mesenchymal stem cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Mesenchymal stem cells can be isolated and detected using selective markers, such as STRO-I, from a CD34+ fraction indicating their potential for marrow repopulation. These cell surface markers are only found on the cell surface of mesenchymal stem cells and are an indication of the cells pluripotency.

Suitable mesenchymal stem cells may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES *British Journal of Haematology* 121(2):368-374, April 2003.) or Wharton's Jelly of the umbilical cord (e.g. Ta et al. Long-term Expansion and Pluripotent Marker Array Analysis of Wharton's Jelly-Derived Mesenchymal Stem Cells. *Stem Cells Dev.* 2009 Jul. 20 (Epub)).

Mesenchymal stem cells may be obtained by differentiation of pluripotent stem cells, such as human embryonic stem cells or induced pluripotent stem cells, by application of suitable differentiating factors, as is well known in the art.

Mesenchymal stem cells or human bone marrow stromal stem cells are pluripotent (multipotent) progenitor cells with the ability to generate components of cartilage, bone, muscle, tendon, ligament, fat and blood. These primitive progenitors exist postnatally and exhibit stem cell characteristics, namely low incidence and extensive renewal potential. These properties in combination with their developmental plasticity have generated tremendous interest in their potential use to replace damaged tissues. In essence these stem cells could be cultured to expand their numbers then transplanted to the injured site or after seeding in/on scaffolds to generate appropriate tissue constructs.

Thus, an alternative approach for skeletal, muscular, tendon, ligament and blood repair/regeneration is the selection, expansion and modulation of the appropriate progenitor cells such as osteoprogenitor cells (e.g. mesenchymal stem cells, chondrocytes, osteoblasts, myoblasts, bone stem cells or bone precursor cells) in the case of bone in combination with a conductive or inductive scaffolds to support and guide regeneration together with judicious selection of specific tissue growth factors.

The stem cells may be obtained from any animal or human, e.g. non-human animals, e.g. rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian animals; and/or human. Preferably they are human. Optionally they are non-human. Optionally they are non-embryonic stem cells. Optionally they are not totipotent.

In yet a further aspect of the present invention, a pharmaceutical composition comprising stem cells or other cells generated by any of the methods of the present invention, or fragments or products thereof, is provided. The pharmaceutical composition may be useful in a method of medical treatment. Suitable pharmaceutical compositions may further comprise a pharmaceutically acceptable carrier, adjuvant or diluent.

In another aspect of the present invention, stem cells or other cells generated by any of the methods of the present invention may be used in a method of medical treatment, preferably, a method of medical treatment is provided comprising administering to an individual in need of treatment a therapeutically effective amount of said medicament or pharmaceutical composition.

Stem cells and other cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

Glycosaminglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof. Examples of GAGs are chondroitin sulfate, keratan sulfate, heparin, dermatan sulfate, hyaluronate and heparan sulfate.

As used herein, the term 'GAG' also extends to encompass those molecules that are GAG conjugates. An example of a GAG conjugate is a proteoglycosaminoglycan (PGAG, proteoglycan) wherein a peptide component is covalently bound to an oligosaccharide component.

Heparan Sulphate (HS)

Heparan sulfate proteoglycans (HSPGs) represent a highly diverse subgroup of proteoglycans and are composed of heparan sulfate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O—, 6-O— and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1->4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity.

As shown in Brickman et al, 1998, Glycobiology 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerization of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerization in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography.

Transplantation of Cells

Some aspects of the present invention are concerned with the manipulation of populations of hematopoietic stem cells (HSCs) for the purpose of transplanting HSCs, optionally together with other associated cells, e.g. other cord blood cells, into donor patients.

Hematopoietic stem cell transplantation provides a means of treatment of a wide variety of malignant and non-malignant disorders, such as leukemia, lymphoma, lymphoproliferative disorders and bone marrow failures.

As such cells obtained by culture and/or expansion of HSCs in the presence of heparan sulphate from bone marrow may be used for transplantation into a patient for the treatment of diseases of the blood, such as cancers of the blood or bone marrow (leukemia), bone marrow or lymphatic system.

Leukemia's that may be treated include acute myelogenous leukemia and chronic myelogenous leukemia.

Cells may be prepared for transplantation by ex vivo (e.g. in vitro) culture of an HSC population in the presence of heparan sulphate from bone marrow stroma such that the number of committed clonogenic cells in the population is increased. Cells so obtained may be transplanted directly into a patient, e.g. into the bone marrow. Optionally they may be combined with unmanipulated HSCs, e.g. cord blood cells, prior to transplant. This may increase the total number of nucleated cells transplanted and/or balance the early engraftment that is anticipated from the more committed expanded cells with longer term immune reconstitution that may be provided by more primitive cells present in the unmanipulated cell population.

The transplanted cells may be administered in combination with heparan sulphate from bone marrow stroma. By "in combination" is meant separate, sequential or simultaneous administration of the cells and heparan sulphate from bone marrow stroma. Administration of the heparan sulphate may be to tissue that surrounds, is near to, or adjacent to the site of transplantation.

Accordingly, heparan sulphate from bone marrow stroma and pharmaceutical compositions and medicaments comprising heparan sulphate from bone marrow stroma are provided for use in a method of treatment of diseases of the blood, bone marrow or lymphatic system in a human or mammalian subject.

The treatment may involve repair, regeneration and growth of new cells of the blood (of any type, e.g. erythrocytes, macrophages).

Medicaments and pharmaceutical compositions according to the present invention may be formulated for administration by a number of routes. Most preferably heparan sulphate from bone marrow stroma is formulated in fluid or liquid form for injection.

In some embodiments the heparan sulphate from bone marrow stroma is formulated as a controlled release formulation, e.g. in a drug capsule for implantation. The heparan sulphate from bone marrow stroma may be attached to, impregnated on or soaked into a carrier material (e.g. a biomaterial) such as nanofibers or biodegradable paper or textile.

Administration is preferably in a "therapeutically effective amount", this being sufficient to treat diseases of the blood, bone marrow or lymphatic system. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the disease, the condition of the individual patient, the site of delivery, the method of administration and other factors known to practitioners. Single or multiple administrations of heparan sulphate from bone marrow stroma doses may be administered in accordance with the guidance of the prescribing medical practitioner. Purely by way of example, heparan sulphate from bone marrow stroma may be delivered in dosages of at least 1 ng/ml, more preferably at least 5 ng/ml and optionally 10 ng/ml or more. Individual heparan sulphate from bone marrow stroma dosages may be of the order less than 1 mg and greater than 1 μg, e.g. one of about 5 μg, about 10 μg, about 25 μg, about 30 μg, about 50 μg, about 100 μg, about 0.5 mg, or about 1 mg. Examples of the techniques and protocols mentioned above can be found in Remington's Pharmaceutical Sciences, 20th Edition, 2000, pub. Lippincott, Williams & Wilkins.

Bone Fracture

In some aspects the present invention is concerned with the therapeutic use (human and veterinary) of heparan sulphate from bone marrow stroma to treat bone fracture. Heparan sulphate from bone marrow stroma is reported here to augment wound healing in bone. Heparan sulphate from bone marrow stroma stimulates bone regeneration following injury and contributes to improved wound healing in bone. Heparan sulphate from bone marrow stroma provides improvements in the speed of bone fracture repair enabling a reduction in the recovery time from injury.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralization) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using heparan sulphate from bone marrow stroma include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using heparan sulphate from bone marrow stroma include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using heparan sulphate from bone marrow stroma also include those of the head (skull) and neck, including those of the face such as the jaw, nose and cheek. In this respect, in some preferred embodiments heparan sulphate from bone marrow stroma may be used to assist in repair or regeneration of bone during dental or facial or cranial surgery, which may include reconstruction of bones (as distinct from teeth) of the face and/or mouth, e.g. including the jawbone.

Bone fracture also includes pathological porosity, such as that exhibited by subjects with osteoporosis.

Although not limiting to the present invention, the primary actions of heparan sulphate from bone marrow stroma may be on cells within, adjacent to, or caused to migrate into the wound site and may be on the bone stem cells, the preosteoblasts or the osteoblasts, or on any of the ancillary or vasculogenic cells found or caused to migrate into or within the wound bed.

Heparan sulphate from bone marrow stroma and pharmaceutical compositions and medicaments comprising heparan sulphate from bone marrow stroma are provided for use in a method of treatment of bone fracture in a mammalian subject.

Treatment may comprise wound healing in bone. The treatment may involve repair, regeneration and growth of bone. Heparan sulphate from bone marrow stroma facilitates fracture repair by facilitating new bone growth. Heparan sulphate from bone marrow stroma acts to improve the speed of fracture repair enabling bone healing to occur faster leading to improved recovery time from injury. Treatment may lead to improved bone strength.

Treatment may also include treatment of osteoporosis or osteoarthritis.

Administration of heparan sulphate from bone marrow stroma is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. Most preferably heparan sulphate from bone marrow stroma is formulated in fluid or liquid form for injection.

In some embodiments the heparan sulphate from bone marrow stroma is formulated as a controlled release formulation, e.g. in a drug capsule for implantation at the wound site. The heparan sulphate from bone marrow stroma may be attached to, impregnated on or soaked into a carrier material (e.g. a biomaterial) such as nanofibers or biodegradable paper or textile.

Pharmaceutical compositions, medicaments, implants and prostheses comprising heparan sulphate from bone marrow stroma may also comprise BMP2. Owing to the ability of heparan sulphate from bone marrow stroma to bind BMP2, the heparan sulphate from bone marrow stroma may act as a carrier of BMP2 assisting in delivery of BMP2 to the wound site and maintenance of BMP2 stability.

Administration is preferably in a "therapeutically effective amount", this being sufficient to improve healing of the bone fracture compared to a corresponding untreated fracture. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of heparan sulphate from bone marrow stroma doses may be administered in accordance with the guidance of the prescribing medical practitioner. Purely by way of example, heparan sulphate from bone marrow stroma may be delivered in dosages of at least 1 ng/ml, more preferably at least 5 ng/ml and optionally 10 ng/ml or more. Individual heparan sulphate from bone marrow stroma dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

Heparan sulphate from bone marrow stroma may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required heparan sulphate from bone marrow stroma may be administered directly to (e.g. applied to) the fracture during the surgical procedure.

Biomaterials

Pharmaceutical compositions and medicaments of the invention may take the form of a biomaterial that is coated and/or impregnated with heparan sulphate from bone marrow stroma. An implant or prosthesis may be formed from the biomaterial. Such implants or prostheses may be surgically implanted to assist in transplantion of cells, bone growth, tissue regeneration, tissue restructuring and/or tissue re-modelling.

Heparan sulphate from bone marrow stroma may be applied to implants or prostheses to accelerate new tissue formation at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with heparan sulphate from bone marrow stroma. Impregnation may comprise forming the biomaterial by mixing heparan sulphate from bone marrow stroma with the constitutive components of the biomaterial, e.g. during polymerisation, or absorbing heparan sulphate from bone marrow stroma into the biomaterial. Coating may comprise adsorbing the heparan sulphate from bone marrow stroma onto the surface of the biomaterial.

The biomaterial should allow the coated or impregnated heparan sulphate from bone marrow stroma to be released from the biomaterial when administered to or implanted in the subject. Biomaterial release kinetics may be altered by altering the structure, e.g. porosity, of the biomaterial.

In addition to coating or impregnating a biomaterial with heparan sulphate from bone marrow stroma, one or more biologically active molecules may be impregnated or coated on the biomaterial. For example, at least one chosen from the group consisting of: BMP-2, BMP-4, OP-1, FGF-1, FGF-2, TGF-β1, TGF-β2, TGF-β3; VEGF; collagen; laminin; fibronectin; vitronectin. In addition or alternatively to the above bioactive molecules, one or more bisphosphonates may be impregnated or coated onto the biomaterial along with heparan sulphate from bone marrow stroma. Examples of useful bisphosphonates may include at least one chosen from the group consisting of: etidronate; clodronate; alendronate; pamidronate; risedronate; zoledronate.

Biomaterials coated or impregnated with heparan sulphate from bone marrow stroma may be useful in both medical and veterinary purposes. It will be appreciated that the present invention may improve the quality of life of a patient or potentially extend the life of an animal, for example a valuable racehorse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a crosslinked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), polyp lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices.* 2006; 3(1): 29-47; Wong C, Inman E, Spaethe R, Helgerson S. *Thromb. Haemost.* 2003 89(3): 573-582; Pandit A S, Wilson D J, Feldman D S. Fibrin scaffold as an effective vehicle for the delivery of acidic growth factor (FGF-1). *J. Biomaterials Applications.* 2000; 14(3); 229-242; DeBlois Cote M F. Doillon C J. Heparin-fibroblast growth factor fibrin complex: in vitro and in vivo applications to collagen based materials. *Biomaterials.* 1994; 15(9): 665-672.).

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

One example of a biomaterial suitable for use in combination with HS/BMP2 is the JAX™ bone void filler (Smith & Nephew). Jax granules are composed of high purity calcium sulfate and retain their shape to provide a scaffold with controlled, inter-granular porosity and granule migration stability. Jax granules dissolve safely and completely in the body.

Other suitable biomaterials include ceramic or metal (e.g. titanium), hydroxyapatite, tricalcium phosphate, demineralised bone matrix (DBM), autografts (i.e. grafts derived from the patient's tissue), or allografts (grafts derived from the tissue of an animal that is not the patient). Biomaterials may be synthetic (e.g. metal, fibrin, ceramic) or biological (e.g. carrier materials made from animal tissue, e.g. non-human mammals (e.g. cow, pig), or human).

The biomaterial can be supplemented with additional cells. For example, one can "seed" the biomaterial (or co-synthesise it) with undifferentiated bone precursor cells, e.g. stem cells such as mesenchymal stem cells, more preferably human mesenchymal stem cells.

The subject to be treated may be any animal or human. The subject is preferably mammalian, more preferably human. The subject may be a non-human mammal (e.g. rabbit, guinea pig, rat, mouse or other rodent (including cells from any animal in the order Rodentia), cat, dog, pig, sheep, goat, cattle (including cows, e.g. dairy cows, or any animal in the order Bos), horse (including any animal in the order Equidae), donkey, and non-human primate). The non-human mammal may be a domestic pet, or animal kept for commercial purposes, e.g. a race horse, or farming livestock such as pigs, sheep or cattle. The subject may be male or female. The subject may be a patient.

Culture Media

Culture media comprising heparan sulphate from bone marrow stroma may be of any kind but is preferably liquid or gel and may contain other nutrients and growth factors (e.g. FGF-2). Culture media may be prepared in dried form, e.g. powdered form, for reconstitution in to liquid or gel. Heparan sulphate from bone marrow stroma will preferably be present in non-trace amounts. For example, the concentration of heparan sulphate from bone marrow stroma in the culture media may range between about 1 ng/ml culture media to about 1000 ng/ml culture media. Preferably, the concentration of heparan sulphate from bone marrow stroma in the culture media is about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, or 5 ng/ml or less.

Dosages of Heparan Sulphate

In both in vitro and in vivo uses, heparan sulphate from bone marrow stroma may be used in concentrations or dosages of about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, pr 1 mg or less.

BMP2 Protein

In this specification BMP2 refers to Bone morphogenetic protein 2 (also called bone morphogenic protein 2, BMP2 or BMP-2), which is a member of the TGF-β superfamily and is implicated in the development of bone and cartilage.

The amino acid sequence of BMP2 preprotein from *Homo sapiens* (SEQ ID NO:2) is shown in FIG. 17. Amino acids 1 to 23 represent the signal peptide, and amino acids 24 to 396 represent the amino acid sequence of the proprotein. The amino acid sequence of the mature protein is given as SEQ ID NO:5 herein.

In this specification "BMP2 protein" includes proteins having at least 70%, more preferably one of 75%, 80%, 85%, 90%, 95%, 96%, 97%, 98%, 99% or 100% sequence identity with the amino acid sequence of the BMP2 preprotein or BMP2 proprotein illustrated in FIG. 17 or with the amino acid sequence of the mature BMP2 protein of SEQ ID NO:5.

Reference to BMP2 protein preferably includes the BMP-2 protein described in Ruppert et al (Eur J. Biochem 1996).

The BMP2 protein is preferably osteogenic, i.e. has the activity of inducing, or assisting in the induction of, osteoblast differentiation.

The BMP2 protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 7. List of primers used in PCR (Table 1).

FIG. 8. Total GAGs and HS did not have any effect toward phenotypic markers of hematopoietic stem cell (Table 2).

FIG. 16. Disaccharide percentage composition of HS5 (Table 3) obtained from complete digestion of HS5 with heparan lysases. *The area under each peak identified in the HPLC analysis was compared with the disaccharide standards to calculate the percentage composition of each disaccharide. ΔHexUA: uronic acid; GlcN: glucosamine; GlcNAc: Nacetyl-glucosamine; GlcNS: N-sulfated-glucosamine; 6S: 6O-sulfation; 2S: 2O-sulfation. n.d., not detected.

FIG. 17. Amino acid sequence of bone morphogenetic protein 2 preprotein from Homo sapiens, NCBI Accession No. NP_001191 (NP_001191.1 GI:4557369) (SEQ ID NO:2).

DETAILED DESCRIPTION OF THE INVENTION

Figure 1:
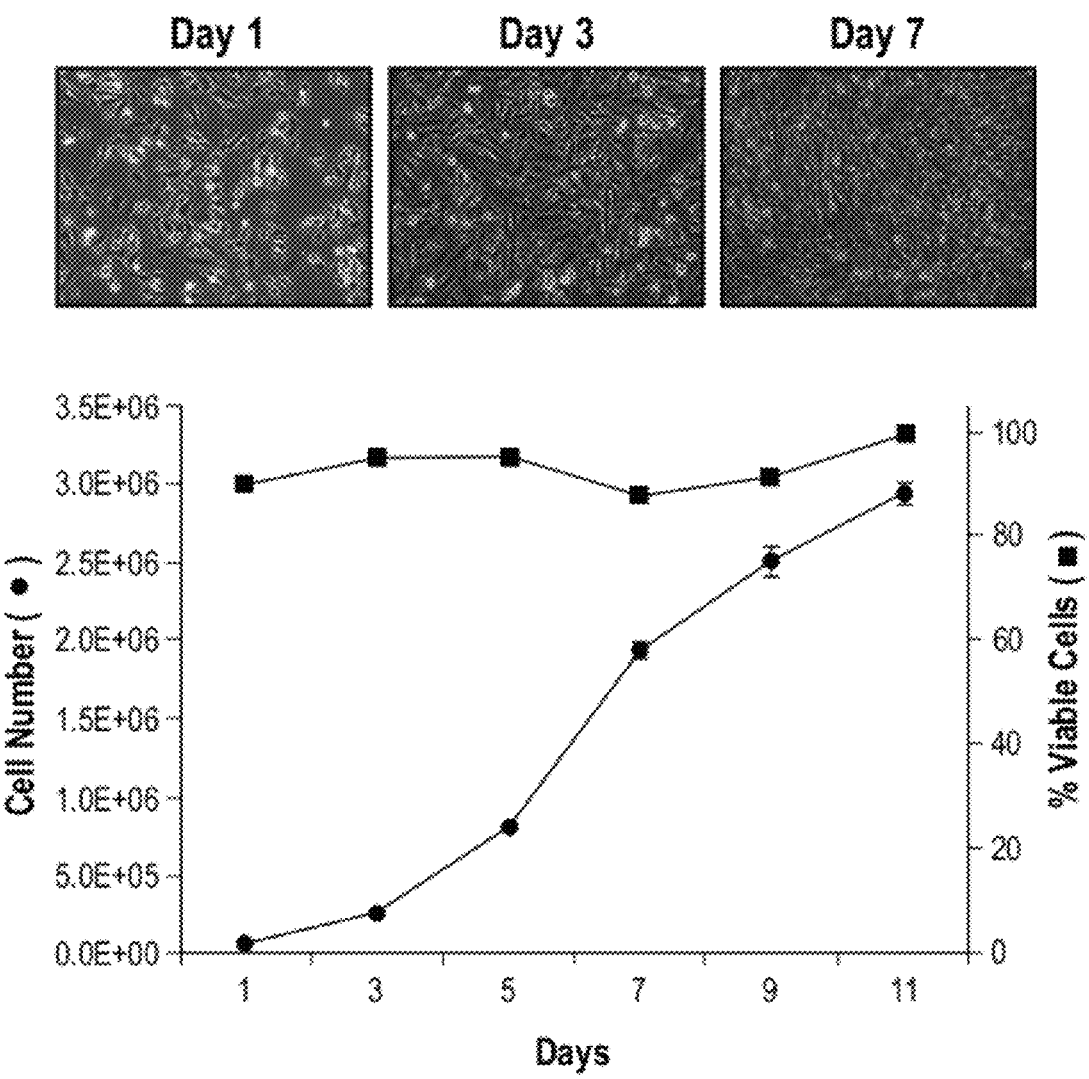
FIG. 1. BMS5 growth analysis. BMS5 seeded at 30,000 cells/cm² continue to expand up to 11 days. Cell viability was maintained above 80% throughout the culture period.

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

Example 1

Isolation and Identification of Human Bone Marrow Derived Heparan Sulphate

The immortalized human bone marrow stromal cell line (HS-5, ATCC CRL-11882), herein referred to as BMS5, was maintained in DMEM, 10% FCS (Lonza Group Ltd.), 100 U/mL penicillin/streptomycin, 4 mM L-glutamine and 1.5 g/L $NaHCO_3$. BMS5 cells were plated at $3\times10^4$ cells/cm$^2$ for all experimental analyses.

BMS5 cells were seeded at $3\times10^4$ cells/cm$^2$ in a 15-cm dish in maintenance media. One day after seeding, the media was replaced with serum free media and the media collected every other day up to day-11 and pooled. At each collection point, the media was centrifuged at 5000 rpm for 10 min at 4° C. and filtered using 0.45 μm filter to remove cell debris prior to storage at 4° C.

The purification of HS from the cell-conditioned media (herein called HS5) and its disaccharide analysis were performed according to the method of Murali S, Manton K J, Tjong V, Su X D, Haupt L M, Cool S M, Nurcombe V 2009 Purification and characterization of heparan sulfate from human primary osteoblasts. Journal of Cellular Biochemistry 108(5):1132-1142, which is briefly reproduced below:

Purification of Total Glycosaminoglycans (TGAG)

Cell culture medium is subjected to ion-exchange chromatography on a UNO Q-Sphere column (15-ml) equilibrated in 50 mM Tris-HCl with 150 mM NaCl, pH 7.4 (low salt buffer) using a low pressure liquid chromatography (Biologic-Duoflow chromatography system from Bio-Rad). The medium is loaded at a flow rate of 2 ml/min and the column washed with the same buffer until the baseline reaches to zero. The bound material is eluted with a linear gradient of 1M NaCl (high salt buffer). The peak fractions are pooled, concentrated and desalted with low salt buffer using an Amicon centrifugal filter (as per manufacturer's instructions) having a molecular mass cut off of 5 kDa. The samples are quantified for the uronic acid content by the carbazole method [Berry D, Shriver Z, Venkataraman G, Sasisekharan R. 2004. Quantitative assessment of FGF regulation by cell surface heparan sulfates. Biochem Biophys Res Commun 314:994-1000] and stored at −20° C.

Isolation of HS GAGs

Concentrated TGAG samples are treated with neuraminidase (0.1 U) for 4 h. Five volumes of 100 mM Tris acetate, pH 8.0, are then added to the sample which is further digested with chondroitinase ABC lyases (0.1 U) for 4 h at 37° C. and further digested overnight with an equal volume of fresh enzyme. Finally, the core protein and the lyases are digested away with pronase (⅕ total volume of 10 mg/ml pronase in 500 mM Tris acetate, 50 mM calcium acetate, pH 8.0) at 37° C. for 24 h. The entire mixture is then diluted 1:10 with low salt buffer, passed through a 15-ml UNO Q-Sphere column and eluted as described previously. The peak fractions are pooled, concentrated and desalted with water using an Amicon centrifugal filter with mass cut off of 5 kDa. The samples are quantified for the uronic acid content by carbazole method [Berry et al., 2004, supra] and stored at −20° C.

Alkali/Borohydride Eliminative Cleavage

Concentrated HS GAGs are treated with 1M sodium borohydride under mild alkaline conditions (0.5M NaOH for 16 h at 48° C.) to remove the GAG chains from the core proteins by β-elimination. After neutralization with glacial acetic acid, concentrated ammonium bicarbonate was added and after the bubbling stopped, samples were analyzed on a Sepharose CL-6B column (1 cm×120 cm) equilibrated in 0.5M $NH_4HCO_3$ to compare the relative size of the protein standards.

Enzymatic Depolymerization of HS Chains

Purified HS samples (100 mg) are dissolved in 100 mM sodium acetate/0.2M calcium acetate, pH 7.0 and incubated with 10 mU/ml of heparinase or heparitinase I in the same buffer at 37° C. for 16 h and then a second aliquot of enzyme added and incubated for a further 4 h. The heparinase or heparitinase I digested HS sample is then passed over a Bio-Gel P-6 column (1 cm×120 cm) equilibrated with 0.25M $NH_4HCO_3$ to compare the relative sizes of the heparin oligosaccharides.

Disaccharide Analysis Using Strong Anion Exchange Chromatography (SAX-HPLC)

Samples (100 mg) were dissolved in 100 mM sodium acetate/0.2M calcium acetate, pH 7.0. Heparinase, heparitinase I and II are all used at a concentration of 10 mU/ml in the same buffer. Each sample is sequentially digested for a recovery of disaccharides for SAXHPLC analysis; for this the samples are digested at 37° C. as follows: heparinase for 2 h, heparitinase I for 1 h, heparitinase II for 18 h, and finally an aliquot of each lyases for 6 h. Samples were run on a BioGel P-2 column (1 cm×120 cm) equilibrated with 0.25M $NH_4HCO_3$. The disaccharide peak is lyophilized and then dissolved in acidified water (pH 3.5 with HCl). This is passed over a ProPac PA-1 SAX-HPLC column (Dionex, USA), attached to a high pressure liquid chromatography system and the HS disaccharides eluted with a linear gradient 0-1.0M NaCl, pH 3.5, over 60 min at a flow-rate of 1 ml/min. Peaks are identified using HS disaccharides standards (Seikagaku, Tokyo, Japan) monitored at $A_{232nm}$.

Figure 3:
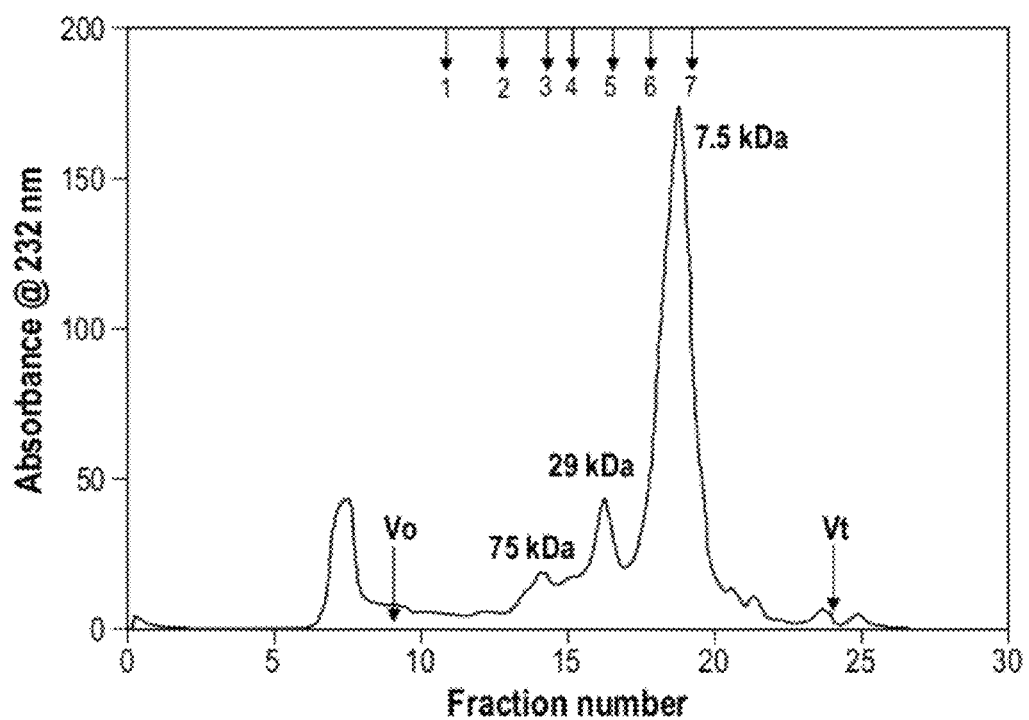
FIG. 3. HS5 molecular weight was distributed at 7.5, 29 and 75 kDa. HS5 weight was assessed using a Superdex 200 column. The column was calibrated using gel filtration high and low molecular weight protein calibration marker-proteins to determine the molecular weight of HS5. Arrow indicates elution position of HMW and LMW protein standards (1. Ferritin; 2. Aldalose; 3. Conalbumin; 4. Ovalbumin; 5. Carbonic Anhydrase; 6. Ribonuclease A; and 7. Aprotin). Vo: void volume; Vt: total volume.

The isolated HS5 is heterogeneous in molecular weight with 3 predominant molecular weights of 7.5, 29 and 75 kDa present (FIG. 3). It is composed of 22.11% of non-sulfated, 38.79% of 6-O-sulfated, 4.20% of N-sulfated and 4.53% of 6-O-sulfated/N-deacetylated disaccharide units, while the remaining is unknown.

Example 2

Effect of Human Bone Marrow Stroma-Derived Heparan Sulphate on the Ex Vivo Expansion of Human Cord Blood Hematopoietic Stem Cells We explored the effect of heparan sulphate (HS) derived from HSC-supportive human bone marrow stromal cells towards the expansion of human cord blood (CB) HSCs and how it compares to the effect of total GAG. We hypothesize that human bone marrow-derived HS, herein referred to as HS5, can better maintain and enhance the proliferation of CB HSC in the presence of hematopoietic cytokines compared to total GAG. Total GAG and HS5 were isolated from the human bone marrow stromal cell line HS-5, herein referred to as BMS5, as this cell line has been shown to support the growth of hematopoietic stem cells both in a co-culture systems and in the presence of its conditioned media (CM) (12). We examined the effect of total GAG or HS5 toward the expansion of human CD34+ CD38− cells, phenotypic marker expression and the formation of myeloid-colony forming cells in the presence of the hematopoietic cytokines; stem cell factor (SCF), FMS-like tyrosine kinase 3 ligand (Flt-3L) and thrombopoietin (TPO). The effect of HS5 toward CB HSC expansion was also compared to heparin derived from porcine mucosa, an HSC non-supportive cell source. Heparin shares identical disaccharide unit building blocks to HS though is more extensively sulphated compared to the latter and hence, binds a greater number of cytokines than does HS. We show that HS at low dose, but neither the total GAG nor heparin, has the ability to increase the number of myeloid lineage-committed progenitor cells despite having no effect towards overall expansion of HSCs and the more primitive, quiescent CD34+ CD38− cell population. Thus, bone marrow-derived HS may have the potential to accelerate engraftment time by facilitating the expansion of committed cells from CB HSCs.

We found that the number of myeloid lineage-committed progenitor cells was increased at low dosage of HS as illustrated by an increase in the total number of colony forming cells (CFC), and erythroid (BFU-E) and myeloid (CFU-GM) colonies. Notably, the stroma-derived HS did not alter the levels of various HSC phenotypic markers after expansion nor was there an increase in the growth of CD34+ HSCs.

This Example shows that HS secreted into solution by stromal cells has the capacity to support hematopoietic cytokines in the maintenance and expansion of HSCs. The incorporation of stromal-derived HS as a reagent may improve the efficacy of cord blood HSC transplantation by enhancing the number of committed cells that accelerate the rate of engraftment.

Methods

Materials

All cell culture reagents were purchased from Sigma-Aldrich (St. Louis, Mo., USA) unless stated otherwise. All fluorescently labeled antibodies against the various cluster of differentiations (CD) investigated and their isotype-matched controls used in FACS analysis were purchased from BD Biosciences (San Jose, Calif., USA). Commercial porcine intestinal mucosa-derived heparin was purchased from Sigma-Aldrich (St. Louis, Mo., USA).

Cell Culture

The immortalized human bone marrow stromal cell line (HS-5, ATCC CRL-11882), herein referred to as BMS5 was maintained in DMEM, 10% FCS (Lonza Group Ltd.), 100 U/mL penicillin/streptomycin, 4 mM L-glutamine and 1.5 g/L $NaHCO_3$. BMS5 cells were plated at $3 \times 10^4$ cells/$cm^2$ for all experimental analyses.

Hematopoietic stem cells were isolated from umbilical cord blood (UCB) units collected from the Singapore Cord Blood Blank (SCBB). Mononuclear cells were isolated from UCB by density gradient centrifugation using Ficoll-Paque Plus. Briefly, UCB was pre-diluted in PBS and gently layered on top of Ficoll. The sample was centrifuged and the interphase layer was collected. The cells were washed with PBS twice before resuspension in PBS (pH 7.2) containing 2 mM EDTA and 0.5% BSA. CD34+ hematopoietic stem cells (HSCs) were isolated from the cell suspension using CD34 MicroBead kit (MiltenyiBiotec, Bergisch Gladbach, Germany) according to manufacturer's specification. Isolated CD34+ HSCs were cultured at $4 \times 10^4$ cells/mL on non-tissue culture treated 24-well plates and expanded for 12 days in QBSF-60 Stem Cell serum-free medium (Quality Biological, Inc., Gaithersburg, Md., USA) supplemented with 50 ng/mL of SCF, Flt3-L and TPO(R&D Systems) in the presence/absence of BMS5-derived total GAG or HS at varying concentrations prior to analysis.

Cell Proliferation Assay

Total and viable cell numbers were counted at specified time points using Guava®Flexreagent and the Guava® PCA-96 benchtop flow cytometer as specified by the manufacturer (Guava Technologies, Hayward, Calif.).

BMS5 Growth Factor Profiling at the Transcript Level

Total RNA was isolated at day-3 and reverse transcribed as previously described (20). The expression of target genes was determined by amplifying the cDNA using custom designed primers (Table 1) with the following reaction setup: 1) activation step: 94° C. for 10 min; 2) amplification step (30 cycles): 94° C. for 45 s, 58° C. for 45 s, 72° C. for 45 s; and 3) final extension step: 72° C. for 7 min.

BMS5 Cytokine Profiling at the Protein Level

The conditioned media was collected at an indicated time and stored at −80° C. prior to quantitation. The amount of cytokines present in the media was assayed using their respective Quantikine ELISA kit (R&D Systems) according to the manufacturer's specification. The values obtained were blanked using basal non-conditioned media.

Total Glycosaminoglycan (GAG) and Heparan Sulfate (HS) Extraction and Purification The BMS5 cells were seeded at $3 \times 10^4$ cells/$cm^2$ in a 15-cm dish in maintenance media. One day after seeding, the media was replaced with serum free media and the media collected every other day up to day-11 and pooled. At each collection point, the media was centrifuged at 5000 rpm for 10 min at 4° C. and filtered using 0.45 µg filter to remove cell debris prior to storage at 4° C. The purification of HS from the cell-conditioned media (herein referred to as HS5) and its disaccharide analysis were performed as previously described (Murali S, Manton K J, Tjong V, Su X D, Haupt L M, Cool S M, Nurcombe V 2009 Purification and characterization of heparan sulfate from human primary osteoblasts. Journal of Cellular Biochemistry 108(5):1132-1142).

Hematopoietic Stem Cell Phenotyping Using FACS Analysis

HSCs were removed from culture after 12 days expansion, washed in PBS and resuspended in FACS buffer (2% FCS and 0.01% $NaN_3$ in PBS) before aliquoting into a 96-well plate at $1 \times 10^5$ cells/well. Cells were pelleted and then incubated with pre-diluted antibodies in ice for 20 minutes. Subsequently, cells were washed twice in FACS buffer before fixing in 4% PFA for 20 minutes at 4° C. Finally, cells were washed twice and resuspended in FACS buffer before analysis on FACS-Calibur (Becton-Dickinson, San Jose, Calif.).

Colony Forming Cell (CFC) Assay

Hematopoietic stem cells colony forming cell assay and colonies classification were performed using Methocult® H4434 Classic (StemCell Technologies Inc, Grenoble, France) according to manufacturer's specification. Briefly, CD34+ HSCs that had been expanded for 12 days were resuspended in Iscove's MDM supplied in the kit with 2% FCS and mixed at a 1:10 (v/v) ratio with Methocult® H4434. The cells were plated at 500 cells per 35 mm dish and incubated at 37° C./5% $CO_2$ for 14-16 days prior to colony counting and classification.

Colonies were classified as burst forming unit-erythroid (BFU-E), a precursor to erythrocytes, and colony forming unit-granulocyte macrophage (CFU-GM), a precursor to granulocytes and macrophages.

Statistical Analysis

Mean differences between samples were analyzed by performing homogeneity of variance test, followed by ANOVA. Differences of $p<0.05$ was considered significant.

Results

Total GAG and HS Collection from BMS5

Figure 2A:
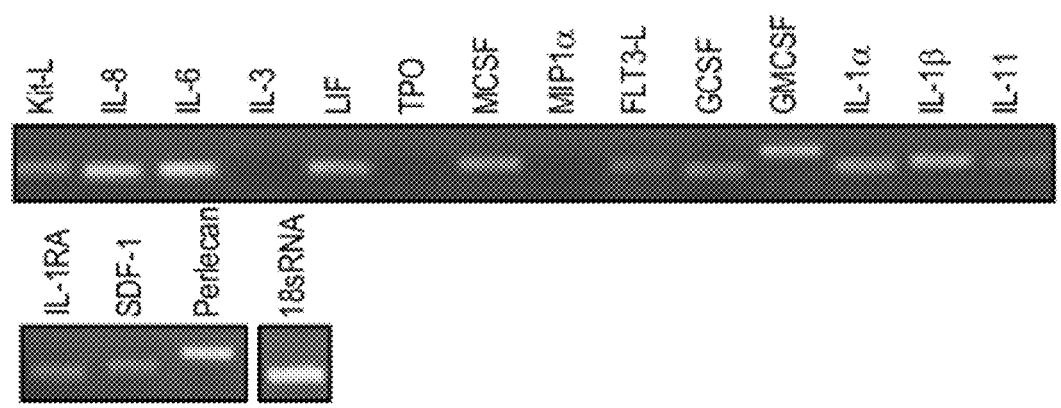
FIG. 2. BMS5 secretes various cytokines and growth factors at the mRNA transcript (A) and protein (B) level at different periods of growth. Cytokines that support hematopoietic stem cell expansion and maintenance were secreted as early as day 3 in culture.
Figure 2B:
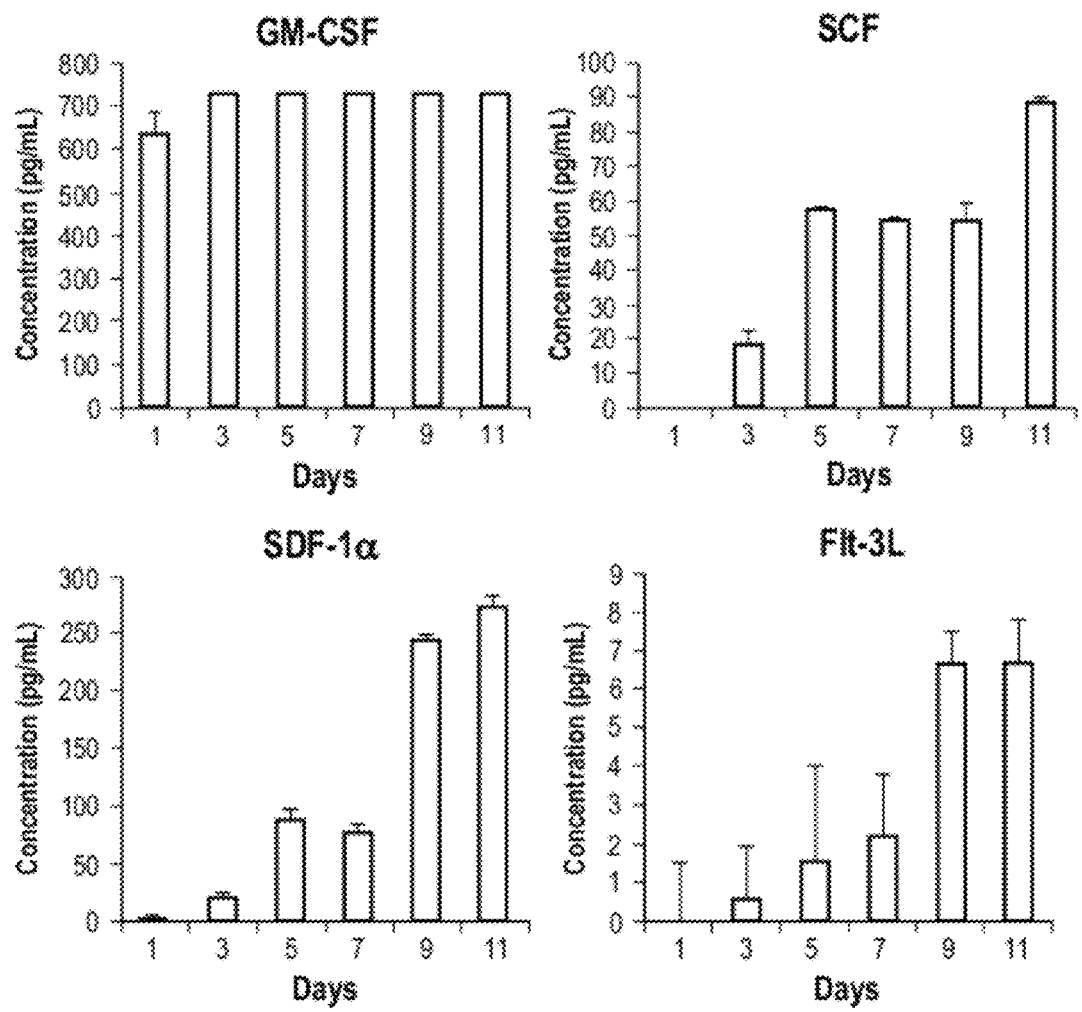

In order to determine the appropriate time point for GAG collection, BMS5 was cultured for up to 11 days where proliferation, viability and cytokine production were monitored. BMS5 continued to replicate after reaching 100% confluency around day 7 and its viability was maintained above 85% throughout the culture period (FIG. 1). At the transcript level, BMS5 was found to express various types of cytokines that are involved in HSC maintenance and expansion (FIG. 2). The protein production of some of the cytokines that were used to support HSC culture in this study was expressed as early as day 1 in BMS5 (FIG. 2). Based on the protein synthesis profile, we believe that BMS5 would express GAGs that support the activity of these cytokines as early as day 1 as well. Coincidentally, the soluble form of HS, perlecan, was abundantly synthesized at the transcript level by BMS5 at day 3 (FIG. 2).

Thus, total GAG, likely containing a mixture of HS, chondroitin sulfate and dermatan sulphate was isolated from BMS5 conditioned media at alternating days from day 1 to 11. Heparan sulfate (HS5) was purified from the total GAG mixture in order to determine whether this GAG species alone can influence cytokine activity to enhance HSC expansion. The isolated HS5 is heterogeneous in molecular weight with 3 predominant molecular weights of 7.5, 29 and 75 kDa present (FIG. 3). It is composed of 22.11% of non-sulfated, 38.79% of 6-O-sulfated, 4.20% of N-sulfated and 4.53% of 6-O-sulfated/N-deacetylated disaccharide units, while the remaining is unknown.

Isolation and Purification of CD34+ Hematopoietic Progenitor Cells

Figure 4:
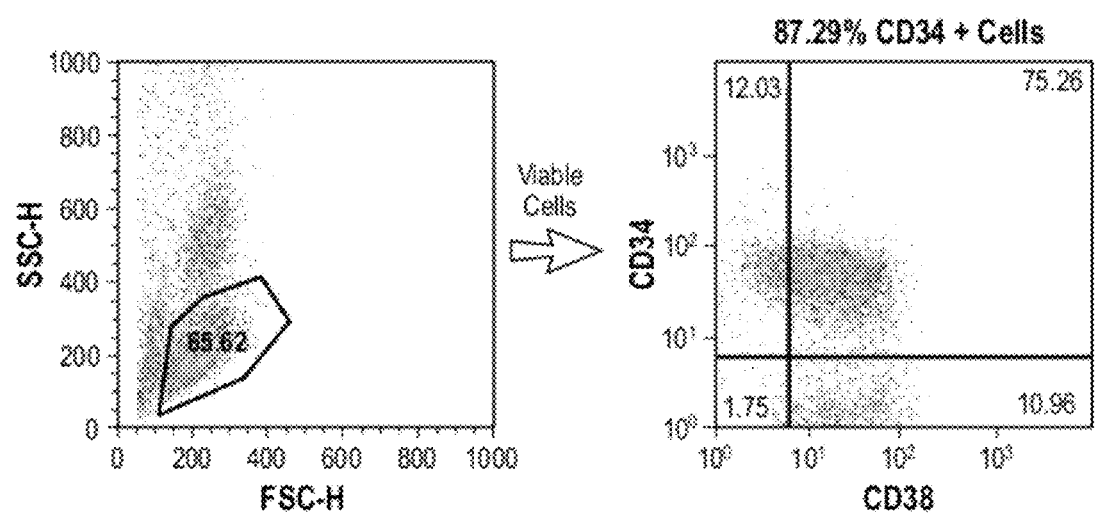
FIG. 4. Hematopoietic progenitors were isolated from umbilical cord blood using a CD34+ progenitor cell isolation kit at a purity>80%.
Figure 5A:
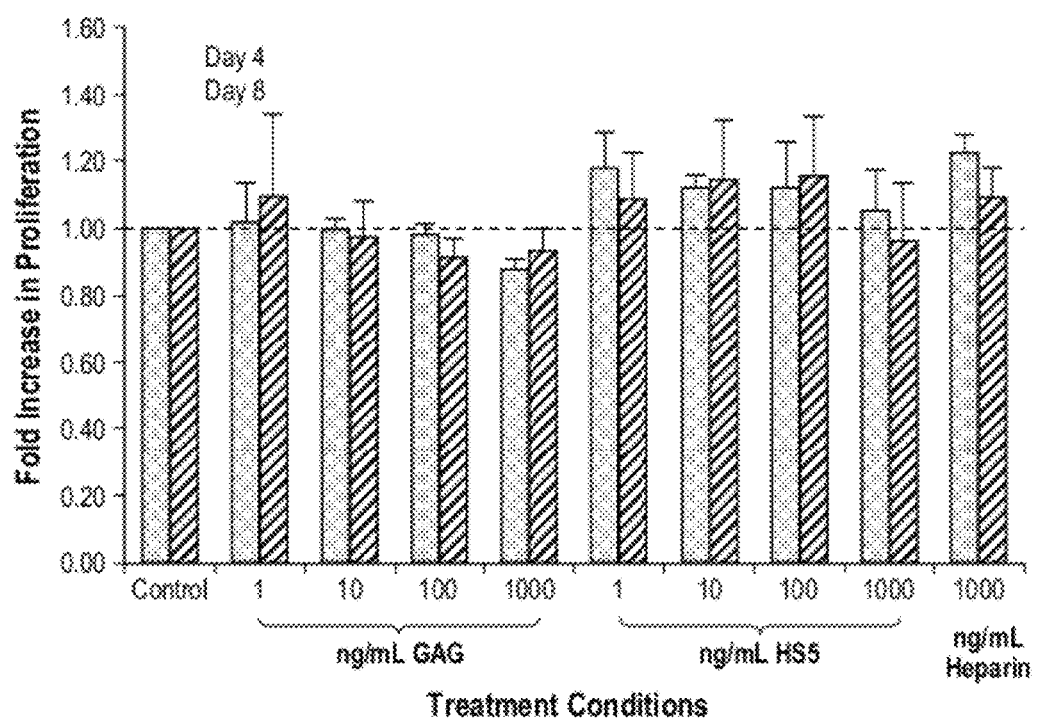
FIG. 5. HS5 and total GAG has no effect on hematopoietic stem cell expansion (A) nor the total number of CD34+ CD38− cells (B) after 12 days culture.
Figure 5B:
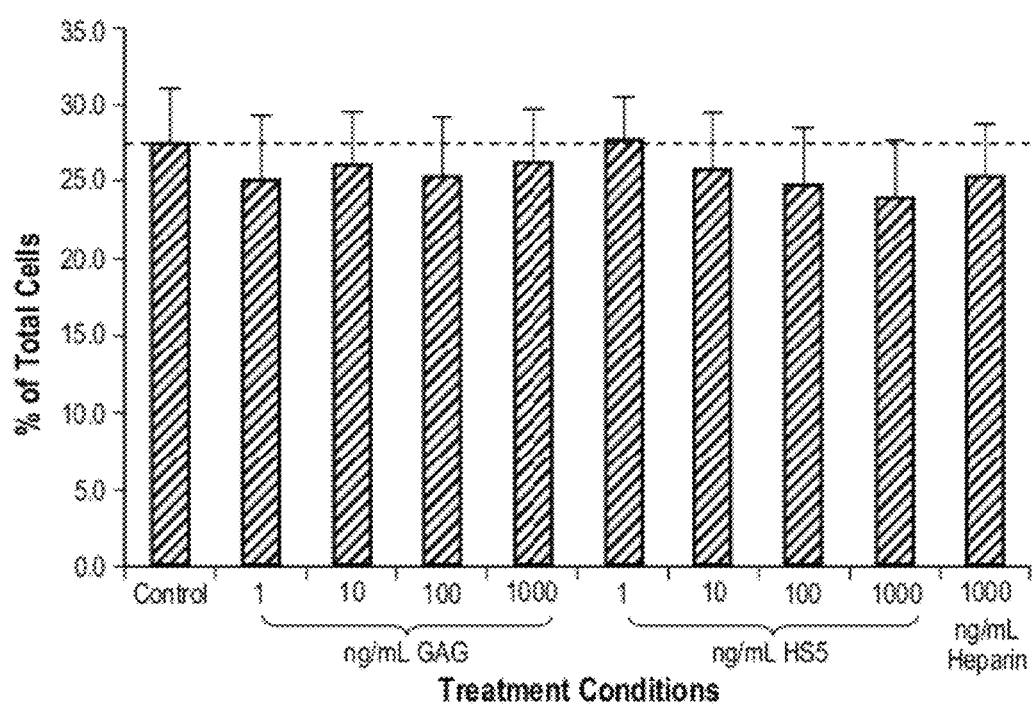

In order to test the effect of bone marrow-derived GAG and HS on CB HSC expansion, CB units were isolated from 5 different donors and purified for hematopoietic progenitor cells. CD34 serves as a marker for early hematopoietic progenitor cells and is widely used to purify HSCs from bone marrow and CB mononuclear cells. In the current study, we purified CD34+ cells from fresh CB units at greater than 85% purity as represented in FIG. 4. For this particular sample, 12% of the freshly isolated mononuclear cells are CD34+ CD38− cells, which constitute the more immature subpopulation of the CD34+ cells. The percentage of CD34+ CD38− cells freshly isolated from CB varied greatly among the different samples, ranging from 12% to 62% and an average of 37.4%. After 12 days ex vivo expansion in the presence of SCF, TPO and Flt3-L, the percentage of CD34+ CD38− cell population generally decreased with an average of 27.3% of the total mononuclear cells, ranging from 18.7% to 37.1%) (FIG. 5B).

The Effect of Total GAG or HS5 on HSC Expansion and Phenotypic Marker Expression A wide variability was observed in the fold increase of total mononuclear cells among the different samples after 12 days ex vivo expansion. The cells treated with only cytokines increase in number by an average of 92 fold and a range of 11 to 286-fold increase. The magnitude in the fold increase seemed to correspond to the percent CD34+ CD38− cell populations found in each expanded HSCs (data not shown). However, neither total GAG nor HS5 enhances HSC expansion compared to control for each donor (FIG. 5A). The percentage of CD34+ CD38− cells after 12-day expansion was also not affected by the addition of total GAG or HS5 (FIG. 5B). Additionally, total GAG and HS5 had no effect on HSC phenotypic markers assessed in the study (Table 2).

Clonogenic Potential of HSC Expanded in the Presence of Total Gag or HS5

Figure 6:
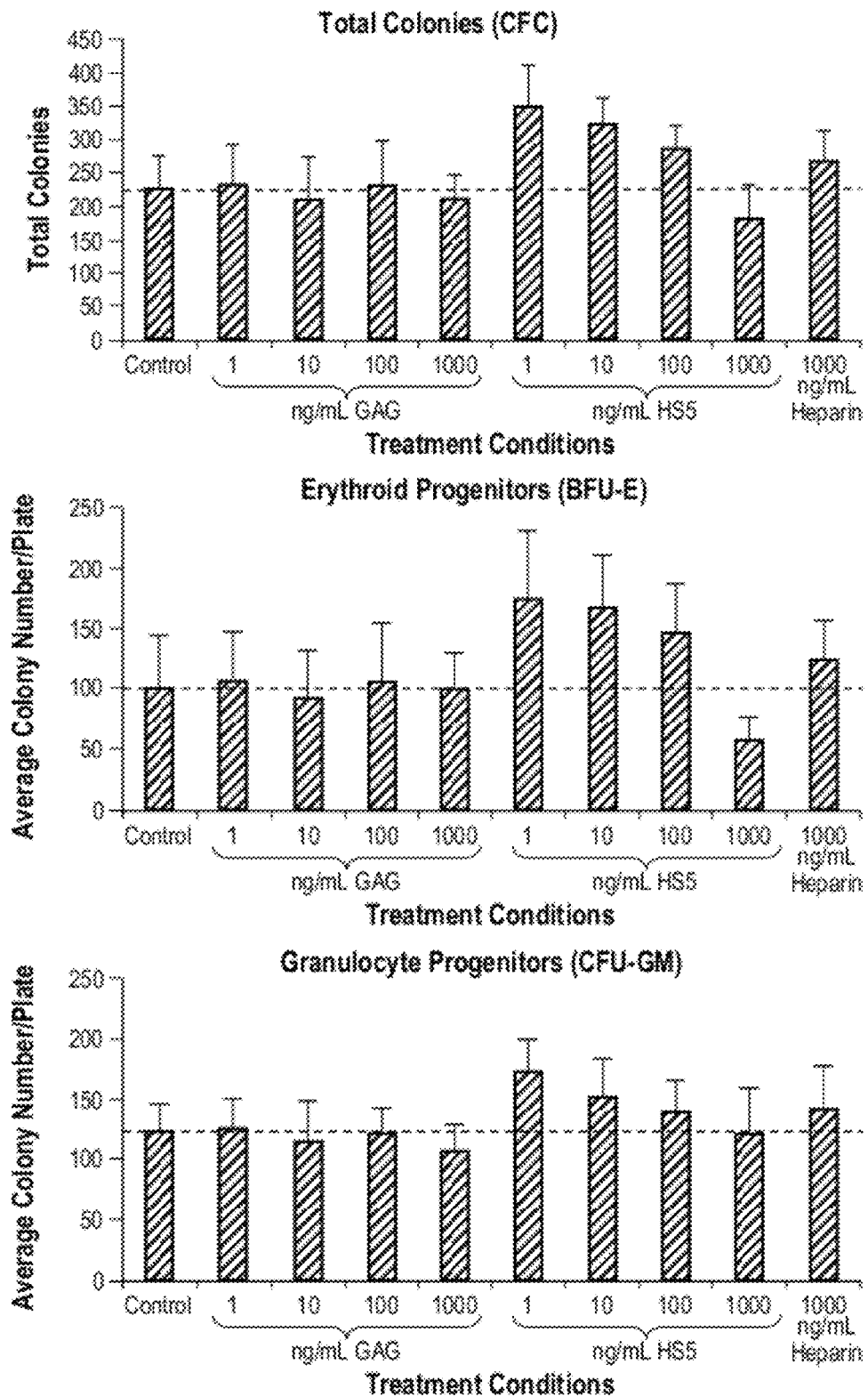
FIG. 6. HS5 but not total GAG markedly increased the clonogenic potential of HSCs and the formation of erythroid progenitors (BFU-E) and granulocyte progenitors (CFU-GM), especially at low dose.

Despite not affecting the expansion of HSCs, we were interested in whether BMS5-derived total GAG and HS5 had any effect on the clonogenic potential of HSCs and the number of committed HSCs in the population. Presently, we found that total GAG had no effect on the clonogenic potential of HSC. However, low dose of HS5 (100 ng/mL or less) increased the clonogenic potential of HSC (FIG. 6). The number of committed HSC toward the erythroid (BFU-E) and granulocyte (CFU-GM) lineage also increased at low dose of HS5.

Discussion

Since the concept of the stem cell niche was first introduced 3 decades ago by Schofield (22), the knowledge behind the role of stromal components toward HSC maintenance has evolved extensively. Both stromal-derived cytokines and proteoglycans have been shown to play an equally important role in hematopoiesis. The role of proteoglycans expressed by stromal cells has been extended to supporting endogenously expressed hematopoietic cytokines not only on the surface of stromal cells and ECM, but also in solution (7).

Indeed, 70% of total GAG synthesized by stromal cells is present in solution rather than on the stromal layer (23). This observation suggests a greater role for proteoglycans than merely modulating the localization of hematopoietic cytokines on the stromal layer. Here, we observed that purified HS5 from bone marrow conditioned media performed better than total GAG in maintaining the clonogenic potential of ex vivo expanded HSCs. Gupta et al (7) has also attributed HS as the GAG subset within bone marrow conditioned media that can maintain LTC-IC for extended culture. Heparan sulfate has been implicated in various roles outside the hematopoietic niche, including facilitating protein dimerization, ligand-receptor interaction and protein stabilization (24-26). Consequently, it may also hold an important role in modulating various physiological and pathological processes within the hematopoietic niche.

The protein-binding capacity and function of HS are dictated by the length of the polysaccharide chain and the degree and pattern of sulfation of its disaccharide units (26-28). Gupta et al (29) compared the sulfation profile of HS derived from a hematopoiesis supportive and non-supportive cell line and found that 6-O sulfation is highly expressed in supportive HS. Interestingly, HS5 that was purified from BMS5 in the current study possesses a high percentage of 6-O sulfation as well. The highly 6-O sulfated HS has been previously shown to bind to hematopoietic cytokines such as interleukin-3, macrophage inflammatory protein-1α (MIP-1α), and thrombospondin (29, 30). Emphasizing its importance further, the removal of 6-O-sulfation has been found to reduce the ability of heparin, a more extensively sulfated form of HS, to maintain LTC-IC in extended culture. Since O-sulfation was also found to be crucial for CD34+ cell interactions with heparin, it was speculated that HS proteoglycans exerts their effect on hematopoiesis by bringing HSC, stromal cells, ECM components and cytokines within proximity to one another. Given that our study shows that soluble HS5 influences the number of committed HSCs in the absence of its protein core, it is possible that stromal cell HS affects hematopoiesis by modulating protein conformation and presentation as well.

Ex vivo expansion of CB HSCs generally increases the growth of committed cells at the expense of the more primitive CD34+ CD38− cells, an HSC subset that is required for the reconstitution of long-term multilineage hematopoiesis. Hence, ex vivo expanded CB HSC has been coupled with unmanipulated CB for clinical transplantations (4, 31-33). This co-transplantation method serves two purposes. Firstly, it serves to increase the total number of nucleated cells (NC) transplanted. Secondly, it serves to balance the early engraftment that is anticipated from the more committed expanded CB populations, with a long-term immune reconstitution that can be derived from primitive cells found in the unmanipulated CB fraction. Heparan sulfate (HS5) acts favorably toward increasing the number of committed clonogenic cells in the expanded HSC population. Since colony forming cell (CFC) content in CB HSCs is touted as a better indicator of survival rates in transplant patients compared to total NC (34), the inclusion of HS5 during HSC ex vivo expansion may potentially reduce mortality in CB transplant patients.

The results here have strengthened the importance of bone marrow stromal-derived HS within the hematopoietic niche in facilitating hematopoiesis and the feasibility of its use in HSC ex vivo expansion, especially in the expansion of committed progenitor cells.

Example 3

Human Bone Marrow Stroma-Derived Heparan Sulphate Enhances BMP-2 Activity with Reduced Potential Side Effects Compared to Heparin Lowering the efficacious dose of BMP-2 for the repair of critical-sized bone defects is highly desirable, as supra-physiological amounts of BMP-2 have an increased risk of side effects and a greater economic burden for the healthcare system.

In this Example we demonstrate that isolated HS(HS5) from a bone marrow stromal cell line has comparable activity to heparin in its ability to enhance BMP-2-induced osteogenesis in C2C12 myoblasts, through increased ALP activity and osteocalcin transcript expression. Notably, commercially available HS variants from porcine kidney and bovine lung failed to generate similar effects. This Example establishes that heparin and HS5 influenced BMP-2 availability in a similar manner; they prolonged BMP-2 half-life and sustained BMP-2 activity, reduced interactions between BMP-2 with its antagonist noggin, and modulated the distribution of BMP-2 on the cell surface. Interestingly, HS5 greatly enhanced matrix mineralization induced by BMP-2 while heparin inhibited it. Furthermore, heparin exhibited strong anticoagulant activity as compared to the panel of HS variants we tested. Due to its lower degree of sulfation and greater heterogeneity in sulfation pattern compared to heparin, HS can provide a greater selectivity for BMP-2, while minimizing the number of non-specific interactions that can generate undesirable side effects.

Methods

Materials

All cell culture reagents were purchased from Sigma-Aldrich unless stated otherwise. All purified recombinant proteins were purchased from R&D Systems, Inc. Commercial porcine intestinal mucosa-derived heparin and heparan sulfate, and bovine kidney-derived heparan sulfate were purchased from Sigma-Aldrich. All cell lines were purchased from American Type Culture Collection (ATCC).

Cell Culture

The immortalized human bone marrow stromal cell line (HS-5, ATCC CRL-11882), herein referred to as BMS5 was maintained in DMEM, 10% FCS (Lonza Group Ltd.), 100 U/mL penicillin/streptomycin (P/S), 4 mM L-glutamine and 1.5 g/L $NaHCO_3$. Myoblast C2C12 cell was maintained in DMEM, 10% FCS and 100 U/mL P/S. Chinese Hamster Ovary (CHO) K1 and pgsD 677 cells were maintained in Ham's F-12 medium (Invitrogen), 10% FCS and 100 U/mL P/S. All cells were maintained at 37° C./5% $CO_2$.

Unless stated otherwise, C2C12 cells were seeded at $2 \times 10^4$ cells/$cm^2$ in 24-well plates in maintenance media. Post-seeding (24 h), the culture media was replaced with treatment media (maintenance media with FCS reduced to 5%) in the presence/absence of 100 ng/mL BMP-2 and varying concentrations of noggin and GAGs. The cells were cultured in treatment media for 3 days and immediately assayed.

Activity of Conditioned Media from Cells

Cells were plated at $3 \times 10^4$ cells/$cm^2$ in maintenance media. After 24 h, the media was changed to treatment media and the conditioned media collected 24 h later, spun at 3000 rpm for 5 min to remove any cell debris, then passed through a 0.45 µg filter, and stored at −20° C. The conditioned media was then thawed and mixed (1:1 ratio) with fresh treatment media prior to being introduced to the culture.

GAG Extraction, Purification and Disaccharide Unit Analysis

The BMS5 cells were seeded at $3 \times 10^4$ cells/$cm^2$ in a 15-cm dish in maintenance media. One day after seeding, the media was replaced with serum free media and the media collected every other day up to day-11 and pooled. At each collection point, the media was centrifuged at 5000 rpm for 10 min at 4° C. and filtered using 0.45 µg filter to remove cell debris prior to storage at 4° C. The purification of HS from the cell-conditioned media (herein called HS5) and its disaccharide analysis were performed as previously described (Murali S, Manton K J, Tjong V, Su X D, Haupt L M, Cool S M, Nurcombe V 2009 Purification and characterization of heparan sulfate from human primary osteoblasts. Journal of Cellular Biochemistry 108(5):1132-1142)).

Glycosaminoglycan (GAG) Biotinylation

GAG was biotinylated according to methods described by Osmond et al. with some modifications (Osmond R I W, Kett W C, Skett S E, Coombe D R 2002 Protein-heparin interactions measured by BIAcore 2000 are affected by the method of heparin immobilization. Analytical Biochemistry 310(2): 199-207). Briefly, 1 mg of sugar in 100 µL of 0.1M 4-morpholinoethanesulfonic acid (MES), pH 5.5, was mixed with 30 µL of 2 mg/mL biotin-LC-hydrazide (Pierce Chemical Co.) dissolved in MES, and 0.75 mg 1-ethyl-3-(3-dimethylaminopropryl)carbodiimide hydrochloride (EDC), and incubated at room temperature for 2 h. Subsequently, another 0.75 mg of EDC was added and incubated for additional 2 h. The biotinylated GAGs were then purified using a fast desalting column (GE Healthcare).

Dot Blot Assay

To confirm the biotinylation of GAG, 50 μL biotinylated GAGs were passed through Immobilon NY+ membrane (Millipore) by gravity flow using a dot blot apparatus (Biorad). A solution of 120 ng biotin was also passed through the membrane as a negative control. The membrane was then blocked with PBS containing 0.5% BSA, 3% non-fat dry milk and 0.5% Tween-20 and biotin detected using HRP-conjugated streptavidin (BD Pharmingen).

To determine GAG binding to BMP-2, 0.5 μg of BMP-2 in 200 μL PBS was added under vacuum onto a nitrocellulose membrane. The blot was blocked with 5% BSA in PBS prior to incubating each BMP-2 spot with 1 μg of biotinylated GAG in 200 μL PBS. The bound biotinylated GAG was detected as described above.

GAG Binding Assay

The interaction between GAG and BMP-2 was determined using GAG binding plates (Iduron) according to the manufacturer's specification. GAG (10 μg/mL) was incubated on the plate prior to adding BMP-2. Bound BMP-2 was detected using biotinylated anti-BMP-2 antibody (R&D Systems).

Alkaline Phosphatase Activity

The cell layer was washed in PBS before lysis in RIPA buffer in the presence of protease inhibitor cocktail (Calbiochem). The protein content was determined using BCA protein assay kit (Pierce Chemical Co.). ALP activity was measured by mixing 7 to 10 μg of protein with p-nitrophenylphosphate (Zymed). Enzyme activity was measured as a change in absorbance at 405 nm due to the production of p-nitrophenol per μg protein and normalized to treatment containing BMP-2 alone.

Real-Time PCR

Total RNA was isolated and reverse transcribed as previously described (Ng K W, Speicher T, Dombrowski C, Helledie T, Haupt L M, Nurcombe V, Cool S M 2007 Osteogenic differentiation of murine embryonic stem cells is mediated by fibroblast growth factor receptors. Stem Cells and Development 16(2):305-318). Expression level of target genes was determined using real-time PCR by amplification in ABI Prism 7500 FAST® sequence detection system (Applied Biosystems Inc.) using primers/probes for RUNX2 and osteocalcin as described previously (Ng et al. supra) and Taqman Gene Expression Assays (Applied Biosystems Inc.) for β-actin and GAPDH. $2^{-(\Delta Ct)}$ values from biological triplicates were measured in triplicates and normalized to β-actin and GAPDH levels to represent relative expression unit (REU).

Mineralization Assay

Myoblast C2C12 cells were seeded at $5 \times 10^3$ cells/cm$^2$ in 24-well plates in maintenance media. After 24 h, the media was replaced with osteogenic media (DMEM, 5% FCS, 50 μg/ml ascorbic acid and 10 mM 6-glycerophosphate) in the presence/absence of 100 ng/mL BMP-2 and 3 μg/mL GAG. The media was changed every 2 days. After 14 days, the cell layer was washed with PBS, fixed with 4% paraformaldehyde, and stained for 10 min in 0.1% alizarin red solution.

BMP-2 Stability Assay

BMP-2 at 100 ng/mL was incubated alone or in the presence of 3 μg/mL of GAG in treatment media at 37° C./5% $CO_2$. The media was collected at an indicated time and stored at −80° C. prior to BMP-2 quantitation. The amount of BMP-2 present in the media was assayed using a BMP-2 Quantikine ELISA kit (R&D Systems) according to the manufacturer's specification.

BMP-2 Activity

C2C12 cells were plated on 24-well plates as described earlier. BMP-2 in treatment media was prepared as described in the BMP-2 stability assay for an indicated amount of time. Prior to adding the media containing BMP-2, the cell layer was pre-incubated with fresh treatment media for 24 h. The cells were then subjected to BMP-2 for 15 min and the cell layer was lysed in Laemmli buffer, resolved in a 4-12% SDS-PAGE gel, and immunoblotted with antibodies against Smad 1/5/8 (Santa Cruz Biotechnology) and phosphorylated Smad 1/5/8 (Cell Signaling Technology).

Immunoprecipitation and Western Blot

BMP-2 (200 ng/mL) was incubated with 600 ng/mL Fc-conjugated noggin in the presence of 6 μg/mL GAG. BMP-2 (100 ng/mL) was incubated with Fc-conjugated BMPR-IA (640 ng/mL) in the presence of 3 μg/mL GAG. The complex formed was immunoprecipitated with protein A/G sepharose beads (Santa Cruz Biotechnology) for 1 h at 4° C. The precipitated sample was then analyzed in a 4-12% SDS-PAGE and immunoblotted using anti-noggin (Millipore), anti-human IgG (Jackson Immunoresearch) for BMPR-IA (eBioscience), and anti-BMP-2 antibodies (R&D Systems, Inc.). Densitometry analysis using Quantity One software (Bio-Rad) was performed on 3 separate experiments to arrive at a mean value. The relative amount of bound BMP-2 was calculated by first, normalizing each BMP-2 densitometry value to its respective noggin or BMPR-IA densitometry value. Subsequently, the calculated value obtained is normalized to the treatment group containing no GAG.

FACS

Cultured cells were detached using 5 mM EDTA in RPMI 1640 containing 10% FCS and 32 mM HEPES. The detection of heparan sulfate proteoglycan on the surface of CHO K1 and pgsD 677 cells was performed as previously described (Rolny C, Spillmann D, Lindahl U, Claesson-Welsh L 2002 Heparin amplifies platelet-derived growth factor (PDGF)-BB-induced PDGF alpha-receptor but not PDGF beta-receptor tyrosine phosphorylation in heparan sulfate-deficient cells—Effects on signal transduction and biological responses. Journal of Biological Chemistry 277(22):19315-19321). To detect BMP-2 bound to the cell surface, 20 ng BMP-2 was pre-incubated with 1 μg anti-BMP-2 antibody before incubation with GAG. The cells were incubated with the BMP-2/antibody/GAG mixture in RPMI 1640/10% FCS for 1 h on ice. Secondary antibody was introduced as previously described (Rolny et al. supra).

Anticoagulation Assay

GAGs were assessed on their effect on antithrombin III activity. The assay was performed using the COATEST Heparin kit (Chromogenix) according to the manufacturer's specification. Values were represented as the relative inhibition of Factor Xa activity when compared to treatment group containing no GAG.

In vivo Implantation

HELISTAT® collagen sponges (Integra Life Sciences Corp, USA) measuring 3.5×7×5 mm were pre-soaked in 5 μg BMP-2 in the presence/absence of 25 μg of GAG (i.e. heparin, HS5 or bHS) and inserted into polycaprolactone (PCL) tubes (Osteopore International Pte Ltd, Singapore) measuring 4.5 mm inner diameter, 3 mm height and 1 mm wall thickness. Collagen sponges pre-soaked in PBS served as a control. Porcine-derived HS was eliminated from the in vivo experimental setup since it consistently generated similar effects as bHS. Bilateral hind limb muscle pockets (2 in each limb) were created in 7 female Sprague Dawley rats (weighing 120-150 g) [H. S. Yang, W. G. La, S. H. Bhang, J. Y. Jeon, J. H. Lee, B. S. Kim. Heparin-conjugated fibrin as an injectable system for sustained delivery of bone morphogenetic protein-2. Tissue Eng. Part A 16 (2010) 1225-1233] and randomly assigned to an experimental treatment. Pockets were created in the muscle by blunt dissection parallel to the muscle fiber long axis after creating 1 cm transverse incisions over each muscle. All surgical procedures were carried out under general anesthesia and aseptic conditions. Anesthesia prior to surgery and its maintenance throughout surgery was achieved with isoflurane administration via an induction chamber and facemask. Prophylactic antibiotics (Baytril, 10 mg/kg) and analgesics (Buprenorphine, 0.01-0.05 mg/kg) were administered subcutaneously for 3 days post-surgery. Surgeries were performed in strict accordance with guidelines approved by A*STAR's Institutional Animal Care and Use Committee.

Bone Formation Analysis

The rats were sacrificed and specimens harvested 8 weeks after implantation. Three samples per treatment were assessed using 2D x-rays, μ-CT and histology for bone mineralization. An Imaging Radiographic System (MUX-100, Shimadzu) was used to capture 2D x-ray images of the muscle pockets immediately after the surgery and at week 8. Digital micrographs were then taken of the x-rays. Micro-CT images were captured with a μ-CT scanner (Skyscan 1076; Skyscan, Belgium) and analyzed using Mimics 13.1 software (Materialise, Belgium) as previously described [B. Rai, J. L. Lin, Z. X. H. Lim, R. E. Guldberg, D. W. Hutmacher, S. M. Cool. Differences between in vitro viability and differentiation and in vivo bone-forming efficacy of human mesenchymal stem cells cultured on PCL-TCP scaffolds. Biomaterials 31 (2010) 7960-7970]. The data was recorded as total bone volume ($mm^3$).

For histological analysis, the extracted specimens were fixed in 10% neutral buffered formalin for 1 week under vacuum, and decalcified in 30% formic acid for 2 weeks at room temperature. The specimens were then processed using a vacuum infiltration processor (Sakura Finetek, Japan), followed by dehydration, clearing, and embedding in Paraplast® paraffin wax (Thermo Scientific) as previously described [[B. Rai, J. L. Lin, Z. X. H. Lim, R. E. Guldberg, D. W. Hutmacher, S. M. Cool. Differences between in vitro viability and differentiation and in vivo bone-forming efficacy of human mesenchymal stem cells cultured on PCL-TCP scaffolds. Biomaterials 31 (2010) 7960-7970]. Sections were made using a rotary microtome (Leica Microsystems, Germany), placed onto microscope slides, stained with Hematoxylin/Eosin or Modified Tetrachrome [Z. A. Ralis, G. Watkins. Modified tetrachrome method for osteoid and defectively mineralized bone in paraffin sections. Biotech. Histochem. 67 (1992) 339-345] and viewed with an Olympus upright fluorescence microscope (BX51).

Statistical Analysis

Experiments were performed in duplicate or triplicate samples and repeated 2 to 3 times. Mean differences between samples were analyzed by performing a homogeneity of variance test, followed by ANOVA and Tukey's or Tamhane's posthoc testing. Differences of $p<0.05$ was considered significant.

Results

Figure 9A:
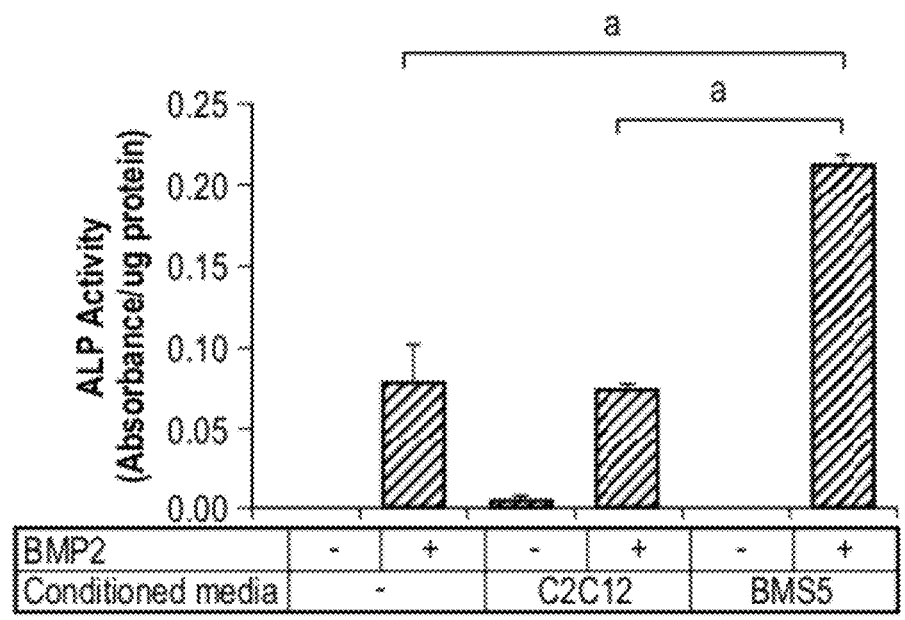
FIG. 9. BMS5 conditioned media, which contains BMP-2-binding HSs, is able to enhance BMP-2-activity. A) Conditioned media derived from BMS5 enhanced ALP activity induced by the addition of 100 ng/mL of BMP-2 for 3 days in C2C12 cells, while C2C12-derived conditioned media and unconditioned media showed no effect. B) Various types of HS were expressed in BMS5 as revealed by its transcript expression profile. (C) All GAGs tested bound to BMP-2 in a dose-dependent manner, with HS5 showing the least capacity to bind BMP-2. (D) HS5 showed lower capacity to bind pre-adsorbed BMP-2 on a nitrocellulose membrane, which supported the GAG binding plate assay. (E) Pre-adsorbed GAG on a cationic membrane was detected using HRP-conjugated streptavidin and showed greater GAG biotinylation on HS5 compared to heparin. Significant values are represented as a p<0.05.

Conditioned Media from Human Bone Marrow Stromal Cell Line (BMS5) Enhanced BMP-2 Activity Conditioned media derived from C2C12 and BMS5 cells was added to C2C12 cells in the presence/absence of BMP-2. In the absence of BMP-2, none of the conditioned media induced ALP activity (FIG. 9A). However, in the presence of BMP-2, only BMS5 conditioned media further enhanced ALP activity above BMP-2-induced levels.

Figure 9B:
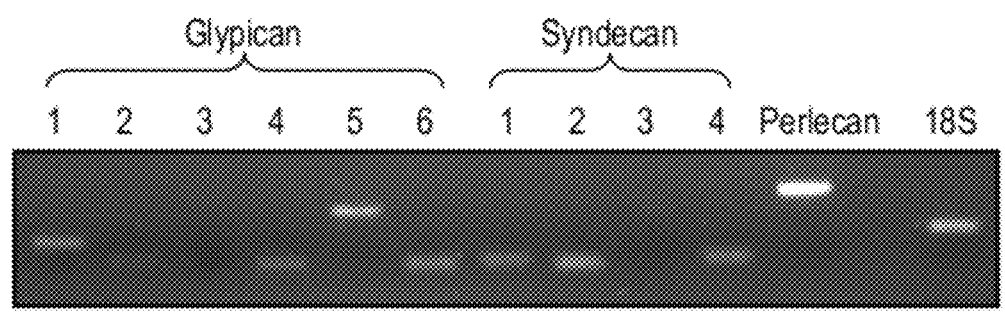

To determine whether HSPGs might constitute part of the active component of the BMS5 conditioned media, mRNA transcript expression of the three major families of HSPGs was examined as a prelude to isolating HS from the conditioned media (FIG. 9B). All the HSPG isoforms for glypican and syndecan, with the exception of glypican-3 and syndecan-3, were expressed in BMS5. Notably, the soluble HSPG isoform perlecan was abundantly expressed.

Following HSPG gene profiling, HS was isolated from BMS5 conditioned media (termed HS5) and subjected to molecular weight distribution and disaccharide analysis. The molecular weight of HS5 was distributed at 7.5, 29 and 75 kDa and the major disaccharide units were uronic acids linked to non-sulfated glucosamines or 6-0 sulfated glucosamines (Table 3). The identity of a large portion of the disaccharide units could not be determined due to the current lack of standards for all possible combinations of variably sulfated disaccharide units.

Heparan-GAG Interactions with BMP-2

Figure 9C:
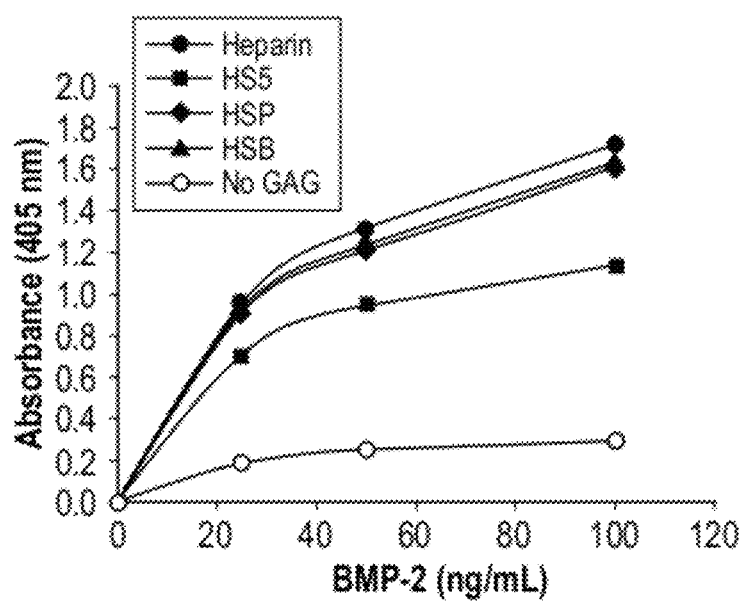

The ability of HS5 to bind BMP-2 was compared with commercially available GAGs using a GAG binding plate assay (FIG. 9C). Irrespective of the GAG variant used to coat the plate surface, BMP-2 bound to the immobilized GAG in a dose dependant manner. When GAG was omitted (no GAG control), minimal BMP-2 binding was detected. Furthermore, heparin, porcine mucosal HS (pHS) and bovine kidney HS (bHS) bound more BMP-2 than did HS5, irrespective of dose.

Figures 9D, 9E:
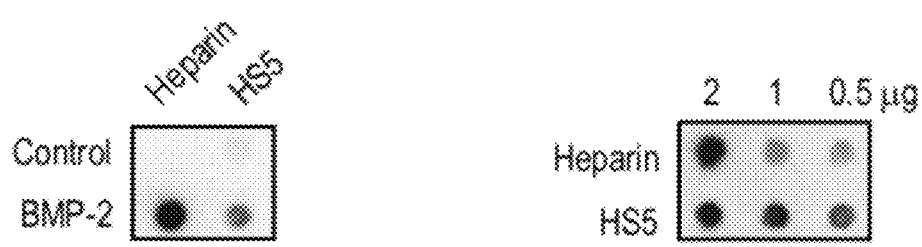

To exclude the possibility that less HS5 bound to the GAG plate, so reducing the amount of bound BMP-2, we performed a nitrocellulose dot blot assay using immobilized BMP-2 as the capture substrate. The result confirms that more heparin binds to BMP-2 compared to HS5 (FIG. 9D), a result that is not due to differences in biotinylation of the GAG (FIG. 9E). Rather, HS5 can be more efficiently biotinylated compared to heparin on a per weight basis.

HS5 Enhances BMP-2-Induced Osteogenesis

Figure 10A:
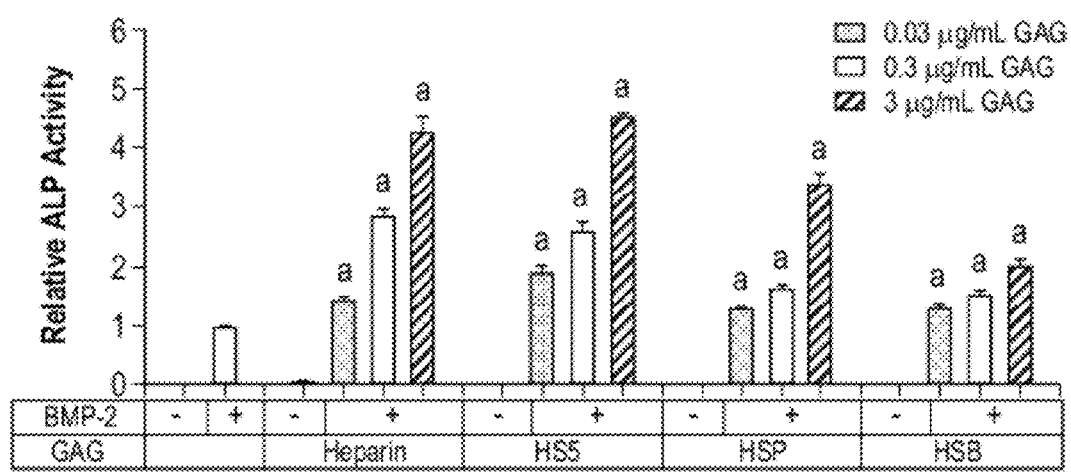
FIG. 10. HS5 enhanced BMP-2-induced osteogenic differentiation in C2C12 cells. (A) All the GAGs dose-dependently enhanced BMP-2-induced ALP activity. HS5 showed comparable activity to heparin but was superior compared to pHS and bHS. (B) HS5 and heparin enhanced BMP-2-induced osteocalcin mRNA expression, presented here as relative expression unit (REU), but not RUNX2. C2C12 cells were cultured in the presence/absence of 100 ng/mL of BMP-2 with increasing amount of GAG (ALP assay) or 3 µg/mL of GAG (transcript expression) for 3 days prior to harvesting the cells. (C) HS5 enhanced BMP-2 induced mineralization while heparin inhibited it. C2C12 cells were cultured in osteogenic media in the presence/absence of 100 ng/mL BMP-2 and 3 µg/mL of GAG for 14 days prior to Alizarin Red staining. Significant values are represented as a p<0.05.

Having established that HS5 binds to BMP-2, we next sought to determine the effect of this interaction on BMP-2 activity. Using ALP activity assays in C2C12 cells, all GAGs tested dose-dependently increased BMP-2-induced ALP activity to levels significantly higher than BMP-2 alone. Furthermore, the combination of heparin or HS5 with BMP-2 resulted in more ALP activity as compared to pHS and bHS at doses above 0.3 μg/ml (FIG. 10A). GAG alone had no effect on ALP activity.

Figure 10B:
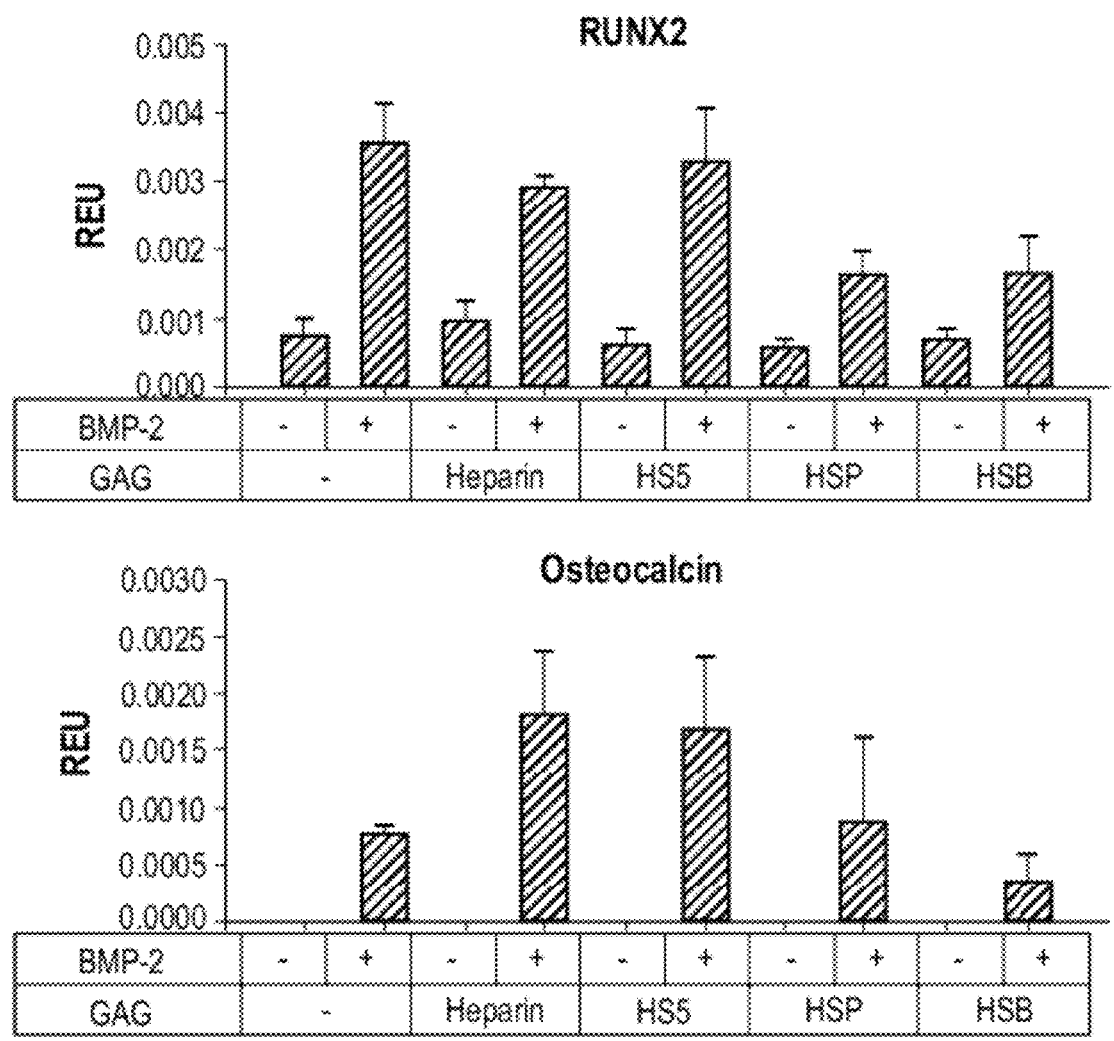

To further assess the effect of GAG/BMP-2 combinations on osteogenic differentiation, we examined RUNX2 and osteocalcin mRNA transcript expressions. Irrespective of the GAG used in combination with BMP-2, no increase in RUNX2 was observed (FIG. 10B). However, when heparin or HS5 was combined with BMP-2, osteocalcin expression increased above levels seen with BMP-2 alone.

Figure 10C:
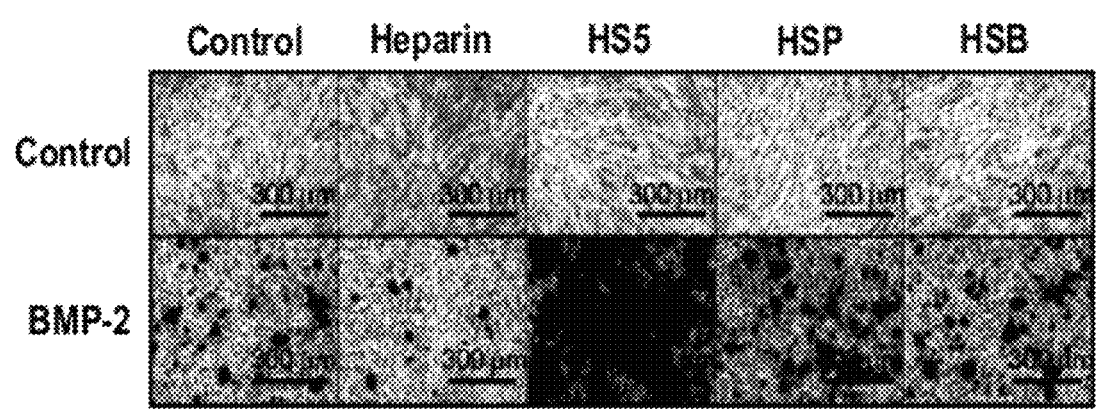

The effect of GAG on matrix mineralization of C2C12 cells was then assessed by Alizarin Red staining (FIG. 10C). When combined with BMP-2, HS5 greatly enhanced matrix mineralization as compared to heparin, pHS or bHS. Notably, matrix mineralization was observed as early as day 6 when cells were stimulated with a combination of BMP-2 and HS5 (data not shown). In contrast, heparin inhibited BMP-2-induced matrix mineralization.

HS5 Prolongs BMP-2 Stability and Activity

Figure 11A:
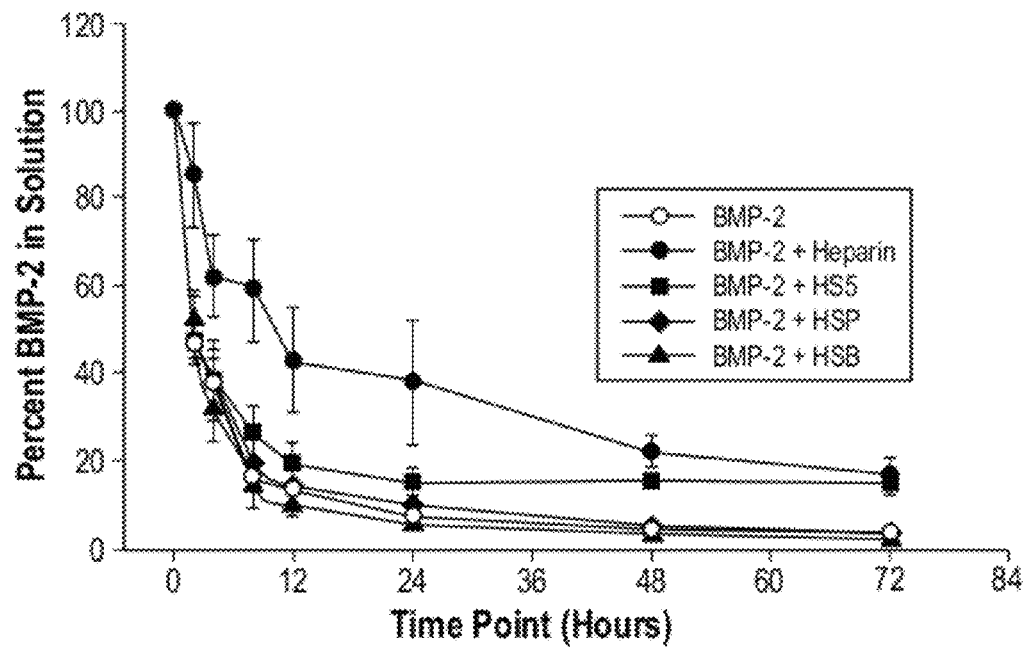
FIG. 11. HS5 and heparin, but not commercial HSs, prolonged BMP-2 stability and activity. (A) BMP-2 stability over time was measured in a BMP-2 Quantikine ELISA kit. 100 ng/mL of BMP-2 was incubated in the presence/absence of 3 µg/mL of GAG for up to 72 h. (B) BMP-2 incubated with heparin or HS5 for up to 72 h remained biologically active as indicated by its ability to induce Smad 1/5/8 phosphorylation (p-Smad 1/5/8) in C2C12 cells.

Next, we examined whether HS5 had an effect on BMP-2 stability. When combined with treatment media, the amount of BMP-2 present in solution decreased to approximately 50% and 3.5% of the starting amount within 2 and 72 h respectively (FIG. 11A). In the presence of heparin, however, 85% of the BMP-2 could be detected after 2 h and 17% after 72 h. In comparison, HS5 had no effect on the amount of BMP-2 detected for the first 8 h. However, from 8 h onwards, the loss of BMP-2 slowed to reach 15% of the original amount after 72 h, a level comparable to heparin. Neither pHS nor bHS affected BMP-2 stability.

Figure 11B:
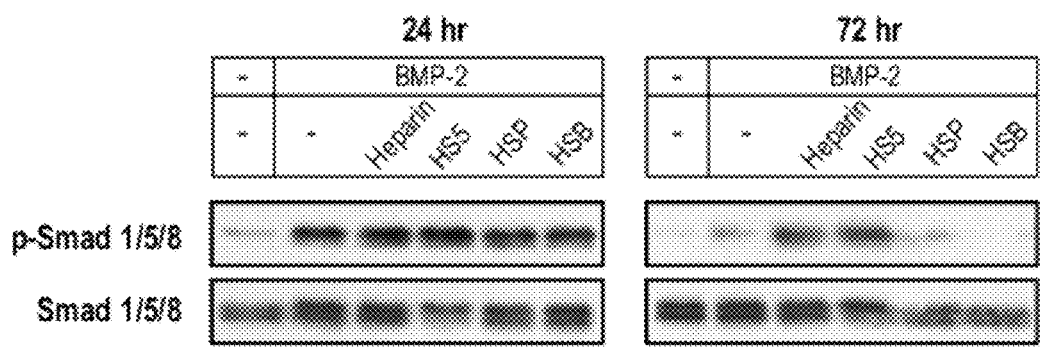

To further examine whether heparin and HS5 help stabilize BMP-2 activity, we tested BMP-2-induced Smad 1/5/8 phosphorylation (p-Smad 1/5/8) in C2C12 cells using BMP-2 or BMP-2/GAG combinations after 24 or 72 h incubation at 37° C. (FIG. 11B). After 24 h incubation, BMP-2-induced p-Smad 1/5/8 activity was observed with or without GAG at comparable intensity. When assayed after 72 h, only BMP-2 in the presence of heparin or HS5 (18 and 8 ng/mL of BMP-2 respectively) was sufficient to induce p-Smad 1/5/8, suggesting that a threshold amount of BMP-2 above 6 ng/mL is sufficient to induce Smad 1/5/8 signaling.

GAGs Modulate BMP-2 Bioavailability

Figure 12A:
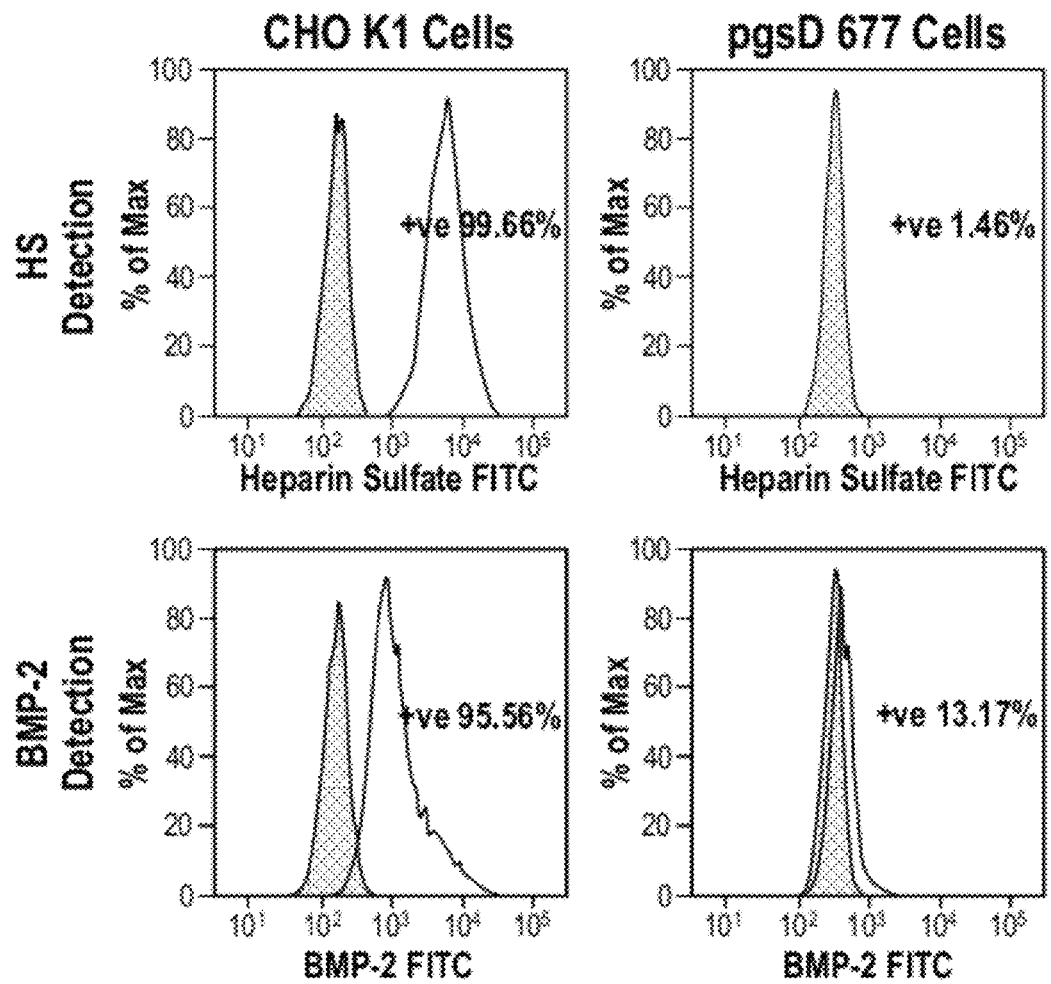
FIG. 12. BMP-2 localization on the cell surface was modulated by endogenously expressed HSPGs and exogenously added GAG. (A) FACS analysis showed that endogenously expressed HSPGs play a significant role in localizing BMP-2 on the cell surface as confirmed in wild type (CHO K1) and HSPG-deficient (pgsD 677) CHO cells. (B) The addition of exogenous GAG reduced the amount of BMP-2 bound on the surface of CHO K1 cells dose dependently.
Figure 12B:
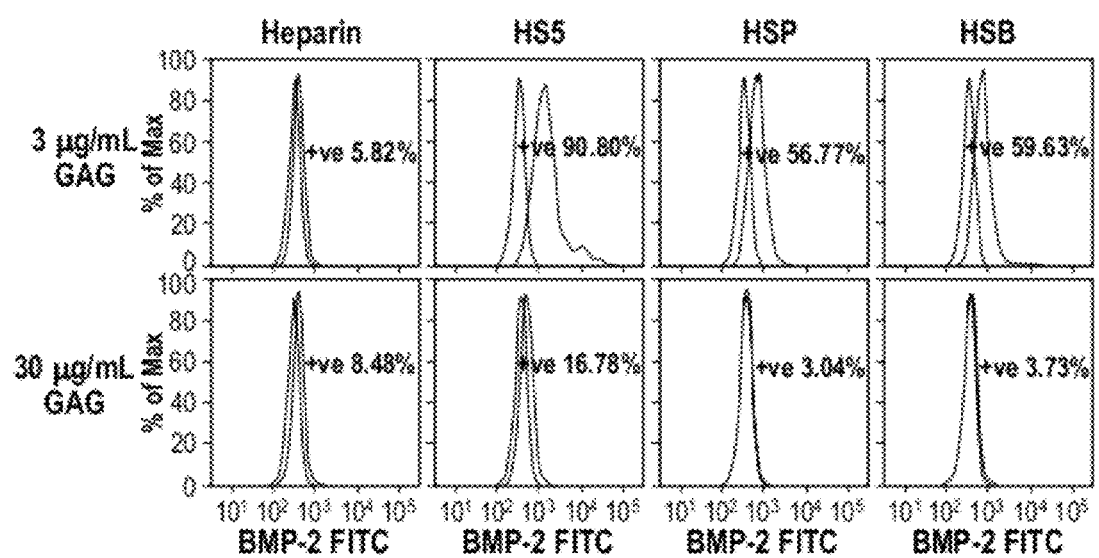

Since BMP-2 is known to bind to endogenous HSPGs on cell surfaces, we next examined whether exogenous GAGs could compete for this interaction, so rendering BMP-2 more bioavailable. Using wild type (CHO K1) and HSPG-deficient mutant (pgsD 677) CHO cells, we confirmed that BMP-2 bound to endogenous HSPGs present on the cell surface (FIG. 12). Initial screening showed that CHO K1 cells expressed high levels of HS, whereas pgsD 677 cells were devoid of endogenous HS (FIG. 12A). In the absence of cell surface HSPGs, the amount of BMP-2 bound to the cell surface was greatly reduced (FIG. 12A). Notably, the addition of soluble GAG to CHO K1 cells was able to reduce the amount of cell surface-bound BMP-2 (FIG. 12B). Heparin was able to effectively prevent BMP-2 cell surface binding at 3 µg/mL compared to the HSs. However, pHS and bHS appeared to be more superior compared to heparin in modulating BMP-2 distribution at 30 µg/mL dose. A similar trend was observed when the experiment was repeated in C2C12 cells (data not shown).

Noggin Activity is Reduced in the Presence of Heparin or HS5

Figure 13A:
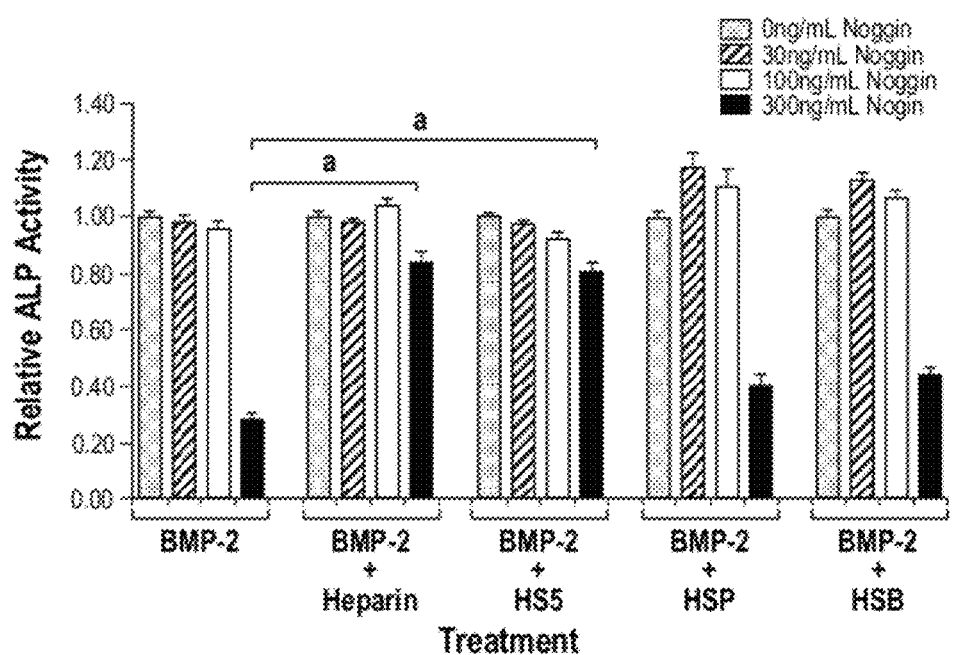
FIG. 13. HS5 and heparin, but not the commercial HSs, reduced the inhibitory effect of noggin toward BMP-2 activity through disrupting their interaction. (A) BMP-2 at 100 ng/mL was pre-incubated with or without 3 µg/mL of GAG, and introduced to C2C12 cells for 3 days together with noggin at the indicated concentration. Values were normalized to ALP activity observed in cells treated with BMP-2 in combination with each respective GAG in the absence of noggin. (B) 600 ng/mL of noggin/Fc was co-immunoprecipitated with 200 ng/mL of BMP-2 in the presence/absence of 8 µg/mL of GAG. Densitometry analysis was derived from 3 separate blots. Relative bound BMP-2 was measured by normalizing the ratio derived from BMP-2 and noggin/Fc bands with that of the treatment group containing no GAG. Significant values are represented as a p<0.001 and b p<0.05 when compared to treatment group containing no GAG.
Figure 13B:
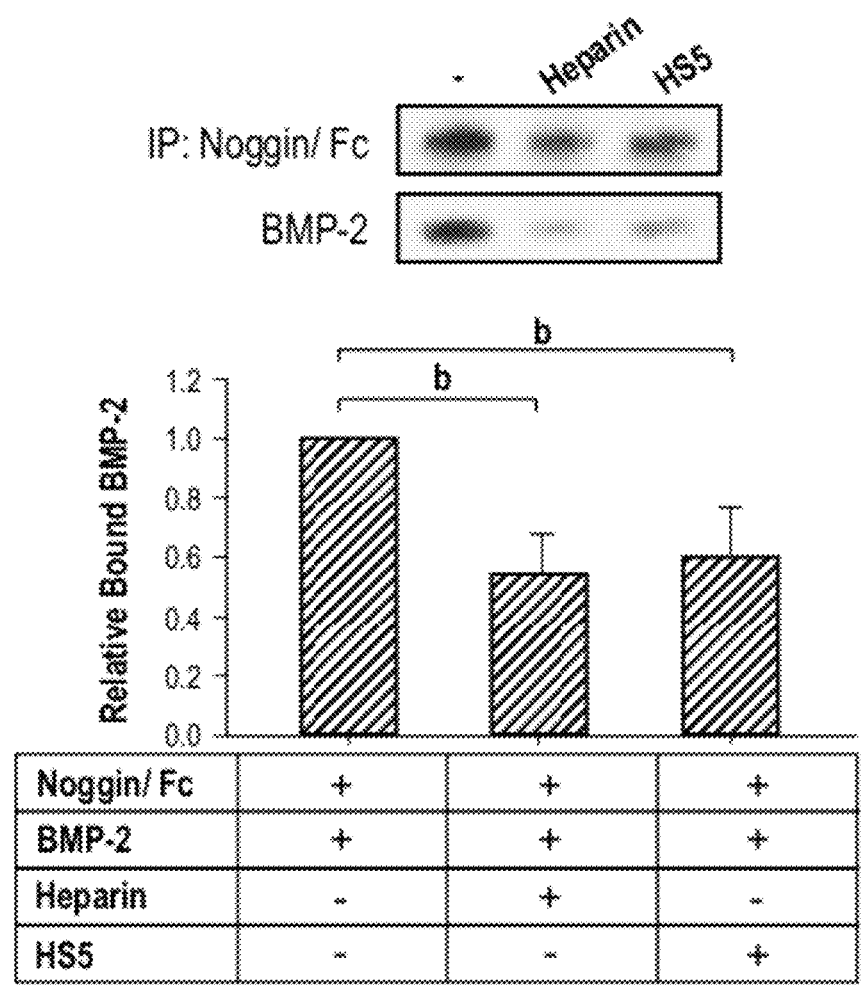

The antagonistic binding of noggin to BMP-2 regulates BMP-2 activity. To determine the effect of GAG on noggin activity, we assayed for ALP activity using BMP-2, GAG and noggin combinations in C2C12 cells. At 300 ng/mL, noggin inhibited BMP-2-induced ALP activity by 70% (FIG. 13A). In the presence of heparin or HS5, 300 ng/mL noggin only reduced BMP-2-induced ALP activity by approximately 20%. Meanwhile, pHS and bHS had negligible effect on noggin activity. Through immunoprecipitation assays, heparin and HS5 were found to significantly reduce the binding interaction between noggin and BMP-2 (FIG. 13B).

The Effect of GAG on BMP-2 Interactions with BMPR-IA

Figure 14:
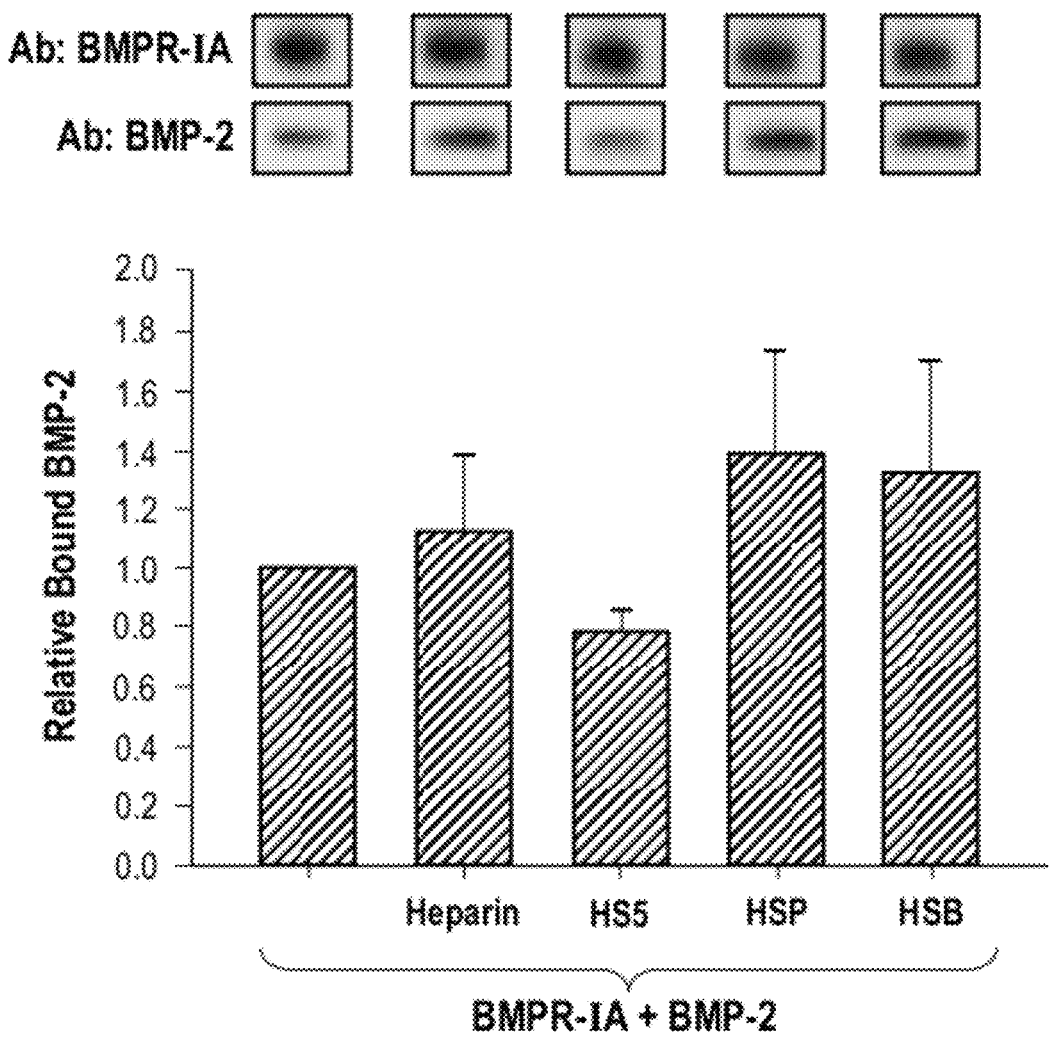
FIG. 14. GAG has minimal effect toward BMP-2 and BMPR-IA receptor interaction. 100 ng/mL BMP-2 was co-immunoprecipitated with 640 ng/mL BMPR-IA/Fc in the presence/absence of 3 µg/mL GAG and separated on a Western blot. Densitometry analysis was derived from 3 separate blots. Relative bound BMP-2 was measured by normalizing the ratio between the BMP-2 band and the BMPR-IA/Fc band with that of the treatment group containing no GAG.

Since HSPG is known to bind FGF receptor (Brickman Y G, Ford M D, Small D H, Bartlett P F, Nurcombe V 1995 Heparan sulfates mediate the binding of basic fibroblast growth factor to a specific receptor on neural precursor cells. J Biol Chem 270(42):24941-8), we next sought to determine whether HS similarly binds to BMP receptor, thereby modulating BMP-2 activity. As C2C12 cells are known to preferentially express BMP receptor IA (BMPR-IA) and that mutation in this receptor blocks response to BMPs (Akiyama S, Katagiri T, Namiki M, Yamaji N, Yamamoto N, Miyama K, Shibuya H, Ueno N, Wozney J M, Suda T 1997 Constitutively active BMP type I receptors transduce BMP-2 signals without the ligand in C2C12 myoblasts. Experimental Cell Research 235(2):362-369 and Namiki M, Akiyama S, Katagiri T, Suzuki A, Ueno N, Yamaji N, Rosen V, Wozney J M, Suda T 1997 A kinase domain-truncated type I receptor blocks bone morphogenetic protein-2-induced signal transduction in C2C12 myoblasts. Journal of Biological Chemistry 272(35): 22046-22052), we performed a nitrocellulose dot blot assay against immobilized BMPR-IA detected using biotinylated GAG. Notably, binding of the GAGs tested to BMPR-IA was not detected. Next, we examined whether GAG affected the binding of BMP-2 to BMPR-IA. Using co-immunoprecipitation of BMPR-IA and BMP-2, we showed that the addition of GAG had no appreciable effect on BMP-2/BMPR-IA interactions (FIG. 14).

HS5 has No Anticoagulant Activity

Figure 15:
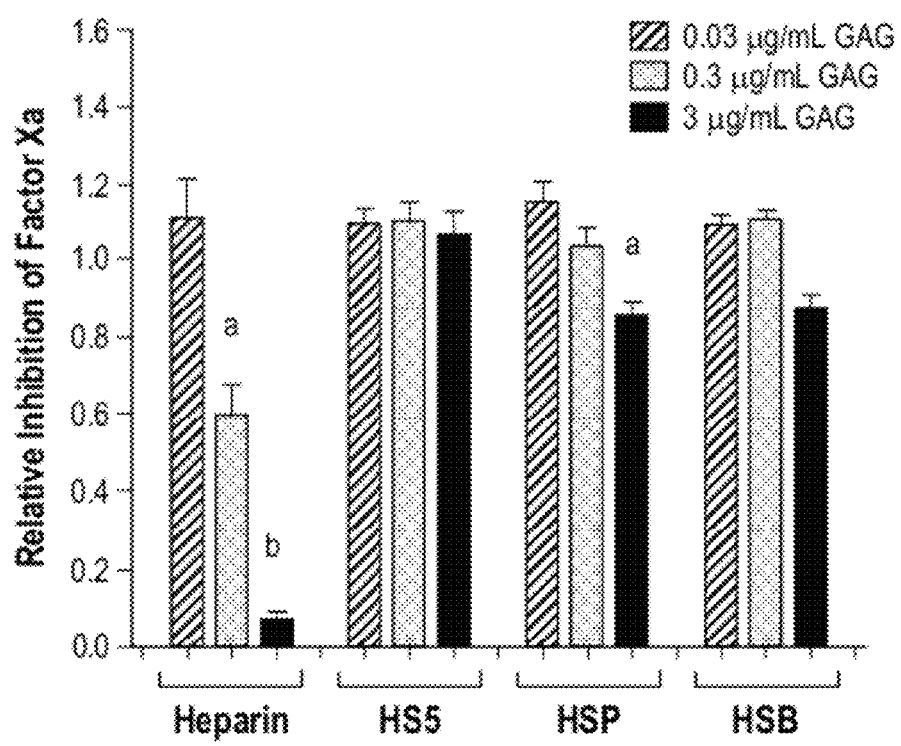
FIG. 15. HS has minimal anticoagulant activity compared to heparin. At the indicated concentration, GAG was incubated with antithrombin (AT) before the addition of factor Xa (FXa). Any FXa that was not inhibited by AT was measured photometrically using chromogenic substrate S-2222. Relative inhibition was measured by normalizing the values to that of the treatment group containing no GAG. Significant values are represented as a p<0.001 and b p<0.05 when compared to the treatment group containing no GAG.

As a fracture hematoma plays an important role in bone repair, we next determined the anticoagulant activity of antithrombin (AT) in the presence of GAG (FIG. 15). Antithrombin pre-incubated with GAG was combined with Factor Xa (FXa). Any FXa that was not inhibited by the activated AT is able to cleave the chromogenic substrate S-2222 to release a chromophore. As expected, heparin (a known anticoagulant) dose dependently activated AT resulting in the inhibition of FXa. In the presence of pHS or bHS, AT significantly reduced FXa activity, but only at 3 µg/mL, whereas HS5 did not activate AT at any doses tested.

HS5 Enhanced BMP-2-Induced Bone Formation in a Rat Ectopic Model

Figure 18B:
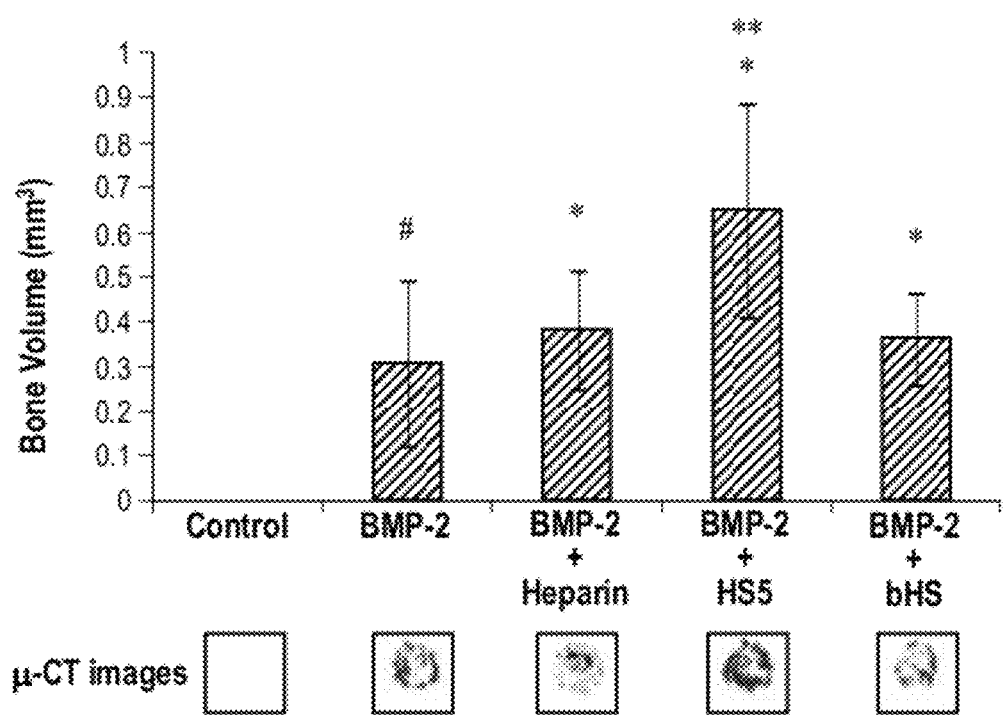
FIG. 18. HS5 enhanced BMP-2-induced bone formation in a rat ectopic model at 8 weeks. (A) Representative 2D x-rays of the rat hind limb muscle treated with BMP-2 alone (i) or in the presence of heparin (ii), HS5 (iii) or bHS (iv) revealed varying degrees of bone mineralization. (B) The bone volume (mm³), gated based on a pre-determined threshold that resembles dense cortical bone, and its corresponding 3D images showed that the combination of HS5 treatment resulted in significantly higher levels of bone formation compared to BMP-2, while no treatment (NT) showed absence of bone formation. This was determined by μ-CT analyses. (C) Representative histological sections confirmed the abundance of lamellar bone in HS5 implants. Staining consisted of Hematoxylin/Eosin (H & E) and Modified Tetrachrome (blue=osteoid, red=bone). At: Adipose tissue, Ma: Bone marrow, B: Bone, L: Lamellar bone, scale: 100 μm. Significant difference when compared to control treatment is represented as *p<0.05. Significant difference when compared to BMP-2 treatment alone is represented as **p=0.05. # corresponds to p=0.054 when comparing BMP-2 treatment alone to control group.

All rats survived the surgeries and healed uneventfully. The control resulted in negligible bone formation as ascertained by all the post-implantation analyses. Two dimensional x-ray analyses revealed that all other treatments containing BMP-2 exhibited varying degrees of bone mineralization, indicated by the deposition of irregularly-shaped nodules (FIG. 18A). This was verified by 3D µ-CT examination. We picked a predetermined threshold that resembles denser, cortical bone as this would be of direct clinical relevance. Treatment groups containing BMP-2 and GAG showed significantly more bone volume compared to control (p<0.05). Notably, the combination of BMP-2 with HS5 resulted in 2-folds more bone volume than BMP-2 treatment alone (p=0.05), while the combination of BMP-2 with either heparin (p=0.53) or bHS (p=0.59) only resulted in ~1.2 folds more bone than BMP-2. (FIG. 18B). The corresponding 3D images concur with the cortical bone values obtained.

Figure 18C:
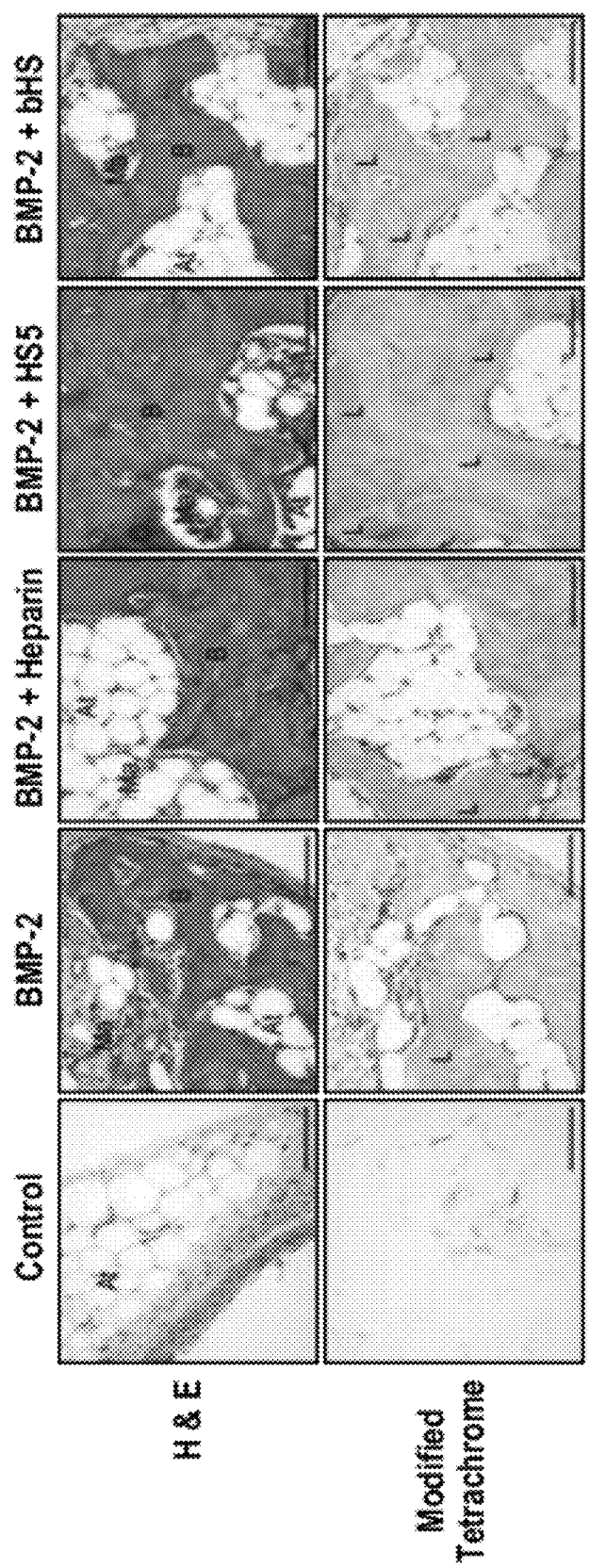

H & E-stained sections of all BMP-2-treated groups revealed the presence of osteoblasts on the surface of woven bone trabeculae, and the deposition of mature bone (with osteocytes in lacuna) adjacent to bone marrow elements, with the ones containing HS5 treatment clearly exhibiting the most (FIG. 18C). Modified tetrachrome-stained sections confirmed the above H & E findings. The sections stained deep blue with bright red patches and this is indicative of an osteoid layer with lamellar bone. Markedly, HS5 treatment resulted in a higher incidence of lamellar bone. Collectively, our in vivo data suggests that HS5 therapy, in combination with BMP-2, stimulated robust bone mineralization in a rat ectopic model.

Discussion

Heparan sulfate is known to mediate biological processes ranging from embryological development to adult physiology (Bishop J R, Schuksz M, Esko J D 2007 Heparan sulphate proteoglycans fine-tune mammalian physiology. Nature 446 (7139):1030-1037). This activity is linked to sulfate domains on HS chains that are tightly regulated and dependent on developmental stages and tissue origin (32-35). In our earlier work, we have demonstrated that temporal changes in HS expressed during osteogenesis was associated to a change in HS' biological function supporting the processes occurring during differentiation (Nurcombe V, Goh F J, Haupt L M, Murali S, Cool S M 2007 Temporal and functional changes in glycosaminoglycan expression during osteogenesis. Journal of Molecular Histology 38:469-481). Here, we demonstrate that HS originating from a bone marrow stromal cell line can better augment BMP-2-induced osteogenesis compared to heparin and HS originating from porcine intestinal mucosa and bovine kidney.

Niche-specific HSs have been observed to augment the generation and maintenance of hematopoietic stem cells (Gupta P, McCarthy J B, Verfaillie C M 1996 Stromal fibroblast heparan sulfate is required for cytokine-mediated ex vivo maintenance of human long-term culture-initiating cells. Blood 87(8):3229-3236) as well as osteoblast development (Jackson R A, Murali S, Van Wijnen A J, Stein G S, Nurcombe V, Cool S M 2007 Heparan sulfate regulates the anabolic activity of MC3T3-E1 preosteoblast cells by induction of Runx2. Journal of Cellular Physiology 210(1):38-50) and bone repair (Jackson R A, McDonald M M, Nurcombe V, Little D G, Cool S M 2006 The use of heparan sulfate to augment fracture repair in a rat fracture model. Journal of Orthopaedic Research 24(4):636-644). Hematopoietic stem cells residing in the same microenvironment as stomal stem cells are known to direct cell-fate decisions favoring osteogenesis through the secretion of BMP-2 and -6 (Jung Y G, Song J H, Shiozawa Y, Wang J C, Wang Z, Williams B, Havens A, Schneider A, Ge C X, Franceschi R T, McCauley L K, Krebsbach P H, Taichman R S 2008 Hematopoietic stem cells regulate mesenchymal stromal cell induction into osteoblasts thereby participating in the formation of the stem cell niche. Stem Cells 26(8):2042-2051). Thus, it is likely that bone marrow stromal cells express HS variants that not only support factors involved in hematopoiesis but also those involved in osteogenesis, such as BMP-2.

In the present study, the marrow stromal-derived HS5 enhanced BMP-2 activity in a similar manner to heparin. Heparin is believed to exert its effects upstream of the BMP receptor, as it did not alter intracellular signaling of BMPs in cells expressing constitutively active BMP receptor 1A (Takada T, Katagiri T, Ifuku M, Morimura N, Kobayashi M, Hasegawa K, Ogamo A, Kamijo R 2003 Sulfated polysaccharides enhance the biological activities of bone morphogenetic proteins. Journal of Biological Chemistry 278(44):43229-43235). Furthermore, previous work by Zhao et al (Zhao B H, Katagiri T, Toyoda H, Takada T, Yanai T, Fukuda T, Chung U I, Koike T, Takaoka K, Kamijo R 2006 Heparin potentiates the in vivo ectopic bone formation induced by bone morphogenetic protein-2. Journal of Biological Chemistry 281(32): 23246-23253) showed that heparin prolongs BMP-2 half-life in culture media, while Takada et al (supra) suggested that heparin maintains high amount of BMP-2 in culture media by preventing its accumulation in the cell/matrix portion. Our results support both of these findings; heparin and HS5 were able to stabilize BMP-2 and maintain its activity while also displacing BMP-2 from the cell surface where intracellular localization and degradation of BMP-2 has been shown to take place (Jiao X Y, Billings P C, O'Connell M P, Kaplan F S, Shore E M, Glaser D L 2007 Heparan sulfate proteoglycans (HSPGs) modulate BMP2 osteogenic bioactivity in C2C12 cells. Journal of Biological Chemistry 282(2):1080-1086). Taken together, the addition of heparin or HS5 enhanced BMP-2 activity mainly by increasing its bioavailability.

The bioavailability of BMP-2 is also influenced by the presence of antagonists. Noggin antagonizes BMP-2 by masking its receptor binding domain, thereby preventing receptor interactions (Groppe J, Greenwald J, Wiater E, Rodriguez-Leon J, Economides A N, Kwiatkowski W, Affolter M, Vale W W, Belmonte J C I, Choe S 2002 Structural basis of BMP signalling inhibition by the cystine knot protein Noggin. Nature 420(6916):636-642). Notably, heparin has been shown to reduce the antagonistic effect of noggin, a known heparin-binding protein (Zhao B H, Katagiri T, Toyoda H, Takada T, Yanai T, Fukuda T, Chung U I, Koike T, Takaoka K, Kamijo R 2006 Heparin potentiates the in vivo ectopic bone formation induced by bone morphogenetic protein-2. Journal of Biological Chemistry 281(32):23246-23253 and Paine-Saunders S, Viviano B L, Economides A N, Saunders S 2002 Heparan sulfate proteoglycans retain Noggin at the cell surface—A potential mechanism for shaping bone morphogenetic protein gradients. Journal of Biological Chemistry 277 (3):2089-2096). Early studies have shown that heparin promotes protein-protein interactions as was seen in FGF/FGF receptor and thrombin/antithrombin interactions in order to facilitate or inhibit protein activity (Li W, Johnson D J D, Esmon C T, Huntington J A 2004 Structure of the antithrombin-thrombin-heparin ternary complex reveals the antithrombotic mechanism of heparin. Nature Structural & Molecular Biology 11(9):857-862 and Pellegrini L, Burke D F, von Delft F, Mulloy B, Blundell T L 2000 Crystal structure of fibroblast growth factor receptor ectodomain bound to ligand and heparin. Nature 407(6807):1029-1034). In the case of BMP-2, heparin and HS5 can induce activation by preventing the interaction between BMP-2 and its antagonist noggin. Interestingly, neither pHS nor bHS enhanced BMP-2 bioavailability by enhancing BMP-2 stability and preventing BMP-2/noggin interaction. Despite their higher binding capacity for BMP-2 (compared to HS5) pHS and bHS only moderately enhanced BMP-2 activity through a single mechanism of displacing BMP-2 from cell surface bound HSPGs. Takada et al (supra) and Sanderson et al (Sanderson R D, Turnbull J E, Gallagher J T, Lander A D 1994 Fine structure of heparan sulfate regulates syndecan-1 function and cell behavior. J Biol Chem 269(18):13100-6) showed that the degree of GAG sulfation is not strictly correlated to bioactivity and that the sequence of sulfation is more of a determining factor. In the current work, we showed that the binding capacity that is likely influenced by the degree and pattern of sulfation of a given GAG chain does not necessarily dictate its bioactivity, creating another layer of complexity behind the structure-function correlation in HS bioactivity.

Unwanted side effects generated due to the promiscuous binding of heparin to various types of proteins and molecules may offset heparin's positive effect toward BMP-2-induced osteogenesis. In the present study, HS5 and heparin equally enhanced BMP-2-induced osteocalcin transcript expression. Osteocalcin, generally considered a late osteogenic marker, is believed to act as a promoter for the nucleation of intermediate calcium phosphate structures in mineralized bone (Gelinksy M, Lenhard S, Simon P, Born R, Domaschke H, Pompe W 2004 Influence of osteocalcin on in vitro mineralization of collagen type I 8th International Conference on the Chemistry and Biology of Mineralized Tissues. University of Toronto Press, Toronto, Canada Banff, Alberta, Canada, pp 230-233). Interestingly, despite elevated level of BMP-2-induced osteocalcin in the presence of heparin, extracellular matrix mineralization was inhibited. Previous studies have demonstrated a decrease in calcium level in serum and plasma following intramuscular and intravenous heparin injection (Bonilla C A, Stringham R M, Jr., Lytle I M 1968 Effect of heparin on serum calcium concentrations in mice. Nature 217(5135):1281-2 and Goldsmith M W, Parry D J 1968 An investigation into the mechanism of the in vitro fall in rabbit plasma calcium which follows intravenous heparin injection. Clin Chim Acta 19(3):429-38). It was suggested that heparin behaves as a polyelectrolyte by forming a complex with calcium to neutralize the negative charge along its chain (Rubenstein D L, Robert J M, Peng J 1995 Multinuclear magnetic resonance studies of the interaction of inorganic cations with heparin. Carbohydrate Research 278(2):239-256). Alternatively, heparin may also reduce available calcium by inducing the release of lipoprotein lipase, which results in increased concentration of fatty acids that can form insoluble calcium salts (Goldsmith M W, Parry D J 1968 An investigation into the mechanism of the in vitro fall in rabbit plasma calcium which follows intravenous heparin injection. Clin Chim Acta 19(3):429-38). Accordingly, heparin may inhibit matrix mineralization in C2C12 cells despite elevated osteocalcin production in the presence of BMP-2 by depleting calcium ions.

Heparan sulfate, particularly HS5, has the potential to substitute heparin's function as a vehicle that introduces BMP-2 at a more physiological concentration and in a sustained manner. HS5 possesses comparable activity to heparin with minimal side effects. As mentioned earlier, heparin generated an unexpected negative effect toward terminal osteogenic differentiation and possesses strong anticoagulant activity, while HS5 did not. Thus, depending on the dosage, heparin may not only prevent bone mineralization but also prevent the coagulation process that is an important initial step in wound repair. The current work has demonstrated the variability in the bioactivity, growth factor binding affinity and biological functions of different HS species that are likely influenced by their degree and motif of sulfation.

In this study, we find that marrow-derived HS (HS5) is an effective adjuvant of BMP-2. HS5 can bind BMP-2 and augment BMP-2-induced bone formation to generate a mature lamellar structure containing dense mineralized regions akin to cortical bone. Furthermore, HS5 lacks the anti-coagulant activity present in heparin. Heparin's anti-coagulant activity has been attributed to its interaction with antithrombin through a unique 3-O-sulfated pentasaccharide motif [H. E. Conrad. Heparin-Binding Protein. San Diego: Academic Press; 1998.]. This 3-O-sulfate group is uncommon in HS [B. Gorsi, S. E. Stringer. Tinkering with heparan sulfate sulfation to steer development. Trends Cell Biol. 17 (2007) 173-177.]. Consequently, only a small percentage of naturally occurring HS is able to bind to antithrombin and promote anticoagulation [J. D. Esko, K. Kimata, U. Lindahl. Proteoglycans and sulfated glycosaminoglycans. In: Varki A, Cummings R D, Esko J D, Freeze H H, Stanley P, Bertozzi C R, Hart G W, Etzler M E, editors. Essentials of Glycobiology. 2nd ed. La Jolla, Calif.: Cold Spring Harbor Laboratory Press; 2008.]. Even though we were not able to confirm the absence of 3-O sulfation in HS5 due to the lack of appropriate disaccharide standards, data from the anti-coagulation assay suggests minimal presence. The favorable biological properties of HS-5—reflected by improved BMP2 activity and virtually absent anti-coagulant activity—render it a very selective bone anabolic agent.

Mechanistically, HS5 sustains BMP-2 activity in a similar fashion to heparin by (i) prolonging its half-life, (ii) decreasing interactions with the BMP-2 antagonist noggin, and (iii) decreasing BMP-2 localization on cell surface HSPG. Cell surface HSPG is known to modulate the diffusion of BMP-2 and noggin into the extracellular space [S. Paine-Saunders, B. L. Viviano, A. N. Economides, S. Saunders. Heparan sulfate proteoglycans retain Noggin at the cell surface—A potential mechanism for shaping bone morphogenetic protein gradients. J. Biol. Chem. 277 (2002) 2089-2096., X. Y. Jiao, P. C. Billings, M. P. O'Connell, F. S. Kaplan, E. M. Shore, D. L. Glaser. Heparan sulfate proteoglycans (HSPGs) modulate BMP2 osteogenic bioactivity in C2C12 cells. J. Biol. Chem. 282 (2007) 1080-1086., B. L. Viviano, S. Paine-Saunders, N. Gasiunas, J. Gallagher, S. Saunders. Domain-specific modification of heparan sulfate by Qsulf1 modulates the binding of the bone morphogenetic protein antagonist noggin. J. Biol. Chem. 279 (2004) 5604-5611]. The interaction between HSPG and BMP-2 can lead to increased heteromeric BMP receptor assembly [W. J. Kuo, M. A. Digman, A. D. Lander. Heparan sulfate acts as a bone morphogenetic protein co-receptor by facilitating ligand-induced receptor hetero-oligomerization. Mol. Biol. Cell 21 (2010) 4028-4041.] and enhanced BMP signaling. It can also negatively regulate BMP-2 activity by facilitating BMP-2 internalization and reducing its availability to the receptor [X. Y. Jiao, P. C. Billings, M. P. O'Connell, F. S. Kaplan, E. M. Shore, D. L. Glaser. Heparan sulfate proteoglycans (HSPGs) modulate BMP2 osteogenic bioactivity in C2C12 cells. J. Biol. Chem. 282 (2007) 1080-1086.].

Additionally, endogenous HSPG can confine noggin and its inhibitory effect in the pericellular environment [B. L. Viviano, S. Paine-Saunders, N. Gasiunas, J. Gallagher, S. Saunders. Domain-specific modification of heparan sulfate by Qsulf1 modulates the binding of the bone morphogenetic protein antagonist noggin. J. Biol. Chem. 279 (2004) 5604-5611.]. Moderate disruption of BMP-2/HSPG interaction by HS5 that appears evident from our FACS data may positively regulate BMP-2 activity by decreasing BMP-2 internalization while minimizing disruption of BMP receptor assembly. Moreover, the decrease in the inhibitory effect of noggin by HS5 may not exclusively be through direct interference with the BMP-2/noggin interaction (as illustrated by our immunoprecipitation results). HS5 may delocalize noggin and BMP-2 from the cell surface thereby diminishing its probability of complexing in the pericellular space. Thus, our data indicate that the BMP2 related bone anabolic effects of HS5 are most likely achieved by more than one molecular mechanism and these mechanisms together sustain BMP2 signaling over a more prolonged period than BMP2 alone.

The current work demonstrates the bioactivity and osteogenic ligand binding capacity of HS5. Co-administration of HS5 permits delivery of BMP-2 at lower and more physiological concentrations while retaining its osteogenic activity. The bone promoting biological function of HS5 may be linked to the unique degree and pattern of sulfation of GAGs from human bone marrow stromal cells. Compared to heparin that is derived from porcine intestinal mucosa, HS5 may be particularly adept at enhancing BMP-2 signaling while minimizing its effect on non-osteogenic factors.

REFERENCES

1. Rocha V and Gluckman E. Clinical use of umbilical cord blood hematopoietic stem cells. Biol Blood Marrow Transplant. 2006; 12(1 Suppl 1):34-41.
2. Rocha V and Gluckman E. Improving outcomes of cord blood transplantation: HLA matching, cell dose and other graft- and transplantation-related factors. Br J Haematol. 2009; 147(2):262-274.
3. Gratwohl A, Baldomero H, Schwendener A, Gratwohl M, Apperley J, Frauendorfer K, and Niederwieser D. The EBMT activity survey 2008 impact of team size, team density and new trends. Bone Marrow Transplant. 2010): 1-8.
4. Delaney C, Heimfeld S, Brashem-Stein C, Voorhies H, Manger R L, and Bernstein I D. Notch mediated expansion of human cord blood progenitor cells capable of rapid myeloid reconstitution. Nat Med. 2010; 16(2):232-236.
5. da Silva C L, Goncalves R, Crapnell K B, Cabral J M S, Zanjani E D, and Almeida-Porada G. A human stromal-based serum-free culture system supports the ex vivo expansion/maintenance of bone marrow and cord blood hematopoietic stem/progenitor cells. Exp Hematol. 2005; 33(7):828-835.
6. De Angeli S, Di Liddo R, Buoro S, Toniolo L, Conconi M T, Belloni A S, Parnigotto P P, and Nussdorfer G G. New immortalized human stromal cell lines enhancing in vitro expansion of cord blood hematopoietic stem cells. Int J Mol Med. 2004; 13(3):363-371.
7. Gupta P, McCarthy J B, and Verfaillie C M. Stromal fibroblast heparan sulfate is required for cytokine-mediated ex vivo maintenance of human long-term culture-initiating cells. Blood. 1996; 87(8):3229-3236.
8. Kadereit S, Deeds L S, Haynesworth S E, Koc O N, Kozik M M, Szekely E, Daum-Woods K, Goetchius G W, Fu P F, Welniak L A, Murphy W J, and Laughlin M J. Expansion of LTC-ICs and maintenance of p21 and BCL-2 expression in cord blood CD34(+)/CD38(−) early progenitors cultured over human MSCs as a feeder layer. Stem Cells. 2002; 20(6):573-582.
9. Kobune M, Kawano Y, Kato J, Ito Y, Chiba H, Nakamura K, Fujimi A, Matsunaga T, Hamada H, and Niitsu Y. Expansion of CD34(+) cells on telomerized human stromal cells without losing erythroid-differentiation potential in a serum-free condition. Int J Hematol. 2005; 81(1):18-25.
10. Dexter T M. Stromal cell associated haemopoiesis. J Cell Physiol Suppl. 1982; 1:87-94.
11. Roberts R, Gallagher J, Spooncer E, Allen T D, Bloomfield F, and Dexter T M. Heparan sulphate bound growth factors: a mechanism for stromal cell mediated haemopoiesis. Nature. 1988; 332(6162):376-378.
12. Roecklein B A and Torokstorb B. Functionally distinct human marrow stromal cell-lines immortalized by transduction with the human papilloma-virus E6/E7 genes. Blood. 1995; 85(4):997-1005.
13. Coombe D R. Biological implications of glycosaminoglycan interactions with haemopoietic cytokines. Immunology and Cell Biology. 2008; 86(7):598-607.
14. Gordon M Y, Riley G P, Watt S M, and Greaves M F. Compartmentalization of a haematopoietic growth factor (GM-CSF) by glycosaminoglycans in the bone marrow microenvironment. Nature. 1987; 326(6111):403-405.
15. Bishop J R, Schuksz M, and Esko J D. Heparan sulphate proteoglycans fine-tune mammalian physiology. Nature. 2007; 446(7139):1030-1037.
16. Esko J D and Linhardt R J. Proteins that bind sulfated glycosaminoglycans. In: A. Varki, R. D. Cummings, J. D. Esko, H. H. Freeze, P. Stanley, C. R. Bertozzi, G. W. Hart, and M. E. Etzler (eds.), Essentials of Glycobiology, Cold Spring Harbor Laboratory Press, La Jolla, Calif., 2008.
17. Nurcombe V, Goh F J, Haupt L M, Murali S, and Cool S M. Temporal and functional changes in glycosaminoglycan expression during osteogenesis. Journal of Molecular Histology. 2007; 38:469-481.
18. Haupt L M, Murali S, Mun F K, Teplyuk N, Mei L F, Stein G S, van Wijnen A J, Nurcombe V, and Cool S M. The heparan sulfate proteoglycan (HSPG) glypican-3 mediates commitment of MC3T3-E1 cells toward osteogenesis. J Cell Physiol. 2009; 220(3):780-791.
19. Dombrowski C, Song S J, Chuan P, Lim X, Susanto E, Sawyer A A, Woodruff M A, Hutmacher D W, Nurcombe V, and Cool S M. Heparan sulfate mediates the proliferation and differentiation of rat mesenchymal stem cells. Stem Cells Dev. 2009; 18(4):661-670.
20. Ng K W, Speicher T, Dombrowski C, Helledie T, Haupt L M, Nurcombe V, and Cool S M. Osteogenic differentiation of murine embryonic stem cells is mediated by fibroblast growth factor receptors. Stem Cells Dev. 2007; 16(2):305-318.
21. Murali S, Manton K J, Tjong V, Su X D, Haupt L M, Cool S M, and Nurcombe V. Purification and characterization of heparan sulfate from human primary osteoblasts. J Cell Biochem. 2009; 108(5):1132-1142.
22. Schofield R. The relationship between the spleen colony-forming cell and the haematopoietic stem cell. Blood Cells. 1978; 4:7-25.
23. Wight T N, Kinsella M G, Keating A, and Singer J W. Proteoglycans in human long-term bone marrow cultures—biochemical and ultrastructural analyses. Blood. 1986; 67(5):1333-1343.
24. Brickman Y G, Ford M D, Small D H, Bartlett P F, and Nurcombe V. Heparan sulfates mediate the binding of basic fibroblast growth factor to a specific receptor on neural precursor cells. J Biol Chem. 1995; 270(42):24941-24948.
25. Li W, Johnson D J D, Esmon C T, and Huntington J A. Structure of the antithrombin-thrombinheparin ternary complex reveals the antithrombotic mechanism of heparin. Nat Struct Mol Biol. 2004; 11(9):857-862.
26. Ostrovsky O, Berman B, Gallagher J, Mulloy B, Femig D G, Delehedde M, and Ron D. Differential effects of heparin saccharides on the formation of specific fibroblast growth factor (FGF) and FGF receptor complexes. Journal of Biological Chemistry. 2002; 277(4):2444-2453.
27. Sanderson R D, Turnbull J E, Gallagher J T, and Lander A D. Fine structure of heparan sulphate regulates syndecan-1 function and cell behavior. J Biol Chem. 1994; 269(18): 13100-13106.
28. Takada T, Katagiri T, Ifuku M, Morimura N, Kobayashi M, Hasegawa K, Ogamo A, and Kamijo R. Sulfated polysaccharides enhance the biological activities of bone morphogenetic proteins. Journal of Biological Chemistry. 2003; 278(44):43229-43235.
29. Gupta P, Oegema T R, Brazil J J, Dudek A Z, Slungaard A, and Verfaillie CM. Structurally specific heparan sulfates support primitive human hematopoiesis by formation of a multimolecular stem cell niche. Blood. 1998; 92(12): 4641-4651.
30. Gupta P, Oegema T R, Jr., Brazil J J, Dudek A Z, Slungaard A, and Verfaillie C M. Human LTC-IC can be maintained for at least 5 weeks in vitro when interleukin-3 and a single chemokine are combined with O-sulfated heparan sulfates: requirement for optimal binding interactions of heparan sulfate with early-acting cytokines and matrix proteins. Blood. 2000; 95(1):147-155.
31. de Lima M, McMannis J, Gee A, Komanduri K, Couriel D, Andersson B S, Hosing C, Khouri I, Jones R, Champlin R, Karandish S, Sadeghi T, Peled T, Grynspan F, Daniely Y, Nagler A, and Shpall E J. Transplantation of ex vivo expanded cord blood cells using the copper chelator tetra-ethylenepentamine: a phase I/II clinical trial. Bone Marrow Transplantation. 2008; 41(9):771-778.
32. Jaroscak J, Goltry K, Smith A, Waters-Pick B, Martin P L, Driscoll T A, Howrey, Chao N, Douville J, Burhop S, Fu P, and Kurtzberg J. Augmentation of umbilical cord blood (UCB) transplantation with ex vivo-expanded UCB cells: results of a phase 1 trial using the AastromReplicell System. Blood. 2003; 101(12):5061-5067.
33. Shpall E J, Quinones R, Giller R, Zeng C, Baron A E, Jones R B, Bearman S I, Nieto Y, Freed B, Madinger N, Hogan C J, Slat-Vasquez V, Russell P, Blunk B, Schissel D, Hild E, Malcolm J, Ward W, and McNiece I K. Transplantation of ex vivo expanded cord blood. Biol Blood Marrow Transplant. 2002; 8(7):368-376.

34. Migliaccio A R, Adamson J W, Stevens C E, Dobrila N L, Carrier C M, and Rubinstein P. Cell dose and speed of engraftment in placental/umbilical cord blood transplantation: graft progenitor cell content is a better predictor than nucleated cell quantity. Blood. 2000; 96(8):2717-2722.
35. Bishop G B, Einhorn T A 2007 Current and future clinical applications of bone morphogenetic proteins in orthopaedic trauma surgery. International Orthopaedics 31(6): 721-727.
36. Dinopoulos H, Giannoudis P V 2007 (iv) The use of bone morphogenetic proteins (BMPs) in long-bone non-unions. Current Orthopaedics 21(4):268-279.
37. Gautschi O P, Frey S P, Zellweger R 2007 Bone morphogenetic proteins in clinical applications. Anz Journal of Surgery 77(8):626-631.
38. Garrison K R, Donell S, Ryder J, Shemilt I, Mugford M, Harvey I, Song F 2007 Clinical effectiveness and cost-effectiveness of bone morphogenetic proteins in the non-healing of fractures and spinal fusion: a systematic review. Health Technology Assessment 11(30).
39. Chung Y I, Ahn K M, Jeon S H, Lee S Y, Lee J H, Tae G 2007 Enhanced bone regeneration with BMP-2 loaded functional nanoparticle-hydrogel complex. Journal of Controlled Release 121(1-2):91-99.
40. Fu Y C, Nie H, Ho M L, Wang C K, Wang C H 2008 Optimized bone regeneration based on sustained release from three-dimensional fibrous PLGA/HAp composite scaffolds loaded with BMP-2. Biotechnology and Bioengineering 99(4):996-1006.
41. Jeon O, Song S J, Yang H S, Bhang S H, Kang S W, Sung M A, Lee J H, Kim B S 2008 Long-term delivery enhances in vivo osteogenic efficacy of bone morphogenetic protein-2 compared to short-term delivery. Biochemical and Biophysical Research Communications 369(2):774-780.
42. Karageorgiou V, Tomkins M, Fajardo R, Meinel L, Snyder B, Wade K, Chen J, Vunjak-Novakovic G, Kaplan D L 2006 Porous silk fibroin 3-D scaffolds for delivery of bone morphogenetic protein-2 in vitro and in vivo. Journal of Biomedical Materials Research Part A 78A(2):324-334.
43. Takada T, Katagiri T, Ifuku M, Morimura N, Kobayashi M, Hasegawa K, Ogamo A, Kamijo R 2003 Sulfated polysaccharides enhance the biological activities of bone morphogenetic proteins. Journal of Biological Chemistry 278(44):43229-43235.
44. Esko J D, Linhardt R J 2008 Proteins that bind sulfated glycosaminoglycans. In: Varki A, Cummings R D, Esko J D, Freeze H H, Stanley P, Bertozzi C R, Hart G W, Etzler M E (eds.) Essentials of Glycobiology. Cold Spring Harbor Laboratory Press, La Jolla, Calif.
45. Zhao B H, Katagiri T, Toyoda H, Takada T, Yanai T, Fukuda T, Chung U I, Koike T, Takaoka K, Kamijo R 2006 Heparin potentiates the in vivo ectopic bone formation induced by bone morphogenetic protein-2. Journal of Biological Chemistry 281(32):23246-23253.
46. Paine-Saunders S, Viviano B L, Economides A N, Saunders S 2002 Heparan sulfate proteoglycans retain Noggin at the cell surface—A potential mechanism for shaping bone morphogenetic protein gradients. Journal of Biological Chemistry 277(3):2089-2096.
47. Arnander C, Westermark A, Veltheim R, Docherty-Skogh A C, Hilborn J, Engstrand T 2006 Three-dimensional technology and bone morphogenetic protein in frontal bone reconstruction. Journal of Craniofacial Surgery 17(2):275-279.
48. Gittens S A, Bagnall K, Matyas J R, Lobenberg R, Uludag H 2004 Imparting bone mineral affinity to osteogenic proteins through heparin-bisphosphonate conjugates. Journal of Controlled Release 98(2):255-268.
49. Lin H, Zhaol Y, Sun W J, Chen B, Zhang J, Zhao W X, Xiao Z F, Dai J W 2008 The effect of crosslinking heparin to demineralized bone matrix on mechanical strength and specific binding to human bone morphogenetic protein-2. Biomaterials 29(9):1189-1197.
50. Atha D H, Stephens A W, Rosenberg R D 1984 Evaluation of critical groups required for the binding of heparin to antithrombin. Proceedings of the National Academy of Sciences 81(4):1030-1034.
51. Park S H, Silva M, Bahk W J, McKellop H, Lieberman J R 2002 Effect of repeated irrigation and debridement on fracture healing in an animal model. Journal of Orthopaedic Research 20(6):1197-1204.
52. Barbour L A, Kick S D, Steiner J F, LoVerde M E, Heddleston L N, Lear J L, Baron A E, Barton P L 1994 A prospective study of heparin-induced osteoporosis in pregnancy using bone densitometry. American Journal of Obstetrics and Gynecology 170(3):862-869.
53. Muir J M, Andrew M, Hirsh J, Weitz J I, Young E, Deschamps P, Shaughnessy S G 1996 Histomorphometric analysis of the effects of standard heparin on trabecular bone in vivo. Blood 88(4):1314-1320.
54. Chowdhury M H, Hamada C, Dempster D W 1992 Effects of heparin on osteoclast activity. Journal of Bone and Mineral Research 7(7):771-777.
55. Goldhaber P 1965 Heparin enhancement of factors stimulating bone resorption in tissue culture. Science 147:407-408.
56. Irie A, Takami M, Kubo H, Sekino-Suzuki N, Kasahara K, Sanai Y 2007 Heparin enhances osteoclastic bone resorption by inhibiting osteoprotegerin activity. Bone 41(2): 165-174.
57. Esko J D, Selleck S B 2002 Order out of chaos: Assembly of ligand binding sites in heparan sulfate. Annual Review of Biochemistry 71:435-471.
58. Murali S, Manton K J, Tjong V, Su X D, Haupt L M, Cool S M, Nurcombe V 2009 Purification and characterization of heparan sulfate from human primary osteoblasts. Journal of Cellular Biochemistry 108(5):1132-1142.
59. Osmond R I W, Kett W C, Skett S E, Coombe D R 2002 Protein-heparin interactions measured by BIAcore 2000 are affected by the method of heparin immobilization. Analytical Biochemistry 310(2):199-207.
60. Ng K W, Speicher T, Dombrowski C, Helledie T, Haupt L M, Nurcombe V, Cool S M 2007 Osteogenic differentiation of murine embryonic stem cells is mediated by fibroblast growth factor receptors. Stem Cells and Development 16(2):305-318.
61. Rolny C, Spillmann D, Lindahl U, Claesson-Welsh L 2002 Heparin amplifies platelet-derived growth factor (PDGF)-BB-induced PDGF alpha-receptor but not PDGF beta-receptor tyrosine phosphorylation in heparan sulfate-deficient cells—Effects on signal transduction and biological responses. Journal of Biological Chemistry 277(22): 19315-19321.
62. Brickman Y G, Ford M D, Small D H, Bartlett P F, Nurcombe V 1995 Heparan sulfates mediate the binding of basic fibroblast growth factor to a specific receptor on neural precursor cells. J Biol Chem 270(42):24941-8.
63. Akiyama S, Katagiri T, Namiki M, Yamaji N, Yamamoto N, Miyama K, Shibuya H, Ueno N, Wozney J M, Suda T 1997 Constitutively active BMP type I receptors transduce BMP-2 signals without the ligand in C2C12 myoblasts. Experimental Cell Research 235(2):362-369.

64. Namiki M, Akiyama S, Katagiri T, Suzuki A, Ueno N, Yamaji N, Rosen V, Wozney J M, Suda T 1997 A kinase domain-truncated type I receptor blocks bone morphogenetic protein-2-induced signal transduction in C2C12 myoblasts. Journal of Biological Chemistry 272(35):22046-22052.
65. Bishop J R, Schuksz M, Esko J D 2007 Heparan sulphate proteoglycans fine-tune mammalian physiology. Nature 446(7139):1030-1037.
66. Baldwin R J, ten Dam G B, van Kuppevelt T H, Lacaud G, Gallagher J T, Kouskoff V, Merry CLR 2008 A developmentally regulated heparan sulfate epitope defines a subpopulation with increased blood potential during mesodermal differentiation. Stem Cells 26(12):3108-3118.
67. Brickman Y G, Ford M D, Gallagher J T, Nurcombe V, Bartlett P F, Turnbull J E 1998 Structural modification of fibroblast growth factor-binding heparan sulfate at a determinative stage of neural development. Journal of Biological Chemistry 273(8):4350-4359.
68. Warda M, Toida T, Zhang F M, Sun P L, Munoz E, Xie J, Linhardt R J 2006 Isolation and characterization of heparan sulfate from various murine tissues. Glycoconjugate Journal 23(7-8):555-563.
69. Yamada S, Onishi M, Fujinawa R, Tadokoro Y, Okabayashi K, Asashima M, Sugahara K 2009 Structural and functional changes of sulfated glycosaminoglycans in *Xenopus laevis* during embryogenesis. Glycobiology 19(5):488-498.
70. Nurcombe V, Goh F J, Haupt L M, Murali S, Cool S M 2007 Temporal and functional changes in glycosaminoglycan expression during osteogenesis. Journal of Molecular Histology 38:469-481.
71. Gupta P, McCarthy J B, Verfaillie C M 1996 Stromal fibroblast heparan sulfate is required for cytokine-mediated ex vivo maintenance of human long-term culture-initiating cells. Blood 87(8):3229-3236.
72. Jackson R A, Murali S, Van Wijnen A J, Stein G S, Nurcombe V, Cool S M 2007 Heparan sulfate regulates the anabolic activity of MC3T3-E1 preosteoblast cells by induction of Runx2. Journal of Cellular Physiology 210(1):38-50.
73. Jackson R A, McDonald M M, Nurcombe V, Little D G, Cool S M 2006 The use of heparan sulfate to augment fracture repair in a rat fracture model. Journal of Orthopaedic Research 24(4):636-644.
74. Jung Y G, Song J H, Shiozawa Y, Wang J C, Wang Z, Williams B, Havens A, Schneider A, Ge C X, Franceschi R T, McCauley L K, Krebsbach P H, Taichman R S 2008 Hematopoietic stem cells regulate mesenchymal stromal cell induction into osteoblasts thereby participating in the formation of the stem cell niche. Stem Cells 26(8):2042-2051.
75. Jiao X Y, Billings P C, O'Connell M P, Kaplan F S, Shore E M, Glaser D L 2007 Heparan sulfate proteoglycans (HSPGs) modulate BMP2 osteogenic bioactivity in C2C12 cells. Journal of Biological Chemistry 282(2):1080-1086.
76. Groppe J, Greenwald J, Wiater E, Rodriguez-Leon J, Economides A N, Kwiatkowski W, Affolter M, Vale W W, Belmonte J C I, Choe S 2002 Structural basis of BMP signalling inhibition by the cystine knot protein Noggin. Nature 420(6916):636-642.
77. Li W, Johnson D J D, Esmon C T, Huntington J A 2004 Structure of the antithrombin-thrombin-heparin ternary complex reveals the antithrombotic mechanism of heparin. Nature Structural & Molecular Biology 11(9):857-862.
78. Pellegrini L, Burke D F, von Delft F, Mulloy B, Blundell T L 2000 Crystal structure of fibroblast growth factor receptor ectodomain bound to ligand and heparin. Nature 407(6807):1029-1034.
79. Sanderson R D, Turnbull J E, Gallagher J T, Lander A D 1994 Fine structure of heparan sulfate regulates syndecan-1 function and cell behavior. J Biol Chem 269(18):13100-6.
80. Gelinksy M, Lenhard S, Simon P, Born R, Domaschke H, Pompe W 2004 Influence of osteocalcin on in vitro mineralization of collagen type I 8th International Conference on the Chemistry and Biology of Mineralized Tissues. University of Toronto Press, Toronto, Canada Banff, Alberta, Canada, pp 230-233.
81. Bonilla C A, Stringham R M, Jr., Lytle I M 1968 Effect of heparin on serum calcium concentrations in mice. Nature 217(5135):1281-2.
82. Goldsmith M W, Parry D J 1968 An investigation into the mechanism of the in vitro fall in rabbit plasma calcium which follows intravenous heparin injection. Clin Chim Acta 19(3):429-38.
83. Rabenstein D L, Robert J M, Peng J 1995 Multinuclear magnetic resonance studies of the interaction of inorganic cations with heparin. Carbohydrate Research 278(2):239-256.

The invention claimed is:

1. Heparan sulphate HS5 substantially purified from the core protein, wherein the heparan sulphate has the following heparan lyase disaccharide digestion profile:

| Disaccharide | % Composition |
| --- | --- |
| ΔHexUA - GlcN | 22.11 ± 10% |
| ΔHexUA - GlcN,6S | 38.79 ± 10% |
| ΔHexUA - GlcNS | 4.20 ± 10% |
| ΔHexUA - GlcNAc,6s | 4.53 ± 10% |
| Other | 30.37 ± 10%. |

2. A method of increasing the number of committed clonogenic cells in a population of hematopoietic stem cells (HSCs), the method comprising culturing HSCs in vitro in the presence of heparan sulphate according to claim 1.

3. The method of claim 2 wherein the method comprises increasing the number of myeloid lineage-committed progenitor cells.

4. The method of claim 2 wherein the method comprises increasing the number of colony forming cells (CFC).

5. The method of claim 2 wherein the method comprises increasing the number of burst forming unit-erythroid (BFU-E).

6. The method of claim 2 wherein the method comprises increasing the number of colony forming unit-granulocyte macrophage (CFU-GM).

7. The method of claim 2 wherein the initial HSC population in the culture comprises at least 50% CD34+ cells.

8. The method of claim 2 wherein the HSC population is obtained from cord blood.

9. A method of promoting osteogenesis, the method comprising administering heparan sulphate according to claim 1 to osteoprogenitor cells.

10. Culture media comprising heparan sulphate according to claim 1.

11. A method of transplanting hematopoietic stem cells (HSCs) to a patient in need thereof, the method comprising transplanting a therapeutically effective amount of HSCs to the patient and administering a therapeutically effective amount of heparan sulphate according to claim 1 to the site of transplantation of the HSCs in the patient or to tissue that surrounds, is near to, or adjacent to the site of transplantation.

12. The method of claim 11 wherein the HSCs and heparan sulphate are administered in combination.

13. The method of claim 11 wherein the HSCs and heparan sulphate are administered separately.

14. A biocompatible implant or prosthesis comprising a biomaterial and heparan sulphate according to claim 1.

15. A method of treating a bone fracture in a patient, the method comprising administration of a therapeutically effective amount of heparan sulphate according to claim 1 to the patient.

16. The method of claim 15 wherein the method comprises administering said heparan sulphate to the tissue surrounding the fracture.

17. The method of claim 15 wherein administration of said heparan sulphate comprises injection of the heparan sulphate to the tissue surrounding the fracture.

18. The method of claim 15 wherein said heparan sulphate is formulated as a pharmaceutical composition or medicament comprising the heparan sulphate and a pharmaceutically acceptable carrier, adjuvant or diluent.

19. A method of treating a bone fracture in a patient, the method comprising surgically implanting a biocompatible implant or prosthesis, which implant or prosthesis comprises a biomaterial and a therapeutically effective amount of heparan sulphate according to claim 1, into tissue of the patient at or surrounding the site of fracture.

20. Heparan sulphate according to claim 1 wherein the heparan sulphate is isolated from human bone marrow stroma.

\* \* \* \* \*